US008969029B2

(12) United States Patent
Chandrapati et al.

(10) Patent No.: US 8,969,029 B2
(45) Date of Patent: Mar. 3, 2015

(54) BIOLOGICAL STERILIZATION INDICATOR, SYSTEM, AND METHODS OF USING SAME

(75) Inventors: Sailaja Chandrapati, Woodbury, MN (US); Jeffrey C. Pederson, Minneapolis, MN (US); Heather M. Webb, Woodbury, MN (US); Jeffrey D. Smith, Marine on St. Croix, MN (US); Kurt J. Halverson, Lake Elmo, MN (US); Bryan S. Behun, White Bear Lake, MN (US); Peter D. Ludowise, Cottage Grove, MN (US)

(73) Assignee: 3M Innovative Properties Company, St. Paul, MN (US)

(*) Notice: Subject to any disclaimer, the term of this patent is extended or adjusted under 35 U.S.C. 154(b) by 888 days.

(21) Appl. No.: 13/063,945

(22) PCT Filed: Oct. 12, 2009

(86) PCT No.: PCT/US2009/060332
§ 371 (c)(1),
(2), (4) Date: Mar. 15, 2011

(87) PCT Pub. No.: WO2010/045138
PCT Pub. Date: Apr. 22, 2010

(65) Prior Publication Data
US 2011/0182770 A1    Jul. 28, 2011

Related U.S. Application Data

(60) Provisional application No. 61/196,438, filed on Oct. 17, 2008.

(51) Int. Cl.
*C12Q 1/22* (2006.01)
*C12M 1/00* (2006.01)
(Continued)

(52) U.S. Cl.
CPC .... *C12Q 1/22* (2013.01); *A61L 2/28* (2013.01)
USPC .............................. 435/31; 435/287.4; 422/50

(58) Field of Classification Search
USPC ............................ 422/292, 50; 435/31, 287.4
See application file for complete search history.

(56) References Cited

U.S. PATENT DOCUMENTS

| 3,907,106 A | 9/1975 | Purrmann |
| 3,981,683 A | 9/1976 | Larsson |

(Continued)

FOREIGN PATENT DOCUMENTS

| AU | 2006-202594 | 1/2007 |
| DE | 2324296 | 12/1973 |

(Continued)

OTHER PUBLICATIONS

International Search Report PCT/US2009/060332, Feb. 4, 2011, 6 pgs.

(Continued)

*Primary Examiner* — Kevin Joyner
(74) *Attorney, Agent, or Firm* — Nicole J. Einerson

(57) ABSTRACT

A biological sterilization indicator, system, and methods of determining the effectiveness of a sterilization process. The biological sterilization indicator can include a locus of spores, a reservoir containing a liquid, and a sterilant path positioned to provide fluid communication between ambience and the locus of spores. The reservoir can have a closed state in which the reservoir is not in fluid communication with the locus of spores and an open state in which the reservoir is in fluid communication with the locus of spores. The biological sterilization indicator system can include the biological sterilization indicator and a detection device adapted to be coupled to the biological sterilization indicator. In some embodiments, the method can include assaying the spores for a detectable change in a characteristic, and detecting substantially all of the detectable change.

20 Claims, 17 Drawing Sheets

(51) Int. Cl.
*C12Q 1/68* (2006.01)
*A61L 2/28* (2006.01)

(56) References Cited

U.S. PATENT DOCUMENTS

| | | | |
|---|---|---|---|
| 4,291,122 A | 9/1981 | Orelski |
| 4,461,837 A | 7/1984 | Karle |
| 4,591,566 A | 5/1986 | Smith |
| 4,596,773 A | 6/1986 | Wheeler, Jr. |
| 4,674,661 A | 6/1987 | Herold |
| 4,732,850 A | 3/1988 | Brown |
| 4,839,291 A | 6/1989 | Welsh |
| 4,863,867 A | 9/1989 | Joyce |
| 4,883,641 A | 11/1989 | Wicks |
| 4,885,253 A | 12/1989 | Kralovic |
| 5,073,488 A | 12/1991 | Matner |
| 5,096,669 A | 3/1992 | Lauks |
| 5,223,401 A | 6/1993 | Foltz |
| 5,252,484 A | 10/1993 | Matner |
| 5,378,430 A | 1/1995 | Nieves |
| 5,405,580 A | 4/1995 | Palmer |
| 5,418,167 A | 5/1995 | Matner |
| 5,482,171 A | 1/1996 | Palmer |
| 5,516,648 A | 5/1996 | Malchesky |
| 5,529,931 A | 6/1996 | Narayan |
| 5,552,320 A | 9/1996 | Smith |
| 5,736,555 A | 4/1998 | Naka |
| 5,739,004 A | 4/1998 | Woodson |
| 5,750,184 A | 5/1998 | Imburgia |
| 5,770,393 A | 6/1998 | Dalmasso |
| 5,795,730 A | 8/1998 | Tautvydas |
| 5,801,010 A | 9/1998 | Falkowski |
| 5,830,683 A | 11/1998 | Hendricks |
| 5,872,004 A | 2/1999 | Bolsen |
| 5,922,592 A | 7/1999 | Tautvydas |
| 5,955,296 A | 9/1999 | Roll |
| 5,968,807 A | 10/1999 | Kaiser |
| 5,989,852 A | 11/1999 | Hendricks |
| 6,063,591 A | 5/2000 | Bolea |
| 6,096,533 A | 8/2000 | Tautvydas |
| D463,570 S | 9/2002 | Bedingham |
| 6,455,272 B1 | 9/2002 | Gillis |
| D463,863 S | 10/2002 | Carlson |
| 6,532,997 B1 | 3/2003 | Bedingham |
| 6,534,006 B2 | 3/2003 | Hehenberger |
| 6,623,955 B2 | 9/2003 | Matner |
| 6,627,159 B1 | 9/2003 | Bedingham |
| 6,656,919 B1 | 12/2003 | Baugh |
| 6,662,830 B2 | 12/2003 | Bedingham |
| 6,692,596 B2 | 2/2004 | Moll |
| D492,792 S | 7/2004 | Kokaisel |
| 6,814,935 B2 | 11/2004 | Harms |
| D502,775 S | 3/2005 | Kokaisel |
| 6,942,989 B2 | 9/2005 | Felkner |
| D513,075 S | 12/2005 | Kokaisel |
| 7,026,168 B2 | 4/2006 | Bedingham |
| 7,183,048 B2 | 2/2007 | Felkner |
| 7,192,554 B2 | 3/2007 | Read |
| 7,223,364 B1 | 5/2007 | Johnston |
| 7,374,040 B2 | 5/2008 | Lee |
| 7,476,368 B2 | 1/2009 | Sargent |
| 7,507,376 B2 | 3/2009 | Dufresne |
| 7,595,200 B2 | 9/2009 | Bedingham |
| 7,608,219 B2 | 10/2009 | Bancroft |
| 7,875,239 B2 | 1/2011 | Bancroft |
| 8,343,768 B2 | 1/2013 | Kyung-Hee Song |
| 8,357,083 B2 | 1/2013 | Nagai |
| 2002/0034823 A1 | 3/2002 | Kuepper |
| 2003/0064427 A1 | 4/2003 | Felkner |
| 2003/0133830 A1 | 7/2003 | Gonzalez |
| 2003/0235677 A1 | 12/2003 | Hanschen |
| 2004/0121471 A1 | 6/2004 | Dufresne |
| 2005/0014212 A1 | 1/2005 | Reymond |
| 2005/0014214 A1* | 1/2005 | Eveland et al. ............... 435/29 |
| 2005/0031494 A1 | 2/2005 | Harms |
| 2005/0074833 A1 | 4/2005 | Gillis |
| 2005/0079101 A1 | 4/2005 | Dufresne |
| 2006/0029524 A1 | 2/2006 | Carter |
| 2006/0183183 A1 | 8/2006 | Felkner |
| 2006/0188396 A1 | 8/2006 | Bedingham |
| 2006/0189000 A1 | 8/2006 | Bedingham |
| 2006/0228811 A1 | 10/2006 | Bedingham |
| 2006/0269451 A1 | 11/2006 | Bedingham |
| 2007/0238145 A1 | 10/2007 | Cote |
| 2007/0245810 A1 | 10/2007 | Carter |
| 2007/0281369 A1 | 12/2007 | Carter |
| 2008/0070272 A1 | 3/2008 | Franciskovich |
| 2008/0206801 A1 | 8/2008 | Dallmier |
| 2008/0261296 A1 | 10/2008 | Justi |

FOREIGN PATENT DOCUMENTS

| | | |
|---|---|---|
| EP | 0157121 | 10/1985 |
| EP | 1739187 | 1/2007 |
| WO | WO 00/50634 | 8/2000 |
| WO | WO 03/024491 | 3/2003 |
| WO | WO 2004/000569 | 12/2003 |
| WO | WO 2007/010245 | 1/2007 |
| WO | WO 2007/070310 | 6/2007 |
| WO | WO 2010/045433 | 4/2010 |
| WO | WO 2010/045517 | 4/2010 |

OTHER PUBLICATIONS

The State Intellectual Property Office of The People's Republic of China Search Report; Application No. 200980151169.4); 3 pgs; May 20, 2013.

* cited by examiner

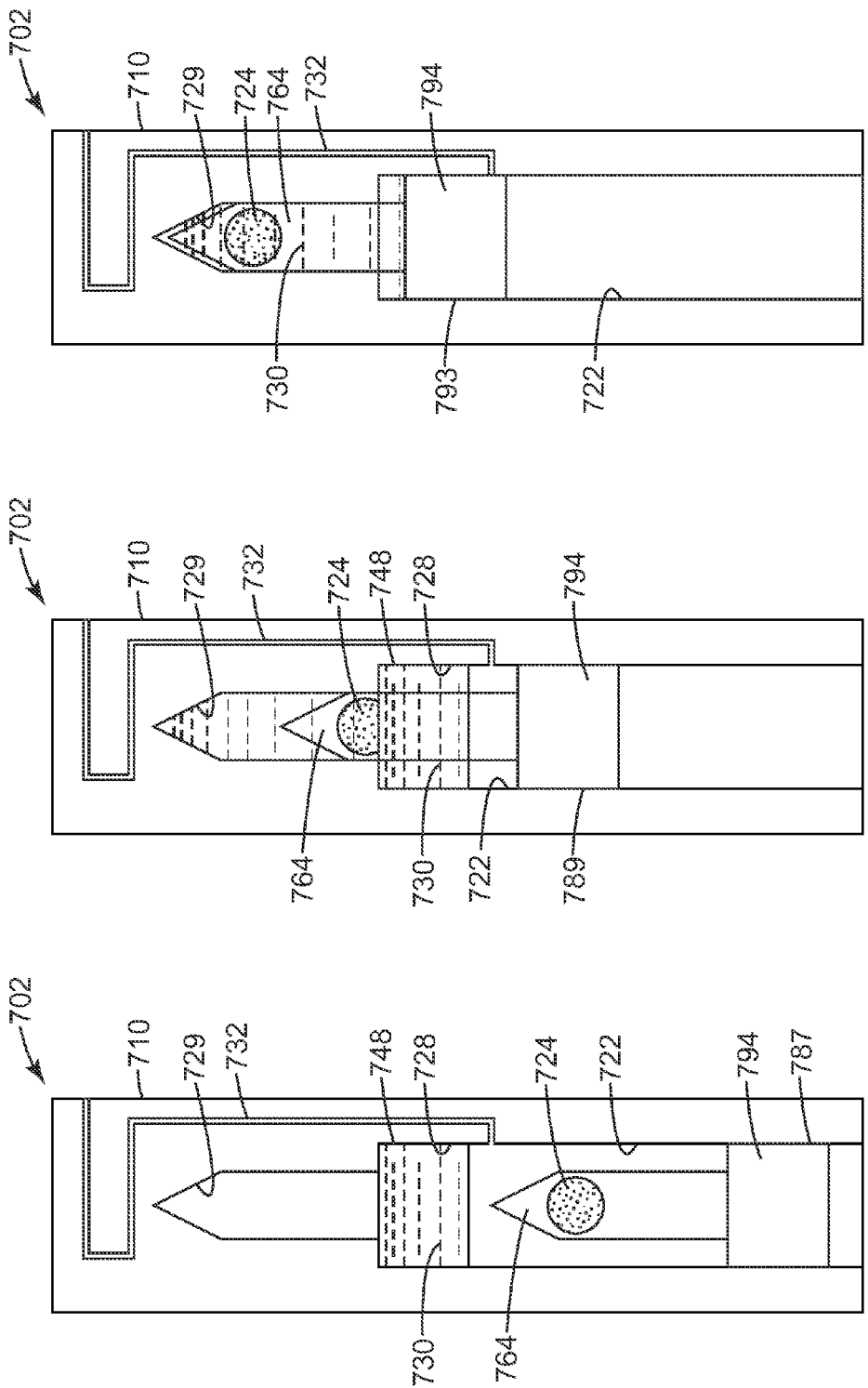

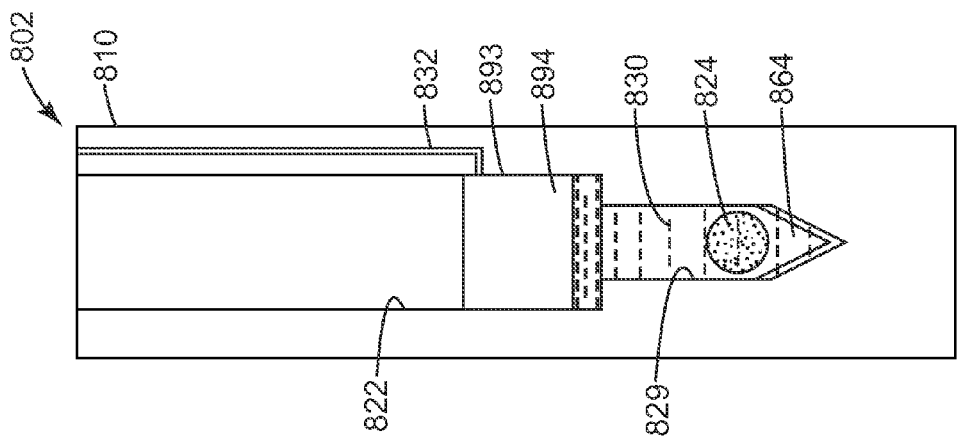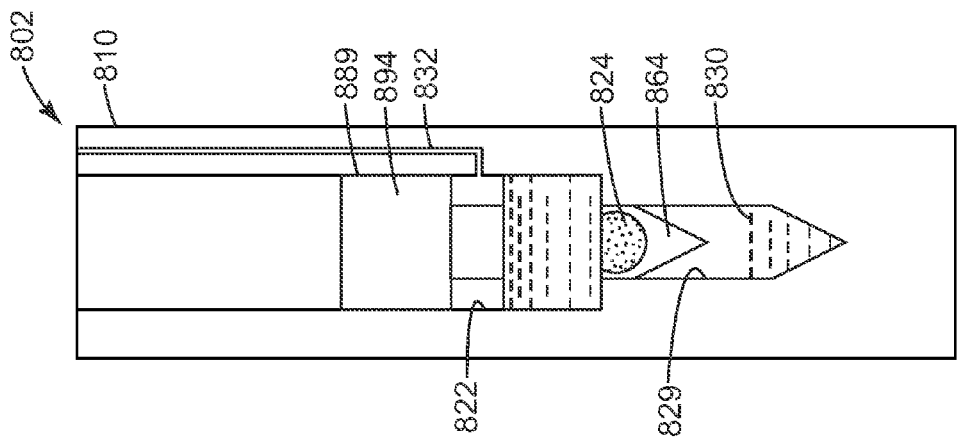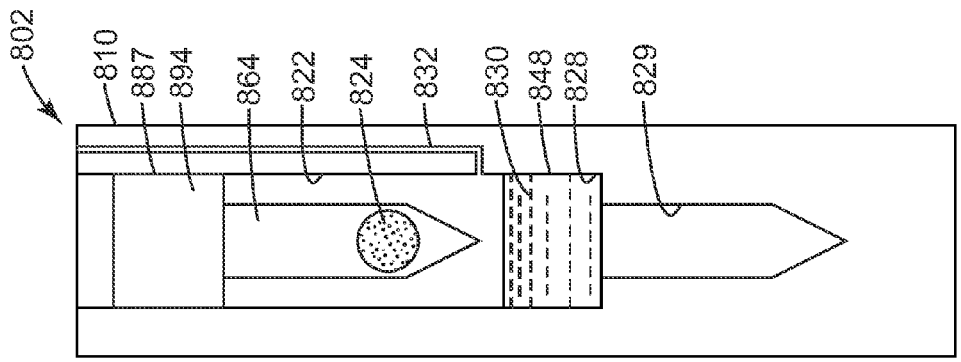

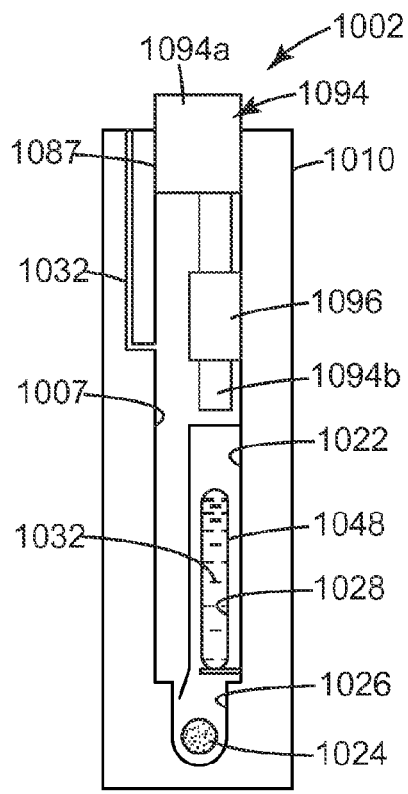
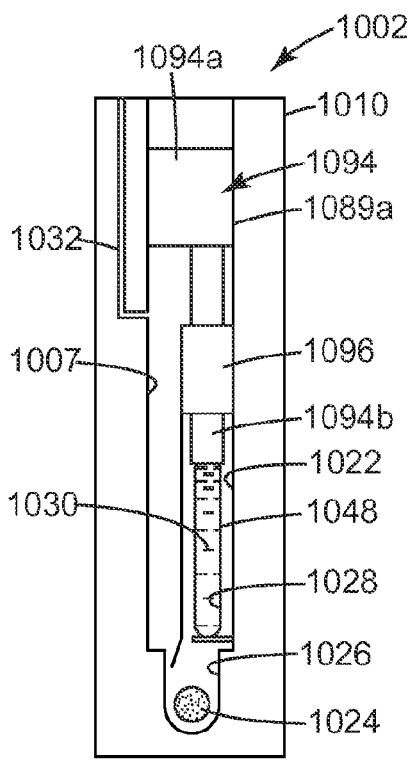
Fig. 15A    Fig. 15B
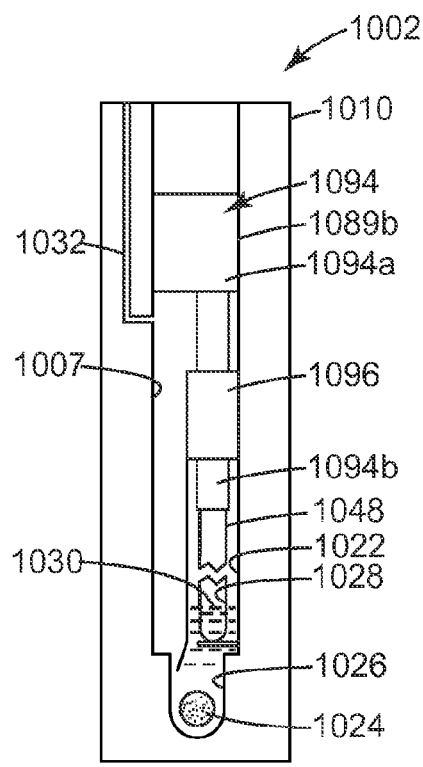
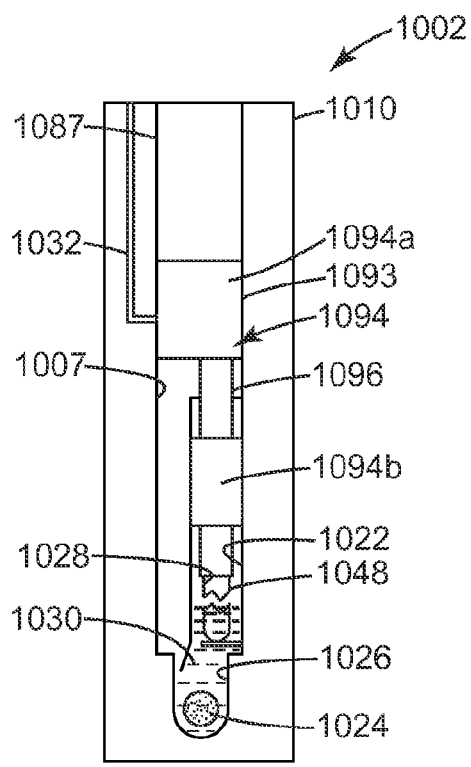
Fig. 15C    Fig. 15D

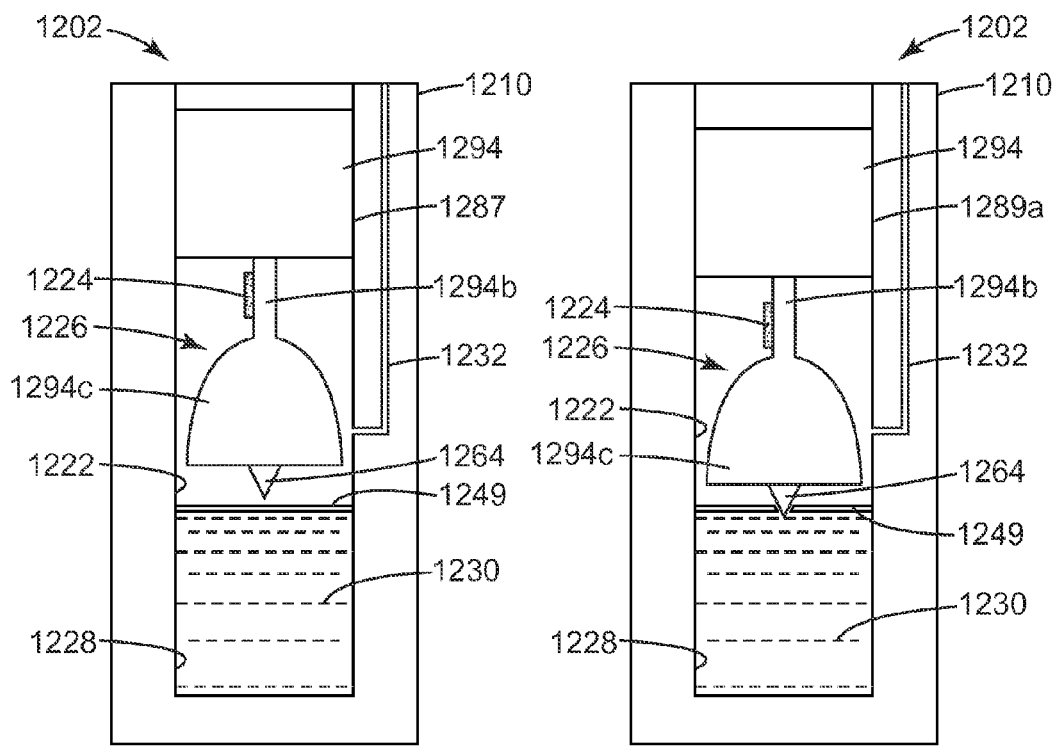
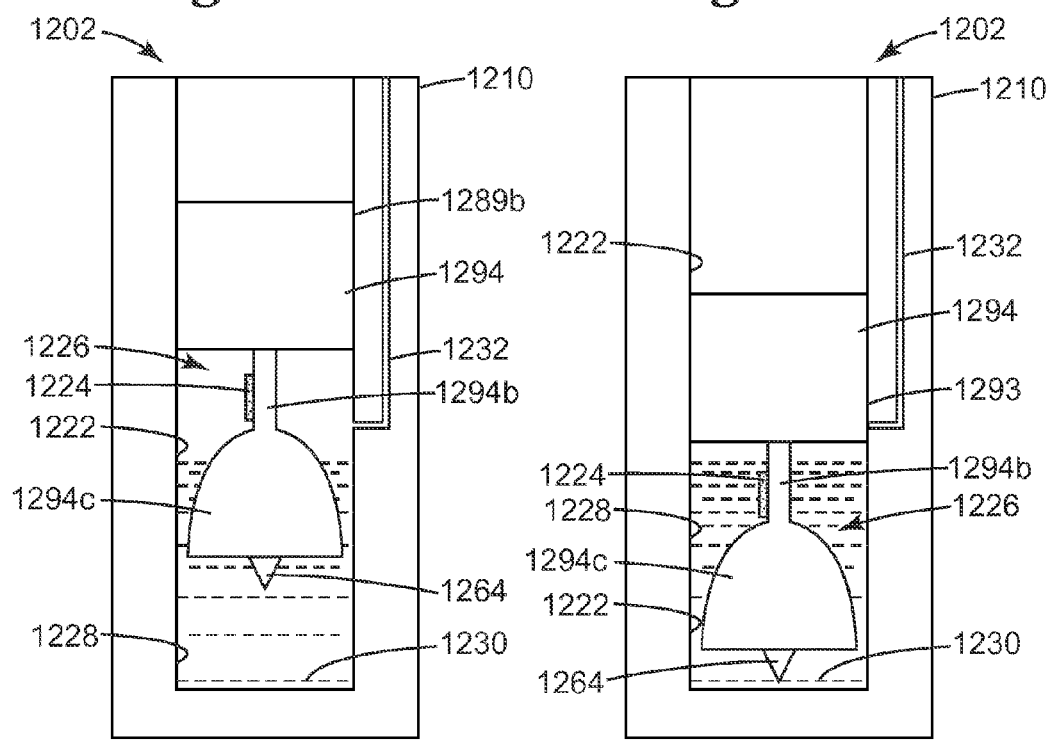

BIOLOGICAL STERILIZATION INDICATOR, SYSTEM, AND METHODS OF USING SAME

CROSS REFERENCE TO RELATED APPLICATIONS

This is a national stage filing under 35 U.S.C. 371 of PCT/US2009/060332, filed Oct. 12, 2009, which claims priority to U.S. Provisional Application No. 61/196,438, filed Oct. 17, 2008, the disclosure of which is incorporated by reference in its entirety herein.

FIELD

The present disclosure generally relates to sterilization indicators and systems, and particularly, to biological sterilization indicators and systems.

BACKGROUND

In a variety of industries, such as the health care industry but also in other industrial applications, it can be necessary to monitor the effectiveness of processes used to sterilize equipment such as medical devices, instruments and other non-disposable articles. In these settings, sterilization is generally defined as the process of completely destroying all viable microorganisms including structures such as viruses and spores. As a standard practice, hospitals include a sterility indicator with a batch of articles to assay the lethality of the sterilization process. Both biological and chemical sterility indicators have been used.

One standard type of biological sterility indicator includes a known quantity of test microorganisms, for example *Geobacillus stearothermophilus* (formerly *Bacillus stearothermophilus*) or *Bacillus atrophaeus* (formerly *Bacillus subtilis*) spores, which are many times more resistant to a sterilization process than most contaminating organisms. After the indicator is exposed to the sterilization process, the spores can be incubated in a nutrient medium to determine whether any of the spores survived the sterilization process, with spore growth indicating that the sterilization process was insufficient to destroy all of the microorganisms. Although advances have been made, the time period for determining this with certainty can be undesirably long.

Available chemical sterility indicators can be read immediately at the end of the sterilization process. However, the results indicate only that a particular condition was present during the sterilization process, such as the presence of a particular chemical or a temperature for a certain period of time.

It is generally considered that the response of living organisms to all conditions actually present is a more direct and reliable test for how effective a sterilization process is in achieving sterilization. Accordingly, there is a continuing need for biological sterility indicators, which can indicate the effectiveness of a sterilization process without an excessive delay after completion of the sterilization process, and yet can provide a high level of confidence that various sterility parameters were reached in the sterilization process.

SUMMARY

One aspect of the present disclosure provides a biological sterilization indicator system. The system can include a biological sterilization indicator and a detection device adapted to be coupled to the biological sterilization indicator. The biological sterilization indicator can include a housing, a locus of spores positioned in the housing, a reservoir containing a liquid, the reservoir having a closed state in which the reservoir is not in fluid communication with the locus of spores and an open state in which the reservoir is in fluid communication with the locus of spores, and a sterilant path positioned to provide fluid communication between ambience and the locus of spores. The detection device can include an actuator adapted to actuate a seal to move between a first position relative to the sterilant path in which the locus of spores is in fluid communication with ambience and a second position relative to the sterilant path in which the locus of spores is not in fluid communication with ambience, the seal adapted to be in the second position when the reservoir is in the open state.

Another aspect of the present disclosure provides a biological sterilization indicator system. The system can include a housing; a locus of spores positioned in the housing; a reservoir containing a liquid, the reservoir having a closed state in which the reservoir is not in fluid communication with the locus of spores and an open state in which the reservoir is in fluid communication with the locus of spores; a sterilant path positioned to provide fluid communication between ambience and the locus of spores when the reservoir is in a closed state; and a plug positioned to move between a first position in which the plug is not obstructing the sterilant path and the locus of spores is in fluid communication with ambience and a second position in which the plug is obstructing the sterilant path and the locus of spores is not in fluid communication with ambience, the plug adapted to be in the second position when the reservoir is in the open state.

Another aspect of the present disclosure provides a biological sterilization indicator system. The system can include a housing; a spore reservoir comprising a locus of spores, the spore reservoir having a volume; a reservoir containing a liquid, the reservoir having a closed state in which the reservoir is not in fluid communication with the spore reservoir and an open state in which the reservoir is in fluid communication with the spore reservoir; a sterilant path positioned to provide fluid communication between ambience and the spore reservoir; and a channel positioned to fluidly couple the spore reservoir and the reservoir, the channel having a cross-sectional area. The ratio of the volume of the spore reservoir to the cross-sectional area of the channel can be at least about 25.

Another aspect of the present disclosure provides a method for determining the effectiveness of a sterilization process. The method can include providing a housing; providing a locus of spores positioned in the housing; providing a reservoir containing a liquid, the reservoir having a closed state in which the reservoir is not in fluid communication with the locus of spores and an open state in which the reservoir is in fluid communication with the locus of spores; moving a sterilant into fluid communication with the locus of spores via a sterilant path while the reservoir is in the closed state to form sterilized spores; changing the reservoir from the closed state to the open state to combine the liquid and the sterilized spores to form a mixture; coupling at least a portion of the housing to a detection device; and sealing at least a portion of the sterilant path in response to coupling at least a portion of the housing to a detection device.

Another aspect of the present disclosure provides a biological sterilization indicator system. The system can include a biological sterilization indicator and a detection device adapted to be coupled to the biological sterilization indicator. The biological sterilization indicator can include a housing, a first reservoir positioned in the housing, the first reservoir in fluid communication with a locus of spores, a second reservoir containing a liquid, the second reservoir having a closed state in which the second reservoir is not in fluid communication with the first reservoir and an open state in which the second reservoir is in fluid communication with the first reservoir, and a sterilant path positioned to provide fluid communication between ambience and the locus of spores. The detection device can include means for inhibiting evaporation of the liquid when the reservoir is in the open state.

Another aspect of the present disclosure provides a biological sterilization system comprising a biological sterilization indicator and a detection device adapted to be coupled to the biological sterilization indicator. The biological sterilization indicator can include a housing, a locus of spores positioned in the housing, a reservoir containing a liquid, the reservoir having a closed state in which the reservoir is not in fluid communication with the locus of spores and an open state in which the reservoir is in fluid communication with the locus of spores, and a sterilant path positioned to provide fluid communication between ambience and the locus of spores. The detection device can include means for assaying the spores for a detectable change in a characteristic. At least one of the biological sterilization indicator and the detection device can include means for detecting substantially all of the detectable change.

Another aspect of the present disclosure provides a method for determining the effectiveness of a sterilization process. The method can include providing a locus of spores; providing fluid communication between a sterilant and the locus of spores during sterilization; providing a liquid that includes or is adapted to form a nutrient medium for the spores; protecting the liquid from fluid communication with the sterilant during sterilization; combining the liquid with the spores after sterilization; protecting the liquid from evaporation after combining the liquid with the spores; assaying the spores for a detectable change in a characteristic; and detecting substantially all of the detectable change.

Other features and aspects of the present disclosure will become apparent by consideration of the detailed description and accompanying drawings.

BRIEF DESCRIPTION OF THE DRAWINGS

FIGS. 12A-12C are schematic views of a biological sterilization indicator according to another embodiment of the present disclosure.

FIGS. 13A-13C are schematic views of a biological sterilization indicator according to another embodiment of the present disclosure.

FIGS. 15A-15D are schematic views of a biological sterilization indicator according to another embodiment of the present disclosure.

FIGS. 17A-17D are schematic cross-sectional views of a biological sterilization indicator according to another embodiment of the present disclosure.

DETAILED DESCRIPTION

Figure 1:
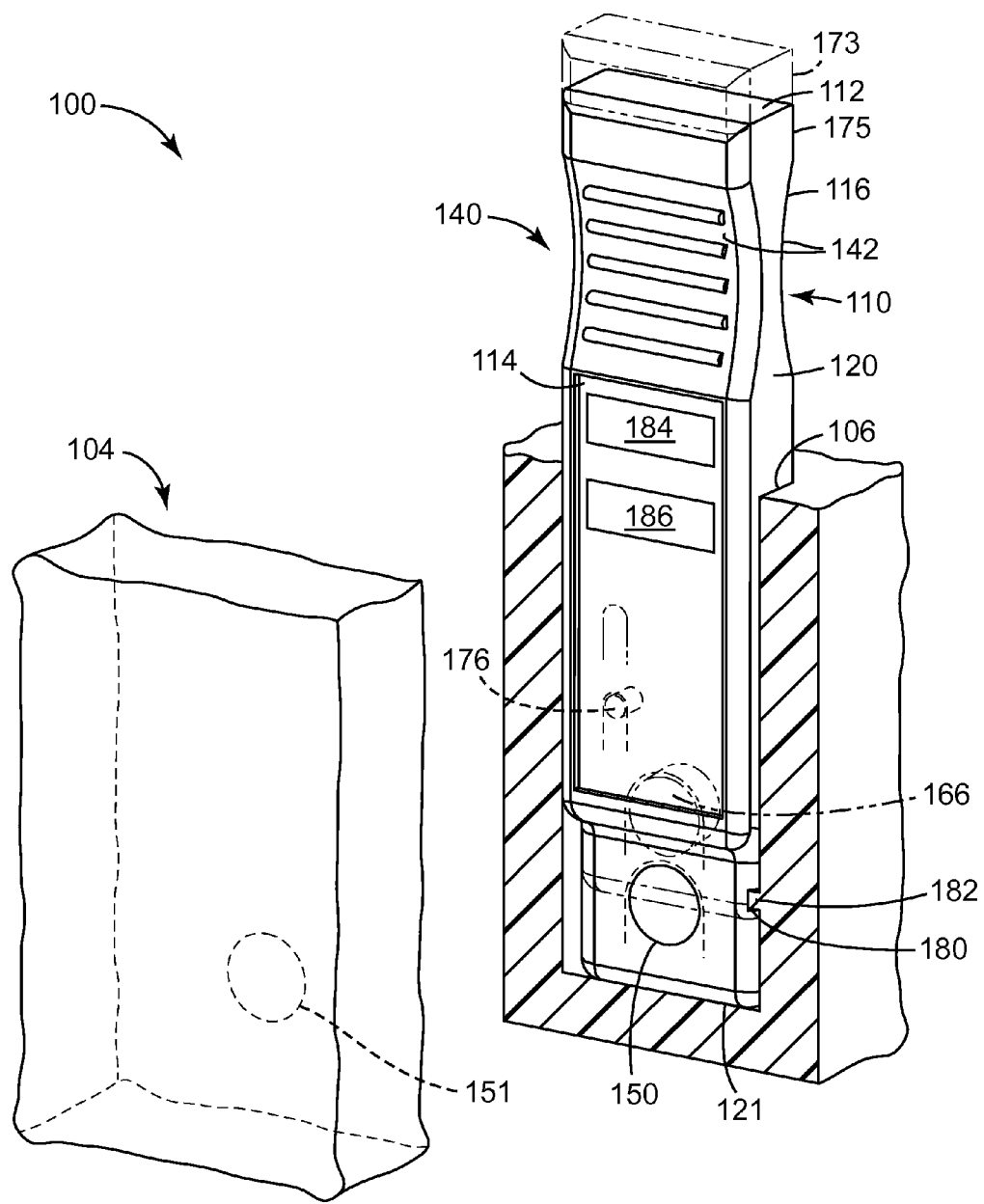
FIG. 1 is a front perspective view of a biological sterilization indicator system according to one embodiment of the present disclosure, the biological sterilization indicator system including a biological sterilization indicator and a detection device, the detection device shown broken into two portions.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to a sterilization indicator and system, and particularly, to a biological sterilization indicator and system. A biological sterilization indicator is also sometimes referred to as a "biological sterility indicator," or simply, a "biological indicator." Some embodiments of the biological sterilization indicator of the present disclosure are self-contained, have a generally planar configuration, and include smaller volumes than prior indicators to facilitate rapid read-out and to improve the effectiveness of the biological sterilization indicator and system.

Generally, microorganisms are chosen to be used in a biological sterilization indicator that are resistant to a particular sterilization process. The biological sterilization indicators of the present disclosure include a viable culture of a known species of microorganism, usually in the form of microbial spores. Bacterial spores, rather than the vegetative form of the organisms, are used at least partly because vegetative bacteria are known to be relatively easily killed by sterilizing processes. Spores also have superior storage characteristics and can remain in their dormant state for years. As a result, sterilization of an inoculum of a standardized spore strain provides a high degree of confidence that inactivation of all microorganisms in a sterilizing chamber has occurred.

By way of example only, the present disclosure describes the microorganisms used in the biological sterilization indicator as being "spores;" however, it should be understood that the type of microorganism (e.g., spore) used in a particular embodiment of the biological sterilization indicator is selected for being highly resistant to the particular sterilization process contemplated. Accordingly, different embodiments of the present disclosure may use different microorganisms, depending on the sterilization process for which the particular embodiment is intended.

The biological sterilization indicator system of the present disclosure can be used with a variety of sterilization processes including, but not limited to, exposure to steam, dry heat, gaseous or liquid agents (e.g., ethylene oxide, hydrogen peroxide, peracetic acid, ozone, or combinations thereof), radiation or combinations thereof. In at least some of the sterilization processes, an elevated temperature, for example, 50° C., 100° C., 121° C., 132° C., 134° C., or the like, is included or may be encountered in the process. In addition, elevated pressures may be encountered, for example, 15 psi ($1 \times 10^5$ Pa)

The spores used in a particular system are selected according to the sterilization process used. For example, for a steam sterilization process, *Geobacillus stearothermophilus* or *Bacillus stearothermophilus* can be used. In another example, for an ethylene oxide sterilization process, *Bacillus atrophaeus* (formerly *Bacillus subtilis*) can be used. In some embodiments, the sterilization process resistant spores can include, but are not limited to, at least one of *Geobacillus stearothermophilus*, *Bacillus stearothermophilus*, *Bacillus subtilis*, *Bacillus atrophaeus*, *Bacillus megaterium*, *Bacillus coagulans*, *Clostridium sporogenes*, *Bacillus pumilus*, or combinations thereof.

In general, the sterilization process includes placing the biological sterilization indicator of the present disclosure in a sterilizer. In some embodiments, the sterilizer includes a sterilization chamber that can be sized to accommodate a plurality of articles to be sterilized, and can be equipped with a means of evacuating air and/or other gases from the chamber and a means for adding a sterilant to the chamber. The biological sterilization indicator of the present disclosure can be positioned in areas of the sterilizer that are most difficult to sterilize (e.g., above the drain). Alternately, the biological sterilization indicator of the present disclosure can be positioned adjacent (or in the general proximity of) an article to be sterilized when the biological sterilization indicator is positioned in the sterilization chamber. In addition, the biological sterilization indicator can be positioned in process challenge devices that can be used in sterilizers.

The sterilization process can further include exposing the article(s) to be sterilized and the biological sterilization indicator to a sterilant. The sterilant can be added to the sterilization chamber after evacuating the chamber of at least a portion of any air or other gas present in the chamber. Alternatively, sterilant can be added to the chamber without evacuating the chamber. A series of evacuation steps can be used to assure that the sterilant reaches all desired areas within the chamber and contacts all desired article(s) to be sterilized, including the biological sterilization indicator.

FIGS. 1-4 illustrate a biological sterilization indicator system 100 according to one embodiment of the present disclosure. The biological sterilization indicator system 100 includes a biological sterilization indicator 102 and a detection device 104 (shown broken into two sections in FIG. 1), at least a portion of the biological sterilization indicator 102 dimensioned to be received within a recess 106 of the detection device 104.

The biological sterilization indicator 102 includes a housing 110 defined by at least one liquid impermeable wall. In the embodiment illustrated in FIGS. 1-4, the housing 110 is defined by a top wall 112, a front wall 114, a rear wall 116, a left side wall 118, a right side wall 120, and a bottom wall 121, all of which are liquid impermeable. Suitable materials for the walls 112, 114, 116, 118, 120 and 121 can include, but are not limited to, a glass, a metal (e.g., foil), a polymer (e.g., polycarbonate, polypropylene, polythyene, polystyrene, polyester, polymethyl methacrylate (PMMA or acrylic), acrylonitrile butadiene styrene (ABS), cyclo olefin polymer (COP), cyclo olefin copolymer (COC), polysulfone (PSU), polyethersulfone (PES), polyetherimide (PEI), polybutyleneterephthalate (PBT)), a ceramic, a porcelain, or combinations thereof.

The biological sterilization indicator 102 further includes a first reservoir 122 positioned in the housing 110, a locus 124 of spores positioned in a spore reservoir 126 that is in fluid communication with the first reservoir 122, a second reservoir 128 that contains a liquid 130, and a sterilant path 132 positioned to provide fluid communication between the first reservoir 122 and ambience. The sterilant path 132 includes a first inlet 134 defined by an aperture 136 in the rear wall 116 of the housing 110, a second inlet 135 defined by an aperture 137 in the right side wall 120 that can be used instead of, or in addition to, the first inlet 134 (e.g., in situations in which the first inlet 134 becomes blocked), and an outlet 138 adjacent the first reservoir 122 and defined by an aperture 139 in the first reservoir 122.

A barrier (e.g., a sterile barrier) can be positioned in the sterilant path 132 (e.g., at one or both of the inlet 134 and the inlet 135) to prevent contaminating or foreign organisms, objects or materials from entering the biological sterilization indicator 102. Such a barrier can include a gas-transmissive, microorganism-impermeable material, and can be coupled to the housing 110 by a variety of coupling means, including, but not limited to, an adhesive, a heat seal, or the like. Alternatively, the barrier can be coupled to the sterilant path 132 via a support structure (such as a cap) that is coupled to the housing 110 (e.g., in a snap-fit engagement, a screw-fit engagement, a press-fit engagement, or a combination thereof). During exposure to a sterilant, the sterilant can pass through the barrier into the sterilant path 132 and into the contact with the locus 124 of spores.

The biological sterilization indicator of the present disclosure generally keeps the liquid 130 and the locus 124 of spores separate but in close proximity (e.g., within the self-contained biological sterilization indicator 102) during sterilization, such that the liquid 130 and the spores can be readily combined after exposure to a sterilization process. The liquid 130 and the spores can be incubated while the biological sterilization indicator 102 is positioned in the recess 106 of the detection device 104, or the biological sterilization indicator 102 can be incubated prior to positioning the biological sterilization indicator 102 in the detection device 104. In some embodiments, when incubating the spores with the liquid 130, an incubation temperature above room temperature can be used. For example, in some embodiments, the incubation temperature is at least about 37° C., in some embodiments, the incubation temperature is at least about 50° C., and in some embodiments, at least about 60° C. In some embodiments, the incubation temperature is no greater than about 60° C., in some embodiments, no greater than about 50° C., and in some embodiments, no greater than about 40° C.

Figure 2:
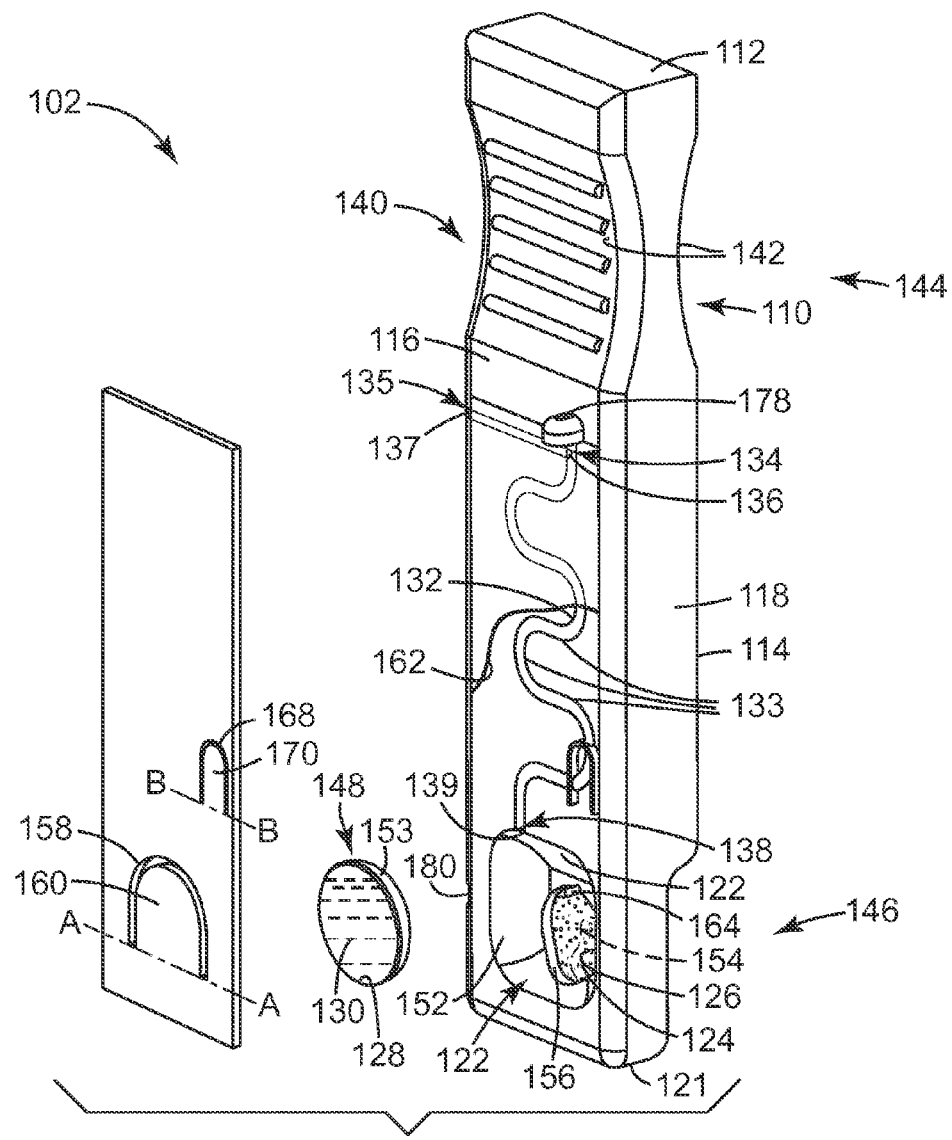
FIG. 2 is a rear exploded perspective view of the biological sterilization indicator of FIG. 1.

As shown in FIGS. 1 and 2, the biological sterilization indicator 102 includes a handle 140 which allows the biological sterilization indicator to be handled manually and/or robotically. As shown in FIGS. 1 and 2 by way of example only, in some embodiments, the handle 140 can include one or more depressions 142 to facilitate manual and/or robotic handling. However, it should be understood that a variety of other handle shapes and configurations can be used without departing from the spirit and scope of the present disclosure.

In the embodiment illustrated in FIGS. 1-4, the biological sterilization indicator 102 includes an upper portion 144 that includes the handle 140 and a lower portion 146 that includes the first reservoir 122, the second reservoir 128, the spore reservoir 126, and a detection window 150. In the embodiment illustrated in FIGS. 1-4, at least the lower portion 146 of the biological sterilization indicator 102 is shaped and dimensioned to cooperate with and/or to be received in a lower portion of the recess 106 of the detection device 104. However, it should be understood that the entire housing 110 can be shaped and dimensioned to cooperate with and/or be received in the recess 106. The detection device 104 can include a detection window 151 through which the detection device 104 can assay the spores (e.g., deliver a signal to the spores) and/or detect a change in the spores (e.g., receive a signal). As shown in FIG. 1, the detection window 150 can assay or detect via the detection window 150 of the biological sterilization indicator 102.

The recess 106 dimensioned to receive at least a portion of the housing 110 of the biological sterilization indicator 102 is shown by way of example only. However, it should be understood that the biological sterilization indicator 102 and the detection device 104 can be coupled together in a variety of ways to allow the detection window 151 of the detection device 104 to be positioned relative to the locus 124 of spores to allow the detection device 104 to assay and/or detect information from the biological sterilization indicator 102. For example, in some embodiments, the detection device 104 can include a protrusion or arm comprising the detection window 151 that is dimensioned to be received in a recess of the biological sterilization indicator 102 that includes the detection window 150. Other types of coupling between the biological sterilization indicator 102 and the detection device 104 are possible and are within the scope of the present disclosure. In addition, by way of example only, the detection windows 150, 151 are shown in FIG. 1 as being circular; however, it should be understood that a variety of shapes and configurations of detection windows 150, 151 can be used.

The detection device 104 can be adapted to detect a detectable change from the spores (e.g., from within the spore reservoir 126). That is, the detection device 104 can be adapted to detect a variety of characteristics, including, but not limited to, electromagnetic radiation (e.g., in the ultraviolet, visible, and/or infrared bands), fluorescence, luminescence, light scattering, electronic properties (e.g., conductance, impedance, or the like, or combinations thereof), turbidity, absorption, Raman spectroscopy, ellipsometry, or the like, or a combination thereof. Detection of such characteristics can be carried out by (and the detection device 104 can include) a fluorimeter, a spectrophotometer, colorimeter, or the like, or combinations thereof. In some embodiments, such as embodiments that measure fluorescence, visible light, etc., the detectable change is measured by detecting at a particular wavelength.

The spores and/or the liquid 130 can be adapted (e.g., labeled) to produce one or more of the above characteristics as a result of a biochemical reaction that is a sign of spore viability. As a result, no detectable change (e.g., as compared to a baseline or background reading) can signify an effective sterilization process, whereas a detectable change can signify an ineffective sterilization process. In some embodiments, the detectable change can include a rate at which one or more of the above characteristics is changing (e.g., increasing fluorescence, decreasing turbidity, etc.).

In some embodiments, spore viability can be determined by exploiting enzyme activity. As described in Matner et al., U.S. Pat. No. 5,073,488, entitled "Rapid Method for Determining Efficacy of a Sterilization Cycle and Rapid Read-out Biological Indicator," which is incorporated herein by reference, enzymes can be identified for a particular type of spore in which the enzyme has particularly useful characteristics that can be exploited to determine the efficacy of a sterilization process. Such characteristics can include the following: (1) the enzyme, when subjected to sterilization conditions which would be sufficient to decrease a population of $1 \times 10^6$ test microorganisms by about 6 logs (i.e., to a population of about zero as measured by lack of outgrowth of the test microorganisms), has a residual activity which is equal to "background" as measured by reaction with a substrate system for the enzyme; and (2) the enzyme, when subjected to sterilization conditions sufficient only to decrease the population of $1 \times 10^6$ test microorganisms by at least 1 log, but less than 6 logs, has enzyme activity greater than "background" as measured by reaction with the enzyme substrate system. The enzyme substrate system can include a substance, or mixture of substances, which is acted upon by the enzyme to produce a detectable enzyme-modified product, as evident by a detectable change.

In some embodiments, the detectable change in a characteristic can be induced by an active protease, which can be detected in the presence of a labeled protease substrate, as described in greater detail in co-pending U.S. Patent Application No. 61/196,414, entitled "Sterility Indicating Biological Compositions, Articles and Methods". In some embodiments, the detectable change is an increase in fluorescence of a cell-permeant nucleic acid-interacting fluorescent dye in the presence of nucleic acids present during germination and, optionally, outgrowth of viable spores, as described in U.S. Patent Application No. 61/196,415, entitled, "Biological Compositions, Articles and Methods for Monitoring Sterilization Processes", each of which is incorporated herein by reference.

As shown in FIG. 1, in some embodiments, the detection device 104 can read the biological sterilization indicator 102 in a single-side mode, where the biological sterilization indicator 102 includes a detection window 150 that is positioned adjacent a detection window 151 of the detection device 104, and the detection device 104 can assay the spores and/or detect changes in the spores via the detection window 151. In some embodiments, however, the detection device 104 can include one or more detection windows 151 that are adapted to communicate with one or more detection windows 150 of the biological sterilization indicator 102. For example, in some embodiments, the detection device 104 can assay the spores (e.g., deliver one or more signals to the biological sterilization indicator 102) via a first detection window pair 150, 151, and can detect changes in the spores (e.g., receive one or more signals from the biological sterilization indicator 102) via a second detection window pair 150, 151. In such embodiments, the first detection window pair 150, 151 and the second detection pair 150, 151 can be positioned side-by-side (similar to a single-side mode), or the first detection window pair 150, 151 can be oriented at an angle (e.g., 90 degrees, 180 degrees, etc.) with respect to the second detection window pair 150, 151.

In general, the spores are positioned within the spore reservoir 126 which is in fluid communication with the first reservoir 122. In some embodiments, the spore reservoir 126 forms a portion of the first reservoir 122. As shown in FIG. 2, the first reservoir 122 is in fluid communication with ambience via the sterilant path 132 during sterilization to allow sterilant to enter the first reservoir 122 during a sterilization process to sterilize the spores. The second reservoir 128 is configured to contain the liquid 130 during sterilization to inhibit the liquid 130 from being in fluid communication with the spores, the first reservoir 122, and the sterilant.

In some embodiments, the liquid 130 can include a nutrient medium for the spores, such as a germination medium that will promote germination of surviving spores. In some embodiments, the liquid 130 can include water (or another solvent) that can be combined with nutrients to form a nutrient medium. Suitable nutrients can include nutrients necessary to promote germination and/or growth of surviving spores and may be provided in a dry form (e.g., powdered form, tablet form, caplet form, capsule form, a film or coating, entrapped in a bead or other carrier, another suitable shape or configuration, or a combination thereof) in the first reservoir, and/or positioned near the spore reservoir 126 that will be mixed with (e.g., dissolved in) the water when the water is released from the second reservoir 128. By way of example only, in embodiments in which the nutrient medium is provided in a dry form, the dry form can be present within the first reservoir 122, the spore reservoir 126, on a carrier (described below) for the spores, or a combination thereof. In some embodiments, a combination of liquid and dry nutrient media can be employed.

The nutrient medium is generally selected to induce germination and initial outgrowth of the spores, if viable. The nutrient medium can include one or more sugars, including, but not limited to, glucose, fructose, cellibiose, or the like, or a combination thereof. The nutrient medium can also include a salt, including, but not limited to, potassium chloride, calcium chloride, or the like, or a combination thereof. In some embodiments, the nutrient can further include at least one amino acid, including, but not limited to, at least one of methionine, phenylalanine, and tryptophan.

In some embodiments, the nutrient medium can include indicator molecules, for example, indicator molecules having optical properties that change in response to germination or growth of the spores. Suitable indicator molecules can include, but are not limited to, pH indicator molecules, enzyme substrates, DNA binding dyes, RNA binding dyes, other suitable indicator molecules, or a combination thereof.

Figure 3:
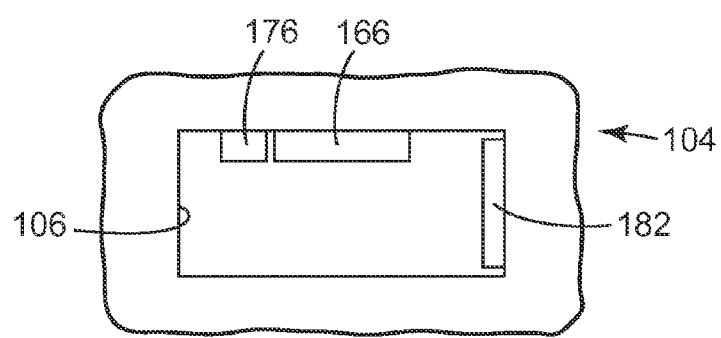
FIG. 3 is a top plan view of the detection device of FIG. 1.
Figure 9:
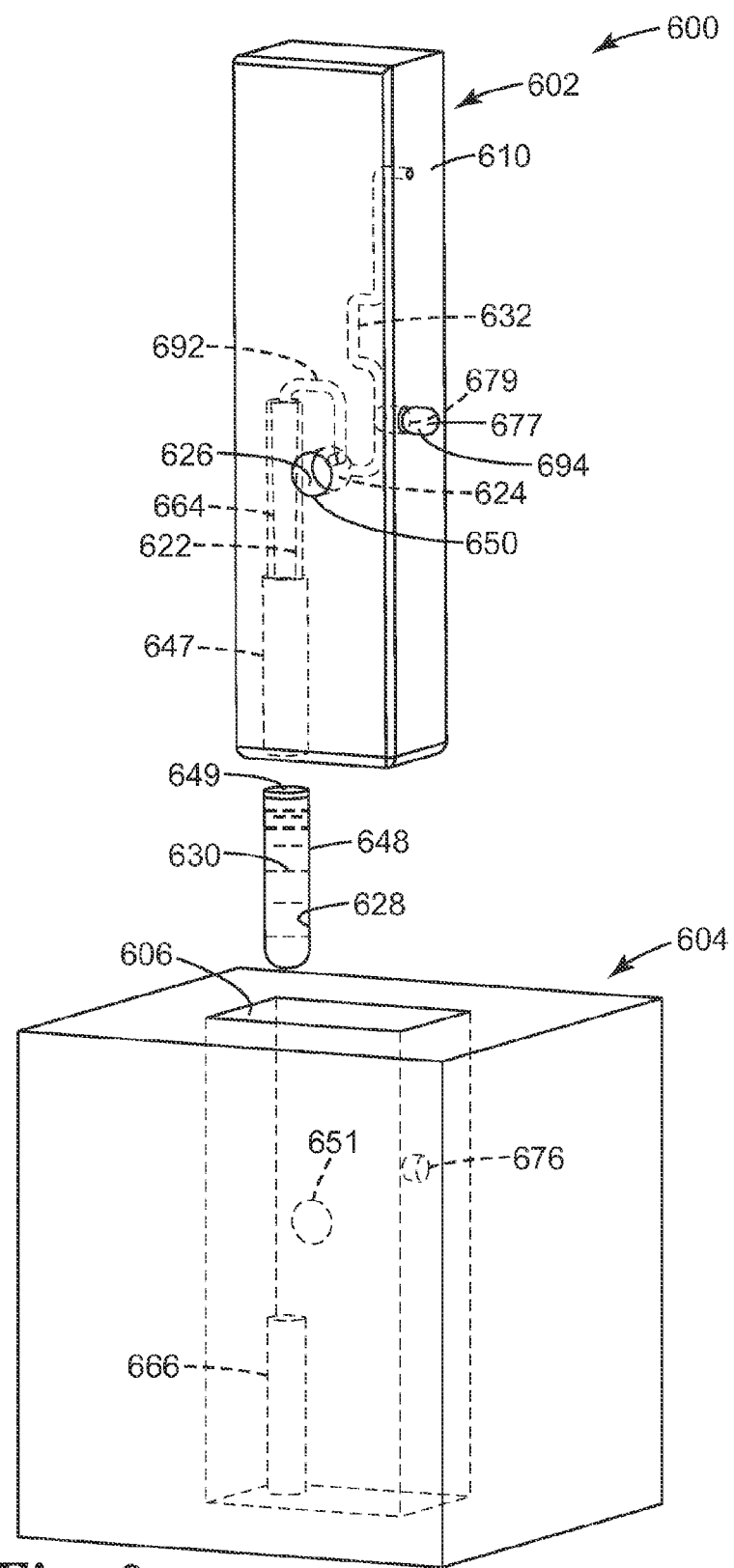
FIG. 9 is a front exploded perspective view of a biological sterilization indicator system according to another embodiment of the present disclosure, the biological sterilization indicator system including a biological sterilization indicator and a detection device.
Figure 10:
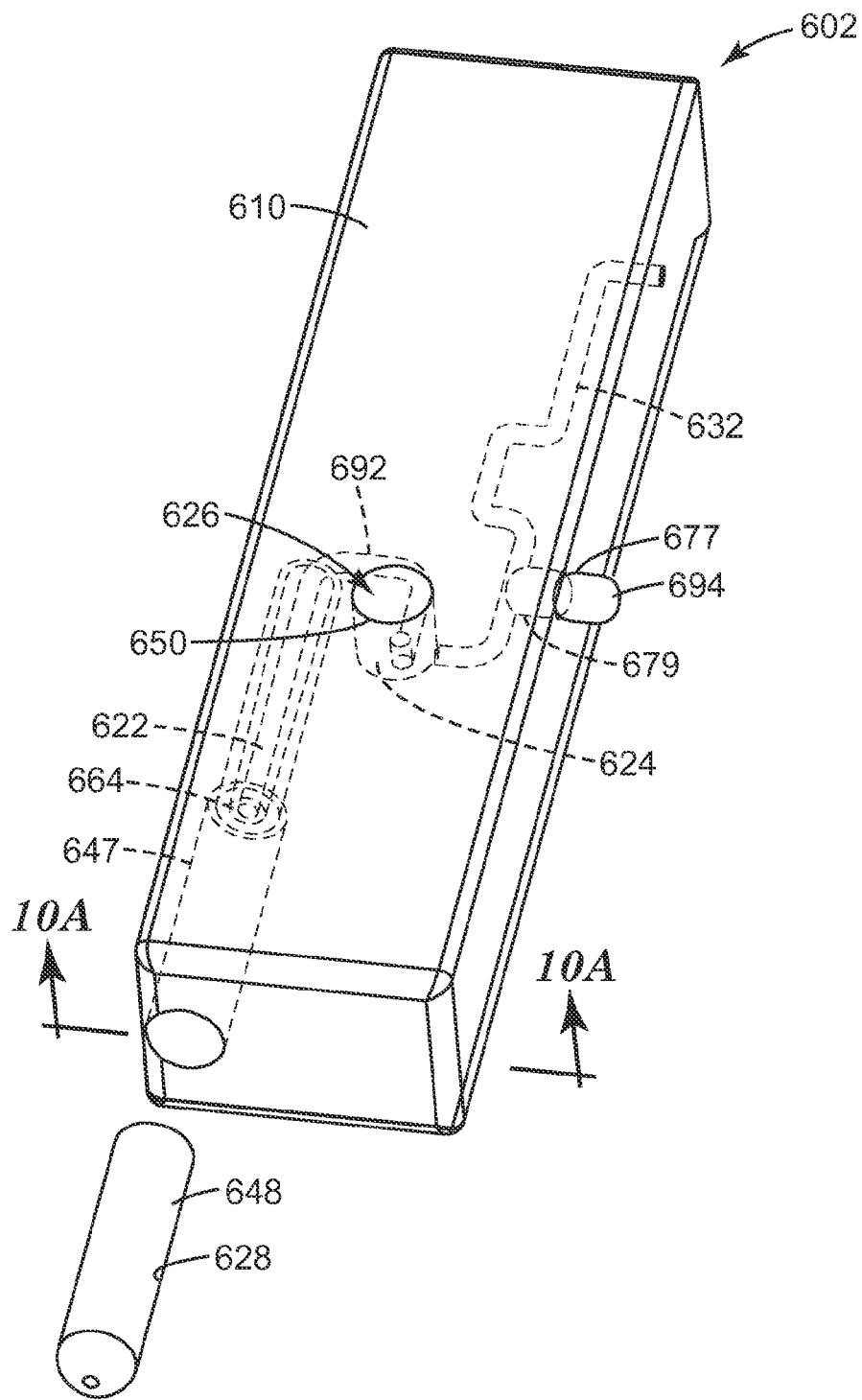
FIG. 10 is a rear partial perspective view of the biological sterilization indicator in FIG. 9.
Figure 14C:
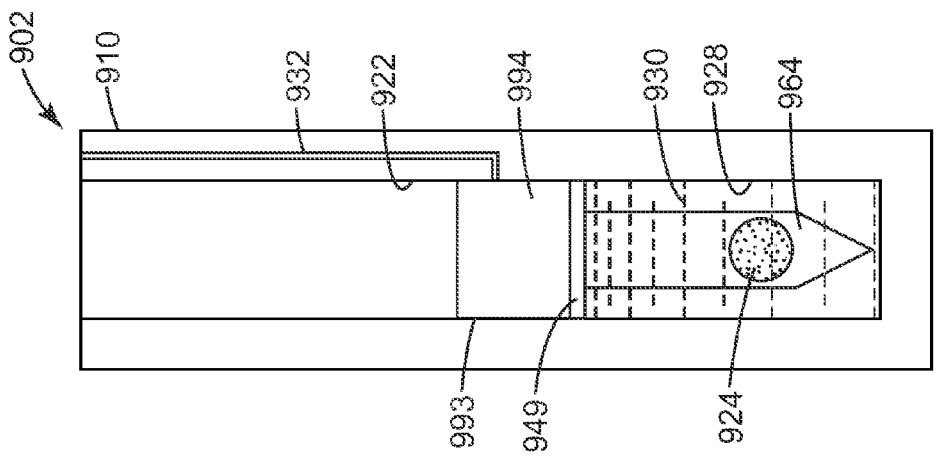
FIGS. 14A-14C are schematic views of a biological sterilization indicator according to another embodiment of the present disclosure.
Figure 14B:
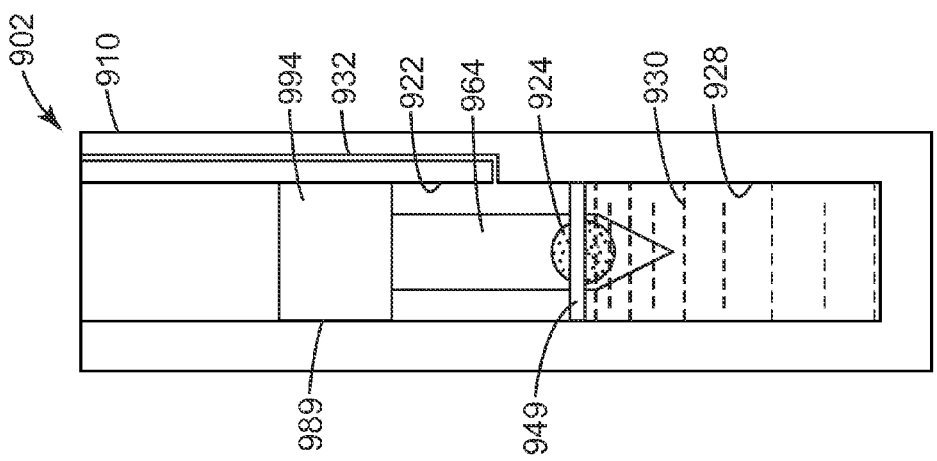
Figure 14A:
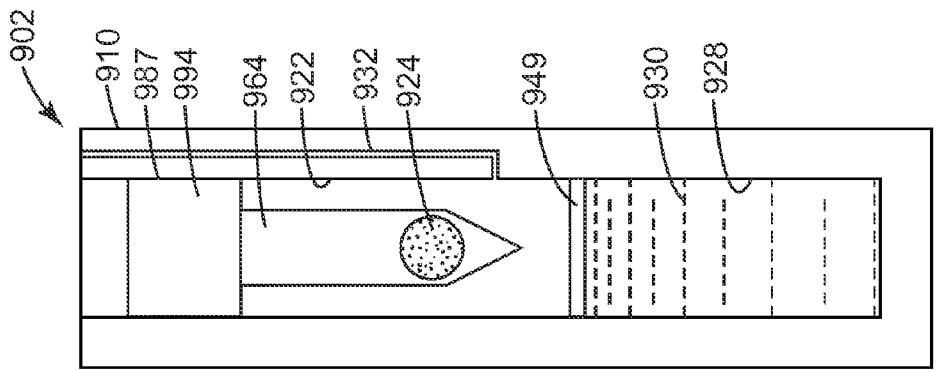

The second reservoir 128 is illustrated in the embodiment illustrated in FIGS. 1-3 as being defined by a frangible container 148. Such a frangible container 148 can be formed of a variety of materials, including, but not limited to, one or more of metal (e.g., foil), a polymer (e.g., any of the polymers listed above with respect to the housing 110), glass (e.g., a glass ampoule), and combinations thereof. In some embodiments, the second reservoir 128 can be defined by other structures, which will be described below with reference to other embodiments and figures. For example, as shown in FIGS. 9-10, in some embodiments, the second reservoir is defined by a container with a frangible cover 649, and as shown in FIGS. 14A-14C, in some embodiments, the second reservoir 128 is defined in a portion of the housing and sealed with a frangible barrier 949.

The spore reservoir 126 is illustrated as being a relatively shallow bore in which the locus 124 of spores can be positioned while remaining adjacent and in fluid communication with the first reservoir 122, such that when the liquid 130 is in the first reservoir 122, the liquid 130 can contact the spores (described greater detail below).

In some embodiments, the first reservoir 122 includes the spore reservoir 126, such that the spore reservoir 126 forms a portion of the first reservoir 122, and in some embodiments, the biological sterilization indicator 102 does not include a separate spore reservoir 126, but rather the locus 124 of spores is positioned on or adjacent an inner surface 152 of the first reservoir 122.

In some embodiments, the locus 124 of spores can be one of a plurality of loci 124 of spores, all of which can be positioned either on or adjacent the inner surface 152 of the first reservoir 122 or in the spore reservoir 126. In some embodiments, having multiple loci 124 of spores can maximize the exposure of the spores to sterilant and to the liquid 130, can improve manufacturing (e.g., placement of the spores can be facilitated by placing each locus 124 of spores in a depression within the biological sterilization indicator 102), and can improve detection characteristics (e.g., because spores in the middle of one large locus 124 of spores may not be as easily detected). In embodiments employing a plurality of loci 124 of spores, each locus 124 of spores can include a different, known number of spores, and/or each locus 124 of spores can include different spores, such that a plurality of spore types can be tested. By employing multiple types of spores, the biological sterilization indicator 102 can be used for a variety of sterilization processes and a specific locus 124 of spores can be analyzed for a specific sterilization process, or the multiple types of spores can be used to further test the effectiveness, or confidence, of a sterilization process.

In addition, in some embodiments, the biological sterilization indicator 102 can include a plurality of spore reservoirs 126, and each spore reservoir 126 can include one or more loci 124 of spores. In some embodiments employing a plurality of spore reservoirs 126, the plurality of spore reservoirs 126 can be positioned in fluid communication with a common reservoir, such as the first reservoir 122 illustrated in FIGS. 2 and 4. In some embodiments, the plurality of spore reservoirs 126 can each be in fluid communication with a common channel that is adapted to be in fluid communication with the liquid 130. An example of an embodiment employing a plurality of spore reservoirs 126 that are in fluid communication with a common channel that is adapted to be in fluid communication with the liquid 130 is illustrated in FIG. 6A and described in greater detail below.

In some embodiments, as shown in FIG. 2, the locus (or loci) 124 of spores can be covered with a cover 154, for example, positioned adjacent the detection window 150. Such a cover 154 can help maintain the spores within the desired locus 124 during manufacturing, sterilization and/or use. The cover 154, if employed, can be formed of a material that does not substantially impede a detection process, and/or which is at least partially light transmissive. In addition, depending on the material makeup of the cover 154, in some embodiments, the cover 154 can facilitate wicking the liquid 130 (e.g., the nutrient medium) along the locus 124 of spores. In some embodiments, the cover 154 can also contain features for facilitating fluid flow into the spore reservoir 126, such as capillary channels, hydrophilic microporous fibers or membranes, or the like, or a combination thereof. In addition, in some embodiments, the cover 154 can isolate a signal, or enhance the signal, which can facilitate detection. Such a cover 154 can be employed whether the locus 124 of spores is positioned within a spore reservoir 126 or on an inner surface 152 of the first reservoir 122. In addition, such a cover 154 can be employed in embodiments employing a plurality of loci 124 of spores. The cover 154 can include a variety of materials, including, but not limited to, paper, a polymer (e.g., any of the polymers listed above with respect to the housing 110), an adhesive (e.g., acrylate, natural or synthetic rubber, silicone, silicone polyurea, isocyanate, epoxy, or combinations thereof), a woven cloth, a nonwoven cloth, a microporous material (e.g., a microporous polymeric material), a glass, a porcelain, a ceramic, a gel-forming material (e.g., guar gum), or combinations thereof.

In some embodiments, the spores can be positioned on a carrier. In some embodiments, the carrier can be positioned in the spore reservoir 126 to support the spores and/or to help maintain the spores in the locus 124 of spores. Such a carrier can include a variety of materials, including, but not limited to, paper, a polymer (e.g., any of the polymers listed above with respect to the housing 110), an adhesive (e.g., acrylate, natural or synthetic rubber, silicone, silicone polyurea, isocyanate, epoxy, or combinations thereof), a woven cloth, a nonwoven cloth, a microporous material (e.g., a microporous polymeric material), a reflective material (e.g., a metal foil), a glass, a porcelain, a ceramic, a gel-forming material (e.g., guar gum), or combinations thereof. In addition, or alternatively, such a carrier can include or be coupled to a hydrophilic coating to facilitate bringing the liquid 130 into intimate contact with the spores (e.g., when the liquid 130 employed is aqueous). In addition, or alternatively, such a hydrophilic coating can be applied to any fluid path positioned to fluidly couple the liquid 130 and the spores. In some embodiments, in addition to, or in lieu of a hydrophilic coating, a hydrophobic coating can be applied to other portions of the inner surface 152 of the first reservoir 122 and/or spore reservoir 126, such that the liquid 130 is preferentially moved into contact with the spores.

As shown in FIG. 2, in some embodiments, the locus 124 of spores can be positioned on or coupled to a front surface 153 (i.e., facing away from the rear wall 116) of the frangible container 148, such that the frangible container 148 includes or is coupled to a spore carrier. In such embodiments, the frangible container 148 can be positioned in the biological sterilization indicator 102, such that when the frangible container 148 is fractured, the liquid 130 can contact the spores, and the front surface 153 of the frangible container 148 can be positioned in an operative position relative to the detection window 150. The shape and configuration of the frangible container 148 is shown by way of example only; however, it should be understood that a variety of shapes and configurations can be employed, and any surface of the frangible container 148 can include or be coupled to a spore carrier.

In some embodiments, the biological sterilization indicator 102 can further include a modified inner surface, such as a reflective surface, a white surface, a black surface, or another surface modification suitable to optimize the optical properties of the surface. A reflective surface (e.g., provided by a metal foil) can be positioned to reflect a signal sent into the spore reservoir 126 from the detection device 104 and/or to reflect any signal generated within the spore reservoir 126 back toward the detection window 150 and to the detection device 104. As a result, the reflective surface can function to improve (e.g., improve the intensity of) a signal from the biological sterilization indicator 102. Such a reflective surface can be provided by the inner surface 152 of the first reservoir 122; a material coupled to the inner surface 152 of the first reservoir 122; an inner surface 156 of the spore reservoir 126; a material coupled to the inner surface 156 of the spore reservoir 126; can form a portion of or be coupled to a spore carrier; or the like; or a combination thereof.

Similarly, in some embodiments, the biological sterilization indicator 102 can further include a white and/or black surface positioned to increase and/or decrease a particular signal sent into the spore reservoir 126 from the detection device 104 and/or to increase and/or decrease a particular signal generated within the spore reservoir 126. By way of example only, a white surface can be used to enhance a signal, and a black surface can be used to reduce a signal (e.g., noise). Such a white and/or black surface can be provided by the inner surface 152 of the first reservoir 122; a material coupled to the inner surface 152 of the first reservoir 122; an inner surface 156 of the spore reservoir 126; a material coupled to the inner surface 156 of the spore reservoir 126; can form a portion of or be coupled to a spore carrier; or the like; or a combination thereof.

In some embodiments, the spores can be positioned on a functionalized surface to promote the immobilization of the spores on the desired surface. For example, such a functionalized surface can be provided by the inner surface 152 of the first reservoir 122, the inner surface 156 of the spore reservoir 126, can form a portion of or be coupled to a spore carrier, can be positioned in any fluid path positioned to fluidly couple the liquid 130 and the spores (e.g., the channel 392 illustrated in FIG. 6 and described below), or the like, or a combination thereof.

In some embodiments, the locus 124 of spores is positioned (e.g. applied by coating or another application method) on a microstructured or microreplicated surface (e.g., such microstructured surfaces as those disclosed in Halverson et al., PCT Publication No. WO 2007/070310, Hanschen et al., US. Publication No. US 2003/0235677, and Graham et al., PCT Publication No. WO 2004/000569, all of which are incorporated herein by reference). For example, such a microstructured surface can be provided by the inner surface 152 of the first reservoir 122, an inner surface 156 of the spore reservoir 126, form a portion of or be coupled to a spore carrier, can be positioned in any fluid path positioned to fluidly couple the liquid 130 and the spores (e.g., the channel 392 illustrated in FIG. 6 and described below), or the like, or a combination thereof.

In some embodiments, the biological sterilization indicator 102 can further include a gel-forming material positioned to be combined with the spores and the liquid 130 when the liquid 130 is released from the second reservoir 128. For example, the gel-forming material can be positioned at the locus 124 of spores, in the first reservoir 122, in the spore reservoir 126, can form a portion of or be coupled to a spore carrier, can be positioned in any fluid path positioned to fluidly couple the liquid 130 and the spores (e.g., the channel 392 illustrated in FIG. 6 and described below), or the like, or a combination thereof. Such a gel-forming material can form a gel (e.g., a hydrogel) or a matrix comprising the spores and nutrients when the liquid 130 comes into contact with the spores. A gel-forming material (e.g., guar gum) can be particularly useful because it has the ability to form a gel upon hydration, it can aid in localizing a signal (e.g., fluorescence), it can anchor the spores in place, it can help minimize diffusion of the spores and/or a signal from the spore reservoir 126, and it can enhance detection.

In some embodiments, the biological sterilization indicator 102 can further include an absorbent or a wicking material. For example, the wicking material can be positioned at the locus 124 of spores, in the first reservoir 122, in the spore reservoir 126, can form at least a portion of or be coupled to a spore carrier, can be positioned in any fluid path positioned to fluidly couple the liquid 130 and the spores (e.g., the channel 392 illustrated in FIG. 6 and described below), or the like, or a combination thereof. Such a wicking material can include a porous wicking pad, a soaking pad, or the like, or a combination thereof, to facilitate bringing the liquid 130 into intimate contact with the spores.

As mentioned above, the frangible container 148 defines the second reservoir 128 and contains the liquid 130. The frangible container 148 is positioned in the first reservoir 122 of the housing 110. With reference to FIG. 2, the rear wall 116 of the housing 110 adjacent the first reservoir 122 is deformable to allow at least a portion of the rear wall 116 to be deformed. For example, as shown in the embodiment illustrated in FIGS. 1-4, the rear wall 116 can include one or more slots 158 to form a first movable member 160. The movable member 160 can include at least a portion of the rear wall 116 and can be, at least temporarily, deflected out of the plane of the remainder of the rear wall 116. For example, the movable member 160 can be moved from a first position where the movable member 160 lies in the plane of the rear wall 116 to a second position where the movable member 160 is oriented at an angle (i.e., a nonzero angle) with respect to the rear wall 116. That is, the movable member 160 can be pivotally movable about axis A-A, as shown in FIG. 2. FIG. 2 illustrates one example of a configuration of a deformable rear wall 116.

However, as can be appreciated by one of ordinary skill in the art, a variety of rear wall configurations can be employed to allow at least a portion of the rear wall 116, particularly, the portion adjacent the first reservoir 122, to be deformable. For example, in some embodiments, the rear wall 116 can include a deformable portion, such as by forming at least a portion of the rear wall 116 of a deformable material (e.g., an elastomeric material); by making the rear wall 116 thin enough to be deflected; by have a deformable shape (e.g., a dome shape that inverts and compresses the frangible container 148 when pressed); or the like; or combinations thereof.

Figure 4:
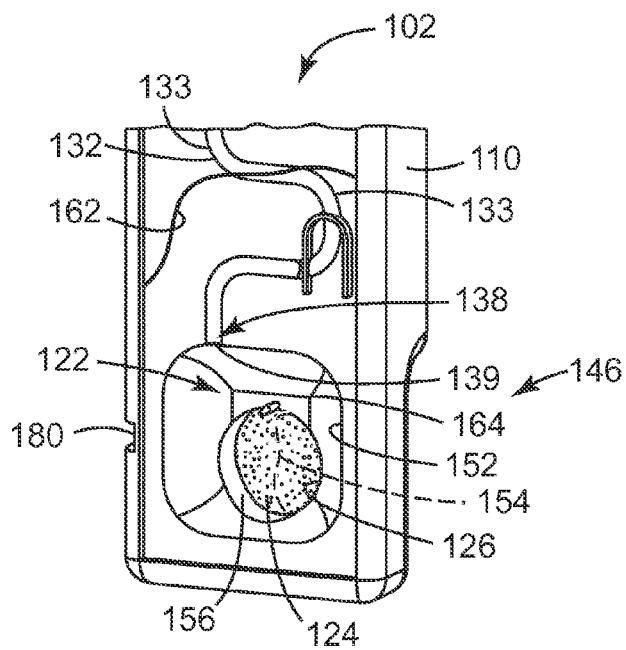
FIG. 4 is a rear partial perspective view of the biological sterilization indicator of FIGS. 1 and 2, with portions removed for clarity.

As shown in FIGS. 2 and 4, the biological sterilization indicator 102 can further include a cover 162 to seal (e.g., hermetically seal) the interior of the housing 110 from ambience. Such a cover 162 can be formed of a variety of materials, including, but not limited to, a metal, a polymer, an elastomer, or a combination thereof. For example, in some embodiments, the cover 162 can be a thin film. In some embodiments, the cover 162 can be formed of the same material as the rear wall 116. The cover 162 can be positioned internally or externally (i.e., forwardly or rearwardly) with respect to the rear wall 116 of the housing 110, and the cover 162 can also be liquid impermeable.

As shown in FIG. 2, when the biological sterilization indicator 102 is assembled, the deformable portion of the rear wall 116 is positioned adjacent the first reservoir 122, but is also positioned adjacent the frangible container 148 that defines the second reservoir 128 and contains the liquid 130. By employing a deformable rear wall 116, when the rear wall 116 adjacent the first reservoir 122 is deformed, the frangible container 148 can be compressed or pushed against another object within the first reservoir 122 to cause the frangible container 148 to break, dispelling the liquid 130 into the first reservoir 122 and into contact with the spores.

For example, in some embodiments, as shown in the embodiment illustrated in FIGS. 1-4, the biological sterilization indicator 102 can include a fracturing member 164 positioned to fracture the frangible container 148 when the rear wall 116 is deformed or depressed. Particularly, the fracturing member 164 is illustrated in FIGS. 2 and 4 as including a sharp end that is positioned to pierce the frangible container 148, such that the fracturing member 164 is a piercing member. By way of example only, in the embodiment illustrated in FIGS. 2 and 4, the fracturing member 164 can be held a distance from the frangible container 148 until the frangible container 148 is pressed into contact with the fracturing member 164, to avoid having the frangible container 148 prematurely contact the fracturing member 164 and prematurely release the liquid 130. That is, the frangible container 148 can be coupled to the movable member 160, such that the frangible container 148 does not contact the fracturing member 164 until the movable member 160 is moved.

Other suitable configurations can be employed to inhibit premature contact between the frangible container 148 and the fracturing member 164. For example, in some embodiments, the fracturing member 164 can be positioned in a recessed position relative to an inner wall of the housing 110 that defines the first reservoir 122, such that the fracturing member 164 is inhibited from prematurely contacting the frangible container 148. In some embodiments, the fracturing member 164 can include or be used in combination with a protective barrier or shroud that can be movable between a first position in which the protective barrier is positioned between the fracturing member 164 and the frangible container 148 and a second position in which the protective barrier is not positioned between the fracturing member 164 and the frangible container 148 and the fracturing member 164 is positioned to contact the frangible container 148. In some embodiments, the fracturing member 164 itself can be movable from a first position in which the fracturing member 164 is protected by a barrier (e.g., is recessed relative to an inner wall of the housing 110 that defines the first reservoir 122) to a second position in which the fracturing member 164 is not protected by a barrier and is positioned to contact the frangible container 148.

However, in some embodiments, the fracturing member 164 includes a blunt object, a rigid surface, a hammer, or a combination thereof, that aids in fracturing and/or compressing the frangible container 148. For example, the fracturing member 164 can include a blunt object that compresses the frangible container 148, or against which the frangible container 148 is pressed, until the pressure within the second reservoir 128 exceeds that which can be withheld by the frangible container 148, such that the frangible container 148 fractures.

In some embodiments, the frangible container 148 can be configured to facilitate fracturing of the frangible container 148 in a desired manner. For example, in some embodiments, the front surface 153 of the frangible container 148 can be formed of a thinner and/or weaker material, such that the front surface 153 preferentially fractures over another surface of the frangible container 148. In addition, in some embodiments, the frangible container 148 can include a variety of features positioned to facilitate fracturing of the frangible container 148 is a desired manner, including, but not limited to, a thin and/or weakened area, a score line, a perforation, or the like, or combinations thereof.

As a result, the frangible container 148 and the second reservoir 128 have a first closed state in which the liquid 130 is contained within the frangible container 148 and the second reservoir 128 and a second open state in which the frangible container 148 has fractured and the liquid 130 is allowed to exit the second reservoir 128 into the first reservoir 122.

As shown in FIGS. 1 and 3, the detection device 104 can include a first actuator 166 that is positioned within the recess 106, such that as the biological sterilization indicator 102 is positioned within the recess 106, the actuator 166 deforms the deformable portion of the rear wall 116, and particularly, in the embodiment illustrated in FIGS. 1-4, such that the actuator 166 actuates the movable member 160 to move inwardly (i.e., forwardly with respect to the biological sterilization indicator 102) to cause the frangible container 148 to be punctured by the fracturing member 164. Such a configuration allows the detection device 104 to actuate combining the liquid 130 and the spores, such that the liquid 130 and the spores are not in fluid communication until the biological sterilization indicator 102 is positioned in the recess 106 of the detection device 104. This would not always need to be the case, but can offer some unique advantages in some embodiments of the present disclosure.

The actuator 166 is shown in FIG. 1 as including a protrusion positioned to actuate the movable member 160 to move between a first position in which the frangible container 148 is intact and the frangible container 148 and the second reservoir 128 defined by the frangible container 148 are in a closed state, and a second position in which the frangible container 148 and the second reservoir 128 are in an open state. However, the protrusion is shown by way of example only, and it should be understood that the actuator 166 can take on a variety of forms or configurations. For example, in some embodiments, the actuator 166 can include a laser that emits a laser beam adapted to fracture the frangible container 148, or, in embodiments in which the liquid 130 is positioned in a reservoir that is sealed from the spore reservoir 126, the laser beam can open a barrier or a valve (e.g., "laser valving") to allow fluid communication between the reservoir containing the liquid 130 and the spore reservoir 126.

One or both of the biological sterilization indicator 102 and the detection device 104 can be further configured to inhibit premature or accidental fracturing of the frangible container 148. For example, in some embodiments, the biological sterilization indicator 102 can include a lock or locking mechanism that is positioned to inhibit the frangible container 148 from being prematurely fractured. In such embodiments, the detection device 104 can include a "key" positioned to "unlock" the lock of the biological sterilization indicator 102, such that the frangible container 148 can be fractured, for example, when the detection device 104 is coupled to the biological sterilization indicator 102. By way of example only, in some embodiments, the biological sterilization indicator 102 can include a door or other structure positioned adjacent or over the movable member 160 that inhibits the movable member 160 from being moved (and accordingly, inhibits the frangible container 148 from being fractured) when the biological sterilization indicator 102 is handled (e.g., prior to being coupled to the detection device 104). In such an embodiment, the detection device 104 can include an actuator positioned to move the door away from the movable member 160 to allow the movable member 160 to be moved. In some embodiments, the first actuator 166 (or a second actuator 176, described below) is further configured to unlock the biological sterilization indicator 102, and in some embodiments, an additional actuator is employed to perform this function. It should be understood that a variety of coupling means and cooperating structures can be employed as the lock and key to inhibit premature fracturing of the frangible container 148.

With reference to FIGS. 2 and 4, the sterilant path 132 is shown as having several bends or curves 133. Such a configuration can control the delivery rate of a sterilant to the first reservoir 122, and ultimately, to the locus 124 of spores. The configuration shown in FIGS. 2 and 4 is shown by way of example, but the delivery rate of the sterilant can be controlled using a variety of sterilant path configurations. For example, in some embodiments, the sterilant path 132 does not include the bends 133, but rather is substantially linear or straight from an inlet (e.g., inlet 134), to its outlet 138, and one or more of its diameter, cross-sectional shape, cross-sectional area, length, or the like, is used to control the sterilant delivery rate. For example, in some embodiments, the aspect ratio of the cross-sectional area of the sterilant path 132 (e.g., at the outlet 138 of the sterilant path 132 or along the entire length of the sterilant path 132) to the volume of the first reservoir 122 or to the volume of the spore reservoir 126 can be controlled to achieve the desired delivery rate, in addition to, or as an alternative to, employing the bends 133 in the sterilant path 132.

In some embodiments, the first reservoir 122 has a volume of at least about 5 microliters, in some embodiments, at least about 20 microliters, and in some embodiments, at least about 35 microliters. In some embodiments, the first reservoir 122 has a volume of no greater than about 3000 microliters (i.e., 3 mL), in some embodiments, no greater than about 1500 microliters, and in some embodiments, no greater than about 100 microliters.

In some embodiments, the spore reservoir 126 has a volume of at least about 5 microliters, in some embodiments, at least about 20 microliters, and in some embodiments, at least about 35 microliters. In some embodiments, the spore reservoir 126 has a volume of no greater than about 250 microliters, in some embodiments, no greater than about 175 microliters, and in some embodiments, no greater than about 100.

In some embodiments, the second reservoir 128 (e.g., the volume within the frangible container 148 that holds the liquid 130) has a volume of at least about 5 microliters, in some embodiments, at least about 20 microliters, and in some embodiments, at least about 35 microliters. In some embodiments, the second reservoir 128 has a volume of no greater than about 2000 microliters (i.e., 2 mL), in some embodiments, no greater than about 1000 microliters, and in some embodiments, no greater than about 100 microliters.

In some embodiments, the volume of the liquid 130 contained in the second reservoir 128 is at least about 5 microliters, in some embodiments, at least about 20 microliters, and in some embodiments, at least about 35 microliters. In some embodiments, the volume of the liquid 130 contained in the second reservoir 128 is no greater than about 1000 microliters (i.e., 1 mL), in some embodiments, no greater than about 500 microliters, and in some embodiments, no greater than about 100 microliters.

In some embodiments, the volume of the liquid 130 delivered to the spore reservoir 126 (or the first reservoir 122) is at least about 1 microliter, in some embodiments, at least about 20 microliters, and in some embodiments, at least about 35 microliters. In some embodiments, the volume of the liquid 130 delivered to the spore reservoir 126 is no greater than about 1000 microliters (i.e., 1 mL), in some embodiments, no greater than about 500 microliters and in some embodiments, no greater than about 100 microliters.

In some embodiments, the sterilant path 132 serves several functions in the biological sterilization indicator 102. For example, the sterilant path 132 can provide a path for delivering a sterilant to the spores, and the sterilant path 132 can, in addition, provide a vent to the biological sterilization indicator 102. For example, in the embodiment illustrated in FIGS. 1-4, when the frangible container 148 is in its closed state, the sterilant path 132 is in fluid communication with the first reservoir 122, the spore reservoir 126 and the locus 124 of spores. When the frangible container 148 is punctured and in its open state, the second reservoir 128 and the liquid 130 are in fluid communication with the first reservoir 122, the spore reservoir 126, the locus 124 of spores, and the sterilant path 132. The fluid communication between the sterilant path 132 and the first reservoir 122/spore reservoir 126 allows air to escape, or vent, out of the biological sterilization indicator 102 via the sterilant path 132 when the frangible container 148 is opened, such that air in the first reservoir 122 can be displaced by and/or replaced with the liquid 130.

However, because the biological sterilization indicator 102 employs a relatively small volume of liquid 130 and such a small volume is sensitive to evaporation, the sterilant path 132 can also provide a path for evaporation of the liquid 130 after the frangible container 148 has been opened. As a result, one or both of the biological sterilization indicator 102 and the detection device 104 can include means for inhibiting evaporation of the liquid 130 when the frangible container 148/second reservoir 128 is in its open state. Said another way, one or both of the biological sterilization indicator 102 and the detection device 104 can include means for inhibiting fluid communication between the first reservoir 122 and ambience when the frangible container 148/second reservoir 128 is in its open state. In the embodiment illustrated in FIGS. 1-4, a portion of the rear wall 116 of the housing 110 adjacent a portion of the sterilant path 132 is deformable to allow at least a portion of the rear wall 116 to be deformed to substantially seal (e.g., hermetically seal) the sterilant path 132 and to fluidly decouple the first reservoir 122 from ambience. Sealing the sterilant path 132 can inhibit evaporation of the liquid 130 and can also inhibit contamination by foreign organisms, objects or materials (e.g., debris) from entering the interior of the biological sterilization indicator 102 and the first reservoir 122.

For example, as shown in FIG. 2, the rear wall 116 can include one or more slots 168 to form a second movable member 170. The movable member 170 can include at least a portion of the rear wall 116 and can be, at least temporarily, deflected out of the plane of the remainder of the rear wall 116. For example, the movable member 170 can be moved from a first position where the movable member 170 lies in the plane of the rear wall 116 to a second position where the movable member 170 is oriented at an angle (i.e., a nonzero angle) with respect to the rear wall 116. That is, the movable member 170 can be pivotally movable about axis B-B, as shown in FIG. 2. FIG. 2 illustrates one example of a configuration of a deformable rear wall 116 adjacent the sterilant path 132. However, as can be appreciated by one of ordinary skill in the art, a variety of rear wall configurations can be employed to allow at least a portion of the rear wall 116, particularly, a portion adjacent the sterilant path 132, to be deformable.

As shown in FIGS. 2 and 4, the same cover 162 over the portion of the rear wall 116 adjacent the movable member 160 can be employed over the portion of the rear wall 116 adjacent the movable member 170, or, in some embodiments, a different cover can be employed.

In some embodiments, the cover 162 can be positioned internally (i.e., forwardly with respect to the biological sterilization indicator 102), and the cover 162 can be formed of a polymeric or metal film that can be pressed into the sterilant path 132 by the movable member 170, substantially sealing off the sterilant path 132 at a point adjacent the movable member 170. Such a sealing method can be referred to as "staking" or employing a "deformable seal," which is described in greater detail in Dufresne, et al., U.S. Pat. No. 7,507,376, entitled "Integrated Sample Processing Devices;" Bedingham, et al., U.S. Pat. No. 7,595,200, entitled "Sample Processing Devices and Carriers;" Bedingham, et al., U.S. Pat. No. 7,026,168, entitled "Sample Processing Devices;" and Harms, et al., U.S. Pat. No. 6,814,935, entitled "Sample Processing Devices and Carriers;" each of which is incorporated herein by reference. In embodiments employing a staking method for sealing the sterilant path 132, at least a portion of the sterilant path 132 can include an adhesive that is positioned to adhere to the cover 162, or a deformable portion of the rear wall 116 when the movable member 170 is depressed.

As shown in FIGS. 1 and 3, the detection device 104 can include a second actuator 176 that is positioned within the recess 106, such that as the biological sterilization indicator 102 is positioned within the recess 106, the actuator 176 deforms the deformable portion of the rear wall 116, and particularly, in the embodiment illustrated in FIGS. 1-4, such that the actuator 176 actuates the second movable member 170 to move inwardly (i.e., forwardly with respect to the biological sterilization indicator 102) to seal the sterilant path 132. Such a configuration allows the detection device 104 to actuate sealing the sterilant path 132, such that the first reservoir 122 is no longer in fluid communication with ambience, and such that the liquid 130 cannot escape from the biological sterilization indicator 102 via the sterilant path 132 after the frangible container 148 has been opened. In the embodiment illustrated in FIGS. 1-4, the biological sterilization indicator 102 can be moved relative to the recess 106 of the detection device 104 to a first position 173 in the recess 106 (shown in FIG. 1 in phantom lines) in which the first actuator 166 actuates the first movable member 160 to break the frangible container 148 and release the liquid 130 into the first reservoir 122 and into contact with the spores; and the biological sterilization indicator 102 can be moved to a second position 175 in the recess 106 (shown in FIG. 1 in solid lines) in which the second actuator 176 actuates the second movable member 170 to seal the sterilant path 132.

In some embodiments, the first position 173 and the second position 175 can be the same, or can be very near one another such that no time delay, or a very small time delay, exists between the first position 173 and the second position 175. In some embodiments, the first and second positions occur in quick succession, and the biological sterilization indicator 102 can be positioned in the recess 106 by moving the biological sterilization indicator 102 substantially along the longitudinal direction of the recess 106 at a somewhat constant rate, without stopping or pausing at the first or second position, until the biological sterilization indicator 102 has reached a final position in the recess 106 (which may or may not include one of the first and second positions 173, 175).

The actuator 176 is shown in FIG. 1 as including a protrusion positioned to actuate the movable member 170 to move between a first position in which the sterilant path 132 is not obstructed and the first reservoir 122 is in fluid communication with ambience via the sterilant path 132 and a second position in which the sterilant path 132 is obstructed and the first reservoir 122 is not in fluid communication with ambience via the sterilant path 132. However, the protrusion is shown by way of example only, and it should be understood that the actuator 176 can take on a variety of forms or configurations. For example, in some embodiments, the actuator 176 can include a different structure positioned to actuate the movable member 170. By way of further example, in some embodiments, the biological sterilization indicator 102 does not necessarily include the movable member 170, and the actuator 176 can include a laser that emits a laser beam adapted to form a seal in the sterilant path 132 (e.g., by melting a material or structure to cause it to flow into and block the sterilant path 132).

In some embodiments, more than one sterilant path 132 can be employed. For example, in some embodiments, a plurality of sterilant paths 132 can be employed in parallel to fluidly couple the first reservoir 122 with ambience. The plurality of sterilant paths 132 can be used as a whole (i.e., all at once) or selectively to achieve the desired sterilant delivery rate.

In addition, or alternatively, in some embodiments, more than one sterilant path 132 can be employed in series, such that one or more first sterilant paths 132 provide a fluid path from ambience to the first reservoir 122, and one or more second sterilant paths 132 provide a fluid path from the first reservoir 122 to ambience, such that sterilant can move from ambience, through the one or more first sterilant paths 132, into the first reservoir 122, and out the one or more second sterilant paths 132, back out to ambience. In such embodiments, both the first sterilant path(s) 132 and the second sterilant path(s) 132 can be sealed (e.g., via the sealing mechanisms described above) to protect the contents of the first reservoir 122 from evaporation and from introduction of contaminating or foreign organisms, objects or materials.

In some embodiments, as shown in FIGS. 1-4, the detection window 150, the locus 124 of spores, and the spore reservoir 126 can be substantially planar, the locus 124 of spores can be positioned directly adjacent the detection window 150, and the detection window 150 can be sized such that at least one dimension of the detection window 150 substantially matches at least one dimension of the spore reservoir 126 and/or the locus 124 of spores. Said another way, the detection window 150 can include a cross-sectional area that is substantially the same size as the cross-sectional area of the spore reservoir 126 and/or the locus 124 of spores. Such size matching between the detection window 150 and the spore reservoir 126 and/or the locus 124 of spores can maximize the signal detected by the detection device 104 from the biological sterilization indicator 102. Alternatively, or in addition, the detection window 150 can be sized to match the first reservoir 122 (e.g., at least one dimension or the cross-sectional areas can be sized to match), and/or the detection window 151 of the detection device 104 (see FIG. 1). Such size matching between detection zones, both in the biological sterilization indicator 102 and the detection device 104 can improve spore assaying and detection, such that substantially all of the signal from the spores can be detected.

The biological sterilization indicator 102 illustrated in FIGS. 1-4 is substantially flat and planar, and at least the portion of the biological sterilization indicator 102 where the locus 124 of spores, the spore reservoir 126 and the detection window 150 are positioned is relatively small, such that small volumes of the spores and/or the liquid 130 can be used to achieve a rapid, efficient and effective result. For example, in some embodiments, the small volumes can facilitate detection because there is less volume to interrogate, which can facilitate the speed and efficacy of detection. In some embodiments, the small volumes lead to an increased concentration of spores and/or signals, which can facilitate detection, for example, even with a less robust or sensitive detection device.

In addition, at least the portion of the biological sterilization indicator 102 wherein the locus 124 of spores, the spore reservoir 126 and the detection window 150 is relatively thin (i.e., the "z dimension" is minimized), such that the optical path from the spores to the detection window 150 is minimized and/or any effect of interfering substances in the liquid 130 (or nutrient medium) is minimized. In addition, due at least partially to the concentration of the spores into the locus 124 of spores that is directly adjacent the detection window 150, substantially all of a signal generated by the spores can be detected by the detection device 104, such that substantially no signal is lost. That is, in some embodiments, for example, substantially no signal is lost because the biological sterilization indicator system 100 does not include any excessively long optical path and/or because little to none of the liquid 130 and spore mixture resides outside of the optical path of the system.

In some embodiments, the concentration of spores (and/or a signal) and/or a change in the concentration can be detected by the detection device 104. For example, in some embodiments, an increase in the concentration of spores and/or a signal indicative of spore viability or growth can be detected by the detection device 104 to assess spore viability.

Figure 6:
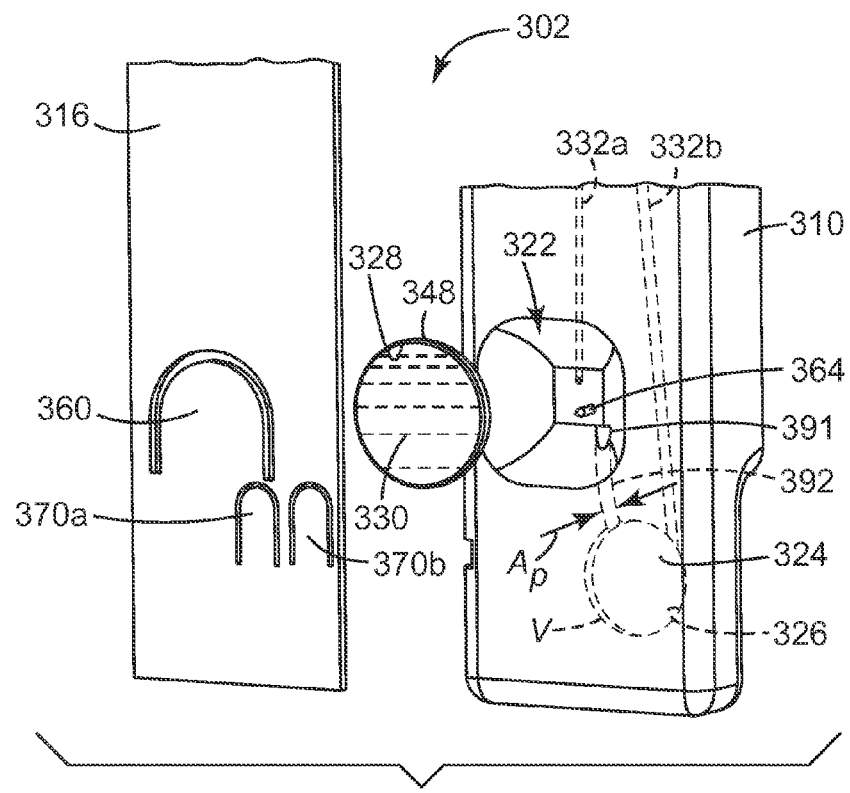
FIG. 6 is a rear exploded partial perspective view of a biological sterilization indicator according to another embodiment of the present disclosure.
Figure 6A:
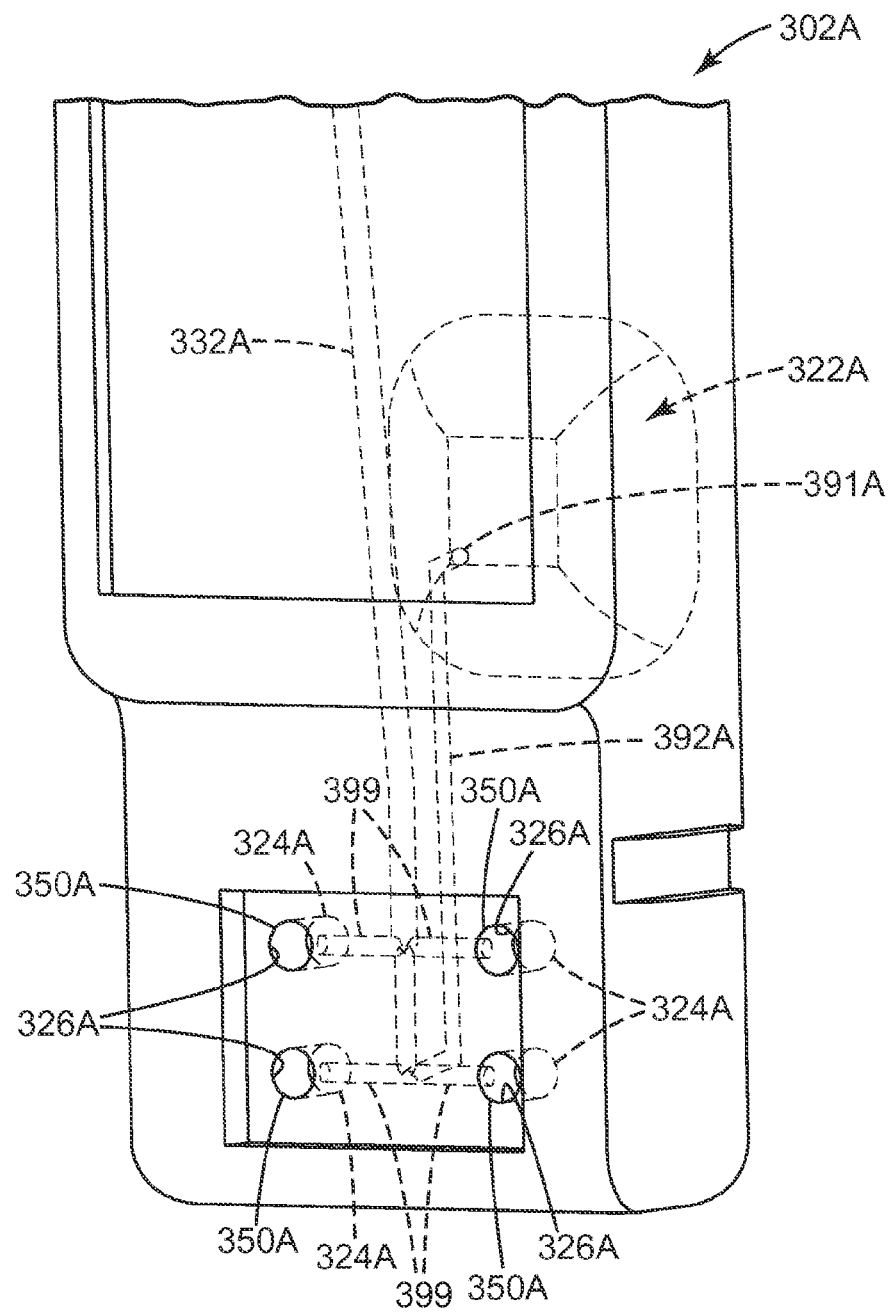
FIG. 6A is a front partial perspective view of a biological sterilization indicator according to another embodiment of the present disclosure.

Furthermore, diffusion of spores, spores combined with the liquid 130, and/or a signal from the spores out of the first reservoir 122 (i.e., and away from the detection window 150) can be minimized by ensuring that any fluid path (e.g., the sterilant path 132, a channel opening into the first reservoir 122 through which the liquid 130 may be introduced, see, for example, FIG. 6) that is fluidly connected to the first reservoir 122 or the spore reservoir 126 has an aspect ratio relative to the first reservoir 122 or the spore reservoir 126 that minimizes diffusion (fluid movement) from the first reservoir 122 or the spore reservoir 126 into the fluid path.

For example, in some embodiments, the ratio of the cross-sectional area of the fluid path ($A_p$) (e.g., at the outlet 138 of the sterilant path 132) to the volume (V) of the reservoir (e.g., the first reservoir 122 or the spore reservoir 126) from which fluid may move into the fluid path, i.e., $A_p$:V, can range from about 1:25 to about 1:500, in some embodiments, can range from about 1:50 to about 1:300, and in some embodiments, can range from about 1:100 to about 1:200. Said another way, in some embodiments, the fraction of $A_p/V$ can be at least about 0.01, in some embodiments, at least about 0.02, and in some embodiments, at least about 0.04. In some embodiments, the fraction of $A_p/V$ can be no greater than about 0.005, in some embodiments, no greater than about 0.003, and in some embodiments, no greater than about 0.002.

Reported in yet another way, in some embodiments, the fraction of $V/A_p$, or the ratio of V to $A_p$, can be at least about 25 (i.e., 25 to 1), in some embodiments, at least about 50 (i.e., about 50 to 1), and in some embodiments, at least about 100 (i.e., about 100 to 1). In some embodiments, the fraction of $V/A_p$, or the ratio of V to $A_p$, can be no greater than about 500 (i.e., about 500 to 1), in some embodiments, no greater than about 300 (i.e., about 300 to 1), and in some embodiments, no greater than about 200 (i.e., about 200 to 1).

As a result of one or more of the mechanisms and features described herein for enhancing detection, the biological sterilization indicator 102 and/or the detection device 104 can be configured such that substantially all detectable changes from the spores can be detected. For example, in situations where optical properties of the spores are assayed, substantially all detectable changes in the optical property in question can be detected. Such efficiency can be achieved by one or more of the mechanisms or features described herein, including, but not limited to, size matching between one or more of the detection window 150 of the biological sterilization indicator 102, the detection window 151 of the detection device 104, a dimension of the first reservoir 122, a dimension of the locus 124 of spores, a dimension of the spore reservoir 126, or combinations thereof; providing a reflective, white and/or black surface; reducing the total volume of liquid 130 that is delivered to the spores; providing the necessary aspect ratios of the cross-sectional area of a channel positioned in fluid communication with the spore reservoir 126 or the first reservoir 122 to the volume of the spore reservoir 126 or the first reservoir, respectively; minimizing the "z dimension"; minimizing the overall size of the spore reservoir 126; or the like; or combinations thereof.

As shown in FIG. 2, the biological sterilization indicator 102 can include a protrusion 178 adjacent the inlet 134 (or the inlet 135) of the sterilant path 132 to inhibit the inlet 134 from becoming blocked during sterilization, for example, if the biological sterilization indicator 102 were to be positioned against another object or laid down upon its rear wall 116 during sterilization. The protrusion 178 can be a portion of the housing 110 of the biological sterilization indicator 102 (e.g., a portion of the rear wall 116), or the protrusion 178 can be coupled to the housing 110.

As shown in FIGS. 1, 3 and 4, the biological sterilization indicator 102 can further include an orientation feature 180 that cooperates with an orientation feature 182 of the detection device 104. Particularly, the orientation feature 180 can cooperate with an orientation feature 182 (see FIGS. 1 and 3) within the recess 106 of the detection device 104. The orientation features 180, 182 can provide feedback that the biological sterilization indicator 102 has reached a desired position in the detection device 104. In addition, the orientation features 180, 182 can be used to ensure that the biological sterilization indicator 102 can only be coupled to the detection device 104 in one orientation. By way of example only, the orientation feature 180 is shown as including a recess formed in the housing 110 of the biological sterilization indicator 102, and the orientation feature 182 of the detection device 104 is shown as including a protrusion dimensioned to fit in the recess of the biological sterilization indicator 102. As a result, when the biological sterilization indicator 102 has reached a desired position (e.g., the first position 173 or the second position 175), the orientation feature 182 of the detection device 104 and the orientation feature 180 of the biological sterilization indicator 102 engage. Such an engagement can include a variety of snap-fit engagements, detents, cams, or the like, or combinations thereof. In addition, a plurality of orientation features associated with each desired position of the biological sterilization indicator 102 in the detection device 104 can be employed. Furthermore, a variety of suitable orientation features 180, 182 that are capable of cooperating and/or engaging in order to provide feedback regarding the position of the biological sterilization indicator 102 with respect to the detection device 104 can be employed and the present disclosure is not limited to the orientation features 180, 182 illustrated in FIGS. 3 and 4.

In some embodiments, the biological sterilization indicator 102 can further include an identification feature 184, such as a barcode, a radio-frequency identification (RFID), or the like. Furthermore, in some embodiments, the biological sterilization indicator 102 can include a chemical indicator 186. Such a chemical indicator 186 can indicate whether the biological sterilization indicator 102 has been exposed to sterilizing conditions. For example, the chemical indicator 186 can have a first state, indicating that the biological sterilization indicator 102 has not been exposed to sterilizing conditions and a second state, indicating that the biological sterilization indicator 102 has been exposed to sterilizing conditions. A variety of chemical indicators can be employed, including, but not limited to, those described in Hehenberger, et al, U.S. Pat. No. 6,534,006, entitled "Chemical Indicator for Determining the Adequacy of a Liquid Sterilization Process," and Read, U.S. Pat. No. 7,192,554, entitled "Hydrogen Peroxide and Peracetic Acid Indicators and Methods," both of which are incorporated herein by reference.

In use, the biological sterilization indicator 102 is placed along with a sterilizing batch for a sterilization process. During sterilization, the sterilant path 132 is in fluid communication with the first reservoir 122, the spore reservoir 126, and the locus 124 of spores, such that sterilant can reach the spores to produce sterilized spores. In addition, during sterilization, the frangible container 148 and the second reservoir 128 are in a closed state in which the liquid 130 is protected from the sterilant and is not in fluid communication with the first reservoir 122, the spore reservoir 126, the locus 124 of spores, or the sterilant path 132.

Following sterilization, the chemical indicator 186 indicates that the biological sterilization indicator 102 has been exposed to sterilizing conditions. The effectiveness of the sterilization process can be determined by the biological sterilization indicator system 100 by reading the biological sterilization indicator 102 with the detection device 104. For example, the biological sterilization indicator 102 can be positioned in the recess 106 by moving the biological sterilization indicator 102 substantially along the longitudinal direction of the recess 106 to the first position 173, causing the first actuator 166 of the detection device 104 to actuate the first movable member 160 to deflect out of the plane of the rear wall 116 to force the frangible container 148 into contact with the fracturing member 164 to fracture the frangible container 148. Fracturing the frangible container 148 changes the second reservoir 128 from its closed state to its open state and releases the liquid 130 into the first reservoir 122 into fluid communication with the spore reservoir 126 and the locus of sterilized spores 124. The liquid 130 can either include nutrient medium (e.g., germination medium) for the spores, or the liquid 130 can contact nutrient medium in a dry form (e.g., in a powdered or tablet form) to form nutrient medium, such that a mixture including the sterilized spores and nutrient medium is formed. The mixture can then be incubated, for example, in the detection device 104.

After the frangible container 148 has been broken and before the sterilant path 132 has been sealed, air within the first reservoir 122 can escape from the biological sterilization indicator 102 via the sterilant path 132 to allow the liquid 130 to move into the spore reservoir 126.

The biological sterilization indicator 102 can then be moved in the recess 106 to the second position 175 causing the second actuator 176 to actuate the second movable member 170 to deflect out of the plane of the rear wall 116 to seal the sterilant path 132, and as a result, inhibiting evaporation of the liquid 130 as well as minimizing the introduction of contaminating or foreign organisms, objects or materials into the first reservoir 122.

To detect a detectable change in the spores, the biological sterilization indicator 102 can be assayed by the detection device 104 immediately after the liquid 130 and the spores have been combined to achieve a baseline reading. After that, any detectable change from the baseline reading can be detected by the detection device 104. The biological sterilization indicator 102 can be monitored and measured continuously or intermittently while the biological sterilization indicator 102 is coupled to the detection device 104 (e.g., while the spores are being incubated in the liquid 130), and the detection device 104 is in a detection mode. In some embodiments, a portion of, or the entire, incubating step may be carried out prior to measuring the detectable change. In some embodiments, incubation can be carried out at one temperature (e.g., at 37° C., at 50-60° C., etc.), and measuring of the detectable change can be carried out at a different temperature (e.g., at room temperature, 25° C., or at 37° C.).

Due to the means described above that can be employed to improve the signal from the biological sterilization indicator 102, (such as aspect ratios, means for inhibiting evaporation of the liquid 130 from the biological sterilization indicator 102, small volumes, minimal "z dimension," reflective surface(s) in the spore reservoir 126, etc.) the readout time from the biological sterilization indicator 102 (i.e., the time to determine the effectiveness of the sterilization process) can be, in some embodiments, less than 8 hours, in some embodiments, less than 1 hour, in some embodiments, less than 30 minutes, in some embodiments, less than 15 minutes, in some embodiments, less than 5 minutes, and in some embodiments, less than 1 minute.

Figure 5:
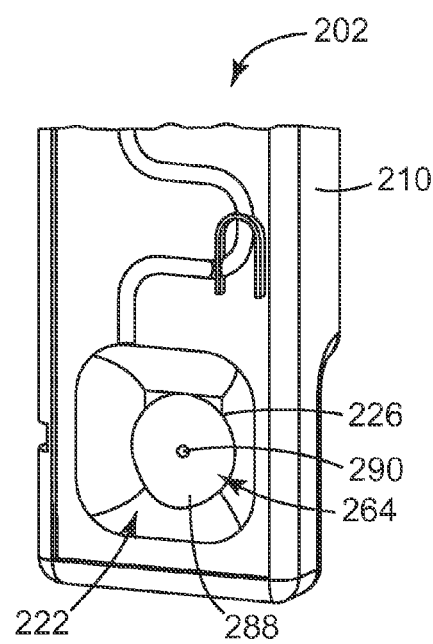
FIG. 5 is a rear partial perspective view of a biological sterilization indicator according to another embodiment of the present disclosure, with portions removed for clarity.

FIG. 5 illustrates a biological sterilization indicator 202 according to another embodiment of the present disclosure. The biological sterilization indicator 202 can also be used with the detection device 104 and includes many of the same elements and features described above with reference to the biological sterilization indicator 102 of FIGS. 1-4, except that the biological sterilization indicator 202 includes a different fracturing member 264. Accordingly, elements and features corresponding to elements and features in the illustrated embodiment of FIGS. 1-4 are provided with the same reference numerals in the 200 series. Reference is made to the description above accompanying FIGS. 1-4 for a more complete description of the features and elements (and alternatives to such features and elements) of the embodiment illustrated in FIG. 5. A rear wall of a housing 210 of the biological sterilization indicator 202 and the frangible container that contains the liquid have been removed from FIG. 5 for clarity.

The fracturing member 264 of the biological sterilization indicator 202 shown in FIG. 5 includes a cover 288, or wall, positioned adjacent the spore reservoir 226 to fluidly separate the first reservoir 222 and the spore reservoir 226, except for an aperture 290 in the cover 288 that provides fluid communication between the spore reservoir 226 and the first reservoir 222. Because the aperture 290 extends through the thickness of the cover 288, the aperture 290 can be considered a channel that fluidly couples the first reservoir 222 and the spore reservoir 226.

The biological sterilization indicator 202 shown in FIG. 5 functions similarly to the biological sterilization indicator 102 of FIGS. 1-4, in that when a portion of a rear wall (removed from FIG. 5 for clarity) of the housing 210 of the biological sterilization indicator 202 adjacent the first reservoir 222 is deformed, a frangible container (not shown) is pressed against the cover 288. The only portion of the frangible container that is not supported by the cover 288, i.e., the portion of the frangible container adjacent the aperture 290, can fracture, and expel any liquid within the frangible container into the spore reservoir 226 via the aperture 290. In some embodiments, the front portion of the frangible container (i.e., the portion facing the cover 288 and the spore reservoir 226) can be formed of a weaker, more frangible, material than the rear portion (i.e., the portion facing away from the cover 288), such that the front portion of the frangible container breaks against the cover 288 more easily than against the rear wall of the housing 210 of the biological sterilization indicator 202. In such embodiments, the portion of the rear wall adjacent the first reservoir 222 can remain deformed (e.g., by an actuator on the detection device 104, by virtue of the material makeup of the rear wall, or by another mechanism) to maintain the frangible container in a positioned pressed up against the cover 288.

FIG. 6 illustrates a biological sterilization indicator 302 according to another embodiment of the present disclosure. The biological sterilization indicator 302 can also be used with the detection device 104 and includes many of the same elements and features described above with reference to the biological sterilization indicator 102 of FIGS. 1-4. Accordingly, elements and features corresponding to elements and features in the illustrated embodiment of FIGS. 1-4 are provided with the same reference numerals in the 300 series. Reference is made to the description above accompanying FIGS. 1-4 for a more complete description of the features and elements (and alternatives to such features and elements) of the embodiment illustrated in FIG. 6.

As shown in FIG. 6, unlike the biological sterilization indicator 102 shown in FIGS. 1-4, the first reservoir 322 is not directly adjacent the spore reservoir 326, but rather, is fluidly coupled to the spore reservoir 326 via a channel 392. As a result, when a movable member 360 is actuated by an actuator of the detection device 104 to move out of the plane of the rear wall 316 of the housing 310, the frangible container 348 is pressed into contact with the fracturing member 364, and the liquid 330 is released into the first reservoir 322 and into the channel 392 via the aperture 391. Any air in the first reservoir 322 that is displaced by the liquid 330 can escape from the first reservoir 322 via a first sterilant path 332a or via the channel 392. The first sterilant path 332a is positioned to fluidly couple the first reservoir 322 to ambience. A second sterilant path 332b is positioned to fluidly couple the spore reservoir 326 to ambience. As a result, during sterilization, a sterilant can enter one or both of the sterilant paths 332a,b to sterilize the spores in the spore reservoir 326.

The liquid 330 can either include nutrient medium for the spores or the liquid 330 can mix with nutrient medium that is provided in a dry form somewhere along the fluid path between, and including, the first reservoir 322, the channel 392, and the spore reservoir 326. The liquid 330 can enter the spore reservoir 326 via the channel 392. In some embodiments, the total available volume of the liquid 330 can be greater than the volume of the spore reservoir 326, such that the spore reservoir 326 is allowed to be filled with the liquid 330.

After sterilization, and after the frangible container 348 has been broken, and the liquid 330 has been allowed to move into the spore reservoir 326 (e.g., by gravity, capillary action, centrifugal force, and/or as a result of the pressure differential created when the frangible container 348 fractured), the second sterilant path 332b can be sealed, and the channel 392 can be sealed. For example, the biological sterilization indicator 302 can be moved into a position within the detection device 104 where actuators of the detection device 104 will cause movable members 370a and 370b to seal the channel 392 and the second sterilant path 332b, respectively. Alternatively, or in addition, to the channel 392 being sealed, the first sterilant path 332a can be sealed.

The aspect ratios described above can be employed for the cross-sectional area of the first sterilant path 332a relative to the volume of the first reservoir 322, the cross-sectional area of the channel 392 relative to one or both of the volume of the first reservoir 322 and the volume of the spore reservoir 326, and/or the cross-sectional area of the second sterilant path 332b relative to the volume of the spore reservoir 326.

It should be understood that any variations of any of the elements or mechanisms of the biological sterilization indicator 302 described above (e.g., the fracturing member 264 illustrated in FIG. 5) can be employed in the biological sterilization indicator 302 without departing from the spirit and scope of the present disclosure.

In some embodiments, the liquid 330 is not contained in the frangible container 348, but rather, the liquid 330 is contained directly in the first reservoir 322. In such embodiments, the first sterilant path 332 is either sealed during sterilization or the biological sterilization indicator 302 does not include the first sterilant path 332, and the aperture 391 to the channel 392 is covered with a frangible barrier, valve (e.g., a one-way valve, a pressure-controlled valve, or a combination thereof), a plug, or the like, or combinations thereof. In such embodiments, the movable member 360, or a similar mechanism, can cause an increase in pressure within the first reservoir 322 when it is deflected, such that the frangible barrier is broken (or the valve is activated, the plug is dislodged, or combinations thereof) and the liquid 330 can move into the channel 392 and into the spore reservoir 326. In such embodiments, air can escape from the spore reservoir 326 via the second sterilant path 332 prior to the second sterilant path 332 being sealed. In some embodiments, an actuator in a detection device can cause the deflection of the movable member 360. In some embodiments, the actuator can include a protrusion, cam, detent mechanism, a laser, or a combination thereof.

In some embodiments, the channel 392 can include microchannels, or similar microstructured features, such that the liquid 330 can move from the first reservoir 322 to the spore reservoir 326 via capillary action. Such microchannels can include those described in Johnston et al., U.S. Pat. No. 7,223,364, which is incorporated herein by reference. In some embodiments, the above configuration of the container 348 is employed where the container 348 is covered with a frangible barrier, or the frangible container 348 itself is the entire first reservoir 322, in combination with a channel 392 including microchannels. In such embodiments, the liquid 330 can be contained in a blister-package-type frangible container 348, such that the liquid 330 flows into the microchannels of the channel 392 when the frangible container 348 is broken (e.g., squeezed).

An alternative biological sterilization indicator 302A to the biological sterilization indicator 302 illustrated in FIG. 6 is shown in FIG. 6A. As shown in FIG. 6A, the biological sterilization indicator 302A includes a first reservoir 322A, and a plurality of spore reservoirs 326A, each spore reservoir 326A including one or more loci 324A of spores. In addition, the biological sterilization indicator 302A includes a detection window 150A positioned adjacent each spore reservoir 326A. Each of the spore reservoirs 326A are in fluid communication with a common channel 392A and/or a common sterilant path 332A via individual channels 399. In some embodiments, the channels 399 can form a portion of one or both of the channel 392A and 332A.

In the biological sterilization indicator 302A, liquid can be contained in a second reservoir defined by a frangible container, as described above with respect to the biological sterilization indicator 302 in FIG. 6 (e.g., where the sterilant path 332A functions as a vent to facilitate the movement of the liquid into the spore reservoirs 332A), or the liquid can be contained directly in the first reservoir 322A.

In embodiments in which the liquid is contained directly in the first reservoir 322A, the liquid can be maintained in the first reservoir 322A by a frangible barrier positioned over an aperture 391A or along the channel 392A or the channels 399, or the liquid can be maintained out of fluid communication with the spores by surface tension, for example, by employing the aspect ratios described above for the cross-sectional area of the channel 392A relative to the volume of the first reservoir 322A; for the cross-sectional area of the channel 399 relative to the volume of the channel 392A; for the cross-sectional area of an opening into the spore reservoirs 326A relative to the volume of the channels 399; or the like; or combinations thereof. In such embodiments, centrifugal force can be used to fracture the frangible barrier or to overcome the surface tension to move the liquid from the first reservoir 322A to the spore reservoirs 326A. For example, in some embodiments, the biological sterilization indicator system includes a detection device that includes a centrifuge. In such embodiments, the detection device can include (or can include an actuator that includes) a centrifuge for changing the reservoir that contains the liquid from a closed state in which the liquid is not in fluid communication with the spores to an open state in which the liquid is in fluid communication with the spores. Alternatively, the biological sterilization indicator 302A can be centrifuged prior to coupling the biological sterilization indicator 302A to a detection device.

In some embodiments, the aspect ratios described above can be employed for the cross-sectional area of the channel 392A relative to the volume of each channel 399 or relative to the volume of each spore reservoir 326A; for the cross-sectional area of each channel 399 relative to the volume of the adjacent spore reservoir 326A; for the cross-sectional area of the sterilant path 332A relative to the volume of the each channel 399 or relative to the volume of each spore reservoir 326A. Such aspect ratios can be employed to control the diffusion rate of spores and/or signals out of the spore reservoirs 326A.

Figures 7, 8:
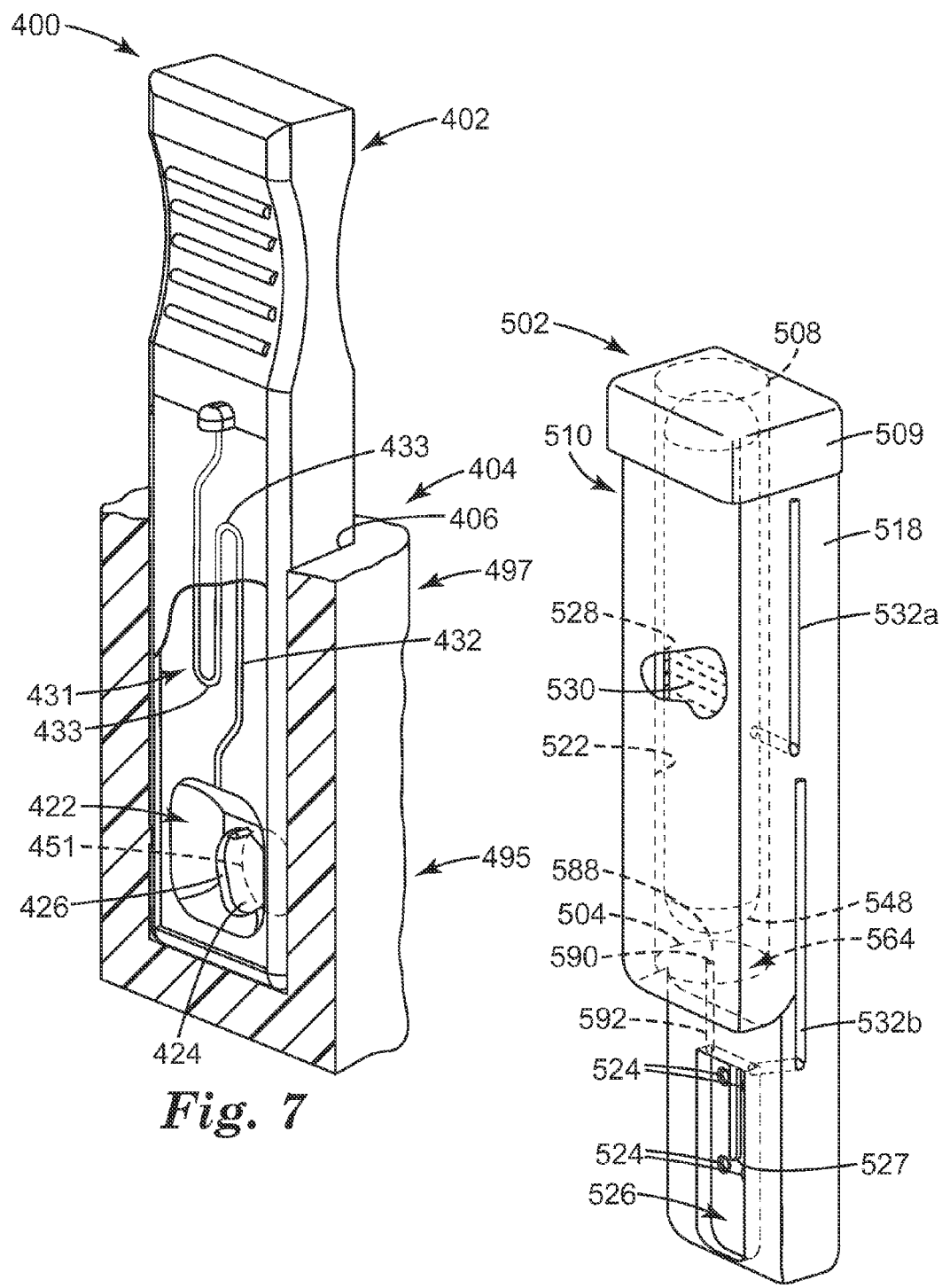
FIG. 7 is a rear perspective view of a biological sterilization indicator system according to another embodiment of the present disclosure, with portions removed for clarity.
FIG. 8 is rear perspective view of a biological sterilization indicator according to another embodiment of the present disclosure.

FIG. 7 illustrates a biological sterilization indicator system 400 according to another embodiment of the present disclosure, the biological sterilization indicator system 400 including a biological sterilization indicator 402 (shown with the rear wall and frangible container removed for clarity) and a detection device 404 (shown in cross-section in FIG. 7). The biological sterilization indicator system 400 includes many of the same elements and features described above with reference to the biological sterilization indicator system 100 of FIGS. 1-4. Accordingly, elements and features corresponding to elements and features in the illustrated embodiment of FIGS. 1-4 are provided with the same reference numerals in the 400 series. Reference is made to the description above accompanying FIGS. 1-4 for a more complete description of the features and elements (and alternatives to such features and elements) of the embodiment illustrated in FIG. 7.

In FIG. 7, the biological sterilization indicator 402 is shown positioned in a recess 406 of the detection device 404. As shown in FIG. 7, the sterilant path 432 includes a plurality of bends 433 that are oriented so as to form a trap 431. Such a trap 431 can serve as a means for inhibiting evaporation of liquid from the first reservoir 422 or for inhibiting the introduction of contaminating or foreign organisms, objects or materials. For example, in some embodiments, the detection device 404 includes two temperature zones, a first temperature zone 495 and a second temperature zone 497. The first temperature zone 495 can be positioned adjacent the first reservoir 422 and the spore reservoir 426 and locus 424 of spores when the biological sterilization indicator 402 is positioned in the recess 406 of the detection device 404. The second temperature zone 497 can be positioned adjacent the sterilant path 432 when the biological sterilization indicator 402 is positioned in the recess 406 of the detection device 404. The first temperature zone 495 can be heated to incubate the spores at the desired or optimal incubation temperature, for example, after the spores have been placed into fluid communication with the liquid. The second temperature zone 497 can be kept at a temperature (e.g., room temperature) that is lower than that of the first temperature zone 495. As a result, the portion of the biological sterilization indicator 402 that includes the trap 431 of the sterilant path 432 will remain cooler than the portion of the biological sterilization indicator 402 that includes the first reservoir 422. As a result, condensation can form within the sterilant path 332, and particularly, within the trap 431 of the sterilant path 332, forming a gas lock (e.g., an air lock), such that the first reservoir 422 can be protected from evaporation, as well as introduction of contaminating or foreign organisms, objects or materials. Similarly, in some embodiments, a material (e.g. a wax, such as Paraffin wax) can be positioned in the trap 431 of the sterilant path 432 that is liquid at higher temperatures and solid at lower temperatures, such that as the second temperature zone 497 cools the portion of the biological sterilization indicator 402 adjacent the sterilant path 432, the material hardens and/or expands, essentially sealing of the sterilant path 432.

The trap 431 is shown in FIG. 7 by way of example only; however, it should be understood that the multiple temperature zones and the condensation collection technique can be applied to other configurations of sterilant paths 432 as well, such as the sterilant path 132 shown in FIGS. 1-4 above, a sterilant path that is straight along substantially all of its length, etc. In such embodiments, the second temperature zone 497 can be positioned adjacent the sterilant path to cause any evaporated liquid 430 to condense and return to a position near the spores (e.g., the first reservoir 422)

In addition, as shown in FIG. 7, the detection device 404 can also include reading or detection window 451 that corresponds to a detection window 450 on the biological sterilization indicator 402, such that when the biological sterilization indicator 402 is positioned in the recess 406 of the detection device 404, the detection window 451 of the detection device 404 will be substantially aligned with and shaped and dimensioned to substantially match the detection window 450 of the biological sterilization indicator 402, such that substantially all of a signal generated by the spores can be detected by the detection device 404. For example, the spores can be excited by an excitation signal from the detection device 404 via the detection windows 450 and 451, and the spores can emit a response signal back to the detection device via the detection windows 450 and 451. In addition, at least partially because of the geometry of the detection windows 450 and 451, and at least partially because diffusion of any signal generated from the spores out of the first reservoir 422 is minimized, substantially all of the signal generated by the spores can be detected by the detection device 404.

FIG. 8 illustrates a biological sterilization indicator 502 according to another embodiment of the present disclosure. The biological sterilization indicator 502 can also be used with the detection device 104 and includes many of the same elements and features described above with reference to the biological sterilization indicator 102 of FIGS. 1-4. Accordingly, elements and features corresponding to elements and features in the illustrated embodiment of FIGS. 1-4 are provided with the same reference numerals in the 500 series. The biological sterilization indicator 502 also includes many of the same elements and features described above with reference to the biological sterilization indicator 302 of FIG. 6. As such, elements and features corresponding to elements and features in the illustrated embodiment of FIG. 6 are provided with the same reference numerals in the 500 series. Reference is made to the description above accompanying FIGS. 1-4 and 6 for a more complete description of the features and elements (and alternatives to such features and elements) of the embodiment illustrated in FIG. 8.

The biological sterilization indicator 502 includes a first reservoir 522 dimensioned to receive a frangible container 548 that contains a liquid 530. The first reservoir 522 is in fluid communication with ambience via a first sterilant path 532a. The first reservoir 522 is further fluidly coupled to a spore reservoir 526 via a channel 592. By way of example only, the spore reservoir 526 includes a plurality of loci 524 of spores, but it should be understood that the spore reservoir 526 can instead include one locus 524 of spores.

In some embodiments, as shown in FIG. 8, the spore reservoir 526, or another portion of the biological sterilization indicator 502 can include a fluid guide 527 to facilitate the movement of fluid in the biological sterilization indicator 502. Particularly, in the embodiment illustrated in FIG. 8, the fluid guide 527 is positioned in the spore reservoir 526 to facilitate the movement of the liquid 530 to each of the plurality of loci 124 of spores to inhibit the liquid 130 from being able to flow from the channel 592 to the second sterilant path 532b without contacting substantially all of the spores. The fluid guide 527 shown in FIG. 8 extends downwardly from an upper wall of the spore reservoir 526 to guide fluid down and through the spore reservoir 526. However, it should be understood that a variety of shapes and configurations can be employed as a fluid guide to directed fluid movement in the biological sterilization indicator 502, depending on the desired flow.

When the frangible container 548 is broken and the liquid 530 is released into the first reservoir 522, the liquid 530 can move into the channel 592. Any air in the first reservoir 522 that is displaced by the liquid 330 can escape from the first reservoir 522 via the first sterilant path 332a or via the channel 592. The first sterilant path 532a is positioned to fluidly couple the first reservoir 522 to ambience. A second sterilant path 532b is positioned to fluidly couple the spore reservoir 526 to ambience. As a result, during sterilization, a sterilant can enter one or both of the sterilant paths 532a,b to sterilize the spores in the spore reservoir 526.

In some embodiments, the biological sterilization indicator 502 can be configured to inhibit fluid communication between the first reservoir 522 and the spore reservoir 526 during sterilization, such that the spores are in fluid communication with ambience during sterilization substantially only via the second sterilant path 532b. For example, in some embodiments, one or more of the first reservoir 522, the spore reservoir 526 and the channel 592 (e.g., at its inlet, its outlet, or along its length) can be equipped with one or more of a valve, a frangible barrier, a movable plug, or the like, or combinations thereof, that is configured to inhibit fluid communication between the first reservoir 522 and the spore reservoir 526 during sterilization but to allow fluid communication between the first reservoir 522 and the spore reservoir 526 after sterilization, and particularly, after the frangible container 548 has been fractured.

The liquid 530 can either include nutrient medium for the spores or the liquid 530 can mix with nutrient medium that is provided (e.g., in a dry form) somewhere along the fluid path between, and including, the first reservoir 522, the channel 592, and the spore reservoir 526. The liquid 530 can enter the spore reservoir 526 via the channel 592. In some embodiments, as shown in FIG. 8, the total available volume of the liquid 530 can be greater than the volume of the spore reservoir 526, such that the spore reservoir 526 is allowed to be filled with the liquid 530.

The biological sterilization indicator 502 can be a self-contained biological sterilization indicator, similar to the biological sterilization indicators 102, 202, 302, and 402 described above, or the biological sterilization indicator 502 can be configured such that the frangible container 548 can be added to the first reservoir 522 by a user (e.g., before or after sterilization). The liquid 530 is protected by the frangible container 548 from being in fluid communication with the sterilant during sterilization, but in some embodiments, the frangible container 548 can be added after sterilization to ensure that the frangible container 548 is not broken in the biological sterilization indicator 502 prematurely.

Whether the frangible container 548 is added to the biological sterilization indicator 502 by a user or during a manufacturing process, the biological sterilization indicator 502 can be assembled by inserting the frangible container 548 containing the liquid 530 into an open end 508 of a housing 510 of the biological sterilization indicator 502, and sealing the open end 508 of the housing 510, for example, with a cap 509. After sterilization and after the frangible container 548 has been positioned in the biological sterilization indicator 502, the frangible container 548 can be broken. In some embodiments, at least one wall of the housing 510 is deformable, and the frangible container 548 can be broken by deforming the housing 510 surrounding the frangible container 548, due to the increased pressure. In some embodiments, the first reservoir 522 is defined by a least one rigid wall and the frangible container 548 can be broken by moving (e.g., firmly shaking) the biological sterilization indicator 502 or by tapping the biological sterilization indicator 502 against a hard surface to cause the frangible container 548 to break against an inner surface 552 of the first reservoir 522. In some embodiments, the biological sterilization indicator 502 includes a fracturing member 564 similar to either the fracturing member 164 illustrated in FIG. 1-4 or the fracturing member 264 illustrated in FIG. 5 that engages the frangible container 548, for example, in response to deforming an adjacent portion of the housing 510. By way of example only, the fracturing member 564 is illustrated as being similar to the fracturing member 264 of FIG. 5, and includes a cover 588 and an aperture 590 in the cover 588. When the frangible container 548 is broken, the liquid 530 is released into the channel 592 via the aperture 590.

After sterilization, when the frangible container 548 is broken, the liquid 530 can move into the spore reservoir 526 (e.g., by gravity and/or as a result of the pressure differential created when the frangible container 548 fractured), and the first and second sterilant paths 532*a,b* can be sealed. For example, the biological sterilization indicator 502 can be moved into a position within the detection device 104 where one or more actuators of the detection device 104 can actuate means (such as the movable members 170, 370*a* and 370*b*, and their alternatives, described above) to seal the sterilant paths 532*a,b*, either simultaneously or in succession. For example, one or more actuators of the detection device 104 that are positioned to cooperate with a left side wall 518 of the housing 510 can be used to seal one or both of the first and second sterilant paths 532*a,b*.

Alternatively, or in addition, the channel 592 can be sealed to ensure that diffusion of the spore signal out of the spore reservoir 526 and evaporation of the liquid 530 out of the spore reservoir 526 is minimized. In the embodiment illustrated in FIG. 8, however, the volume of liquid 530 in the frangible container 548 is large enough to fill the spore reservoir 526 and a substantial portion of the first reservoir 522 after the frangible container 548 has been broken, such that evaporation of the liquid 530 can be controlled by sealing the first and second sterilant paths 532*a,b*. In addition, the aspect ratios of the channel 592 and the second sterilant path 532*b*, relative to the spore reservoir 526 can be controlled to minimize the diffusion of any spore signal out of the spore reservoir 526, as described above.

By way of example only, the aspect ratios described above can be employed for the cross-sectional area of the first sterilant path 532*a* relative to the first reservoir 522, the channel 592 relative to one or both of the first reservoir 522 and the spore reservoir 526, and/or the second sterilant path 532*b* relative to the spore reservoir 526.

In addition or alternatively, in some embodiments, all or a portion of the frangible container 548 can be used to seal the channel 592 after the biological sterilization indicator 502 has been activated (e.g., after the liquid 530 has been released from the container 548). For example, in some embodiments, portions (e.g., shards) of the fractured container 548 can be positioned to substantially inhibit diffusion of the spores and/or a signal out of the spore reservoir 526. Alternatively, or in addition, in some embodiments (e.g., embodiments employing a polymeric container 548), at least a portion of the fractured or punctured container 548 can be adapted to move downwardly in the first reservoir 522 in order to at least partially fill, seal and/or cover the channel 592. Other embodiments disclosed herein can also be configured to facilitate using all or a portion of the container 548 to inhibit diffusion, for example, out of the spore reservoir 526. It can be advantageous if, in such embodiments, the biological sterilization indicator 502 is configured to maintain at least some of the portions of the fractured container 548 out of the spore reservoir 526, for example, to facilitate, and minimize any disruption to, the detection processes. For example, the biological sterilization indicator 502 is configured to inhibit portions of the container 548 from moving into the spore reservoir 526.

It should be understood that any variations of any of the elements or mechanisms of the biological sterilization indicators 102, 202, 302, and 402 described above (e.g., the fracturing member 264 illustrated in FIG. 5) can be employed in the biological sterilization indicator 502 without departing from the spirit and scope of the present disclosure.

FIGS. 9-11 illustrate a biological sterilization indicator system 600 according to another embodiment of the present disclosure, the biological sterilization indicator system 600 including a biological sterilization indicator 602 and a detection device 604 (shown in FIGS. 9 and 11). The biological sterilization indicator system 600 includes many of the same elements and features described above with reference to the biological sterilization indicator system 100 of FIGS. 1-4.

Accordingly, elements and features corresponding to elements and features in the illustrated embodiment of FIGS. 1-4 are provided with the same reference numerals in the 600 series. Reference is made to the description above accompanying FIGS. 1-4 for a more complete description of the features and elements (and alternatives to such features and elements) of the embodiment illustrated in FIGS. 9-11.

Figure 10A:
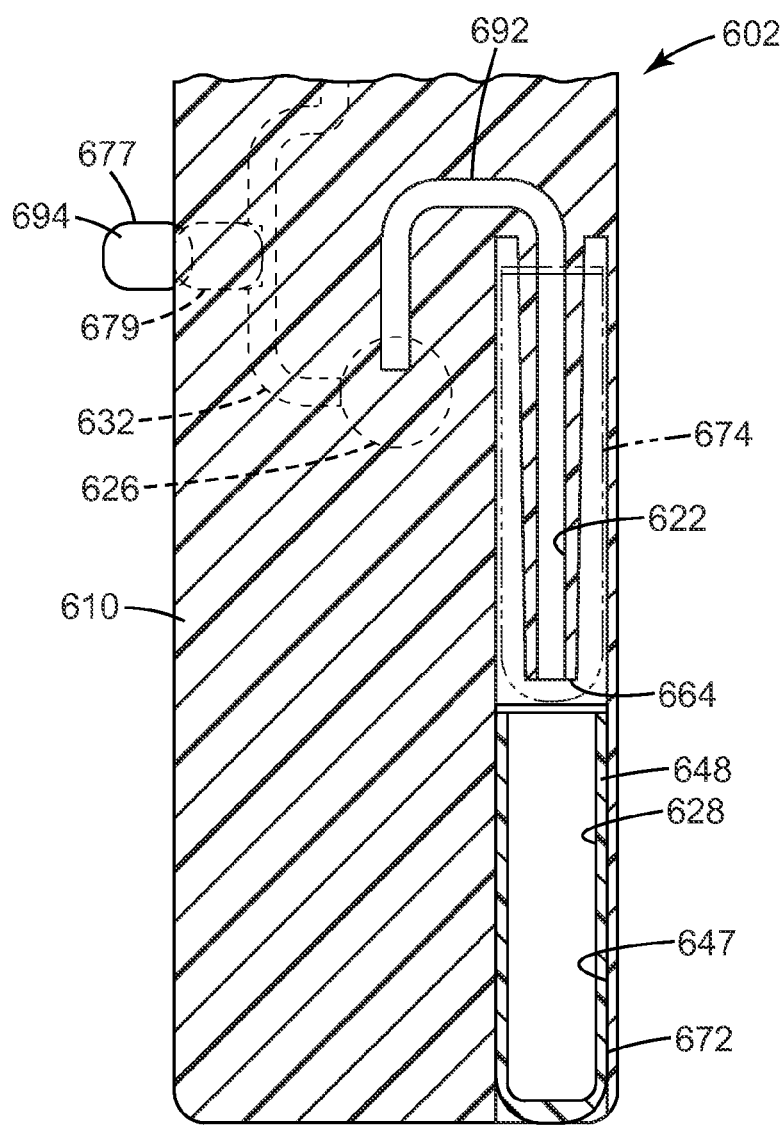
FIG. 10A is a rear partial cross-sectional view of the biological sterilization indicator of FIGS. 9 and 10, taken along line 10A-10A in FIG. 10.

As shown in FIG. 9, the biological sterilization indicator 602 includes a housing 610 and is dimensioned to be received in a recess 606 of the detection device 604. Liquid 630 is positioned in a container 648 that includes a frangible cover 649. Similar to the frangible containers (e.g., frangible container 148 in FIGS. 1-4), the frangible cover 649 can be formed of a variety of materials, including, but not limited to, one or more of metal (e.g., foil), polymer, glass, and combinations thereof. In some embodiments, the frangible cover 649 can include, or be used in combination with, a seal (e.g., an elastomeric seal, such as an o-ring) to facilitate creating a fluid-tight seal on the container 648. The container 648 defines a second reservoir 628 in which the liquid 630 is contained during sterilization. As shown in FIGS. 9, 10 and 10A, the container 648 is dimensioned to reside in a recess 647 of the housing 610 of the biological sterilization indicator 602 during sterilization.

As shown in FIGS. 9 and 10, the biological sterilization indicator 602 further includes a first reservoir 622 and a locus 624 of spores positioned in a spore reservoir 626. A detection window 650 of the biological sterilization indicator 602 is positioned adjacent the spore reservoir 626 and sized to substantially match the spore reservoir 626 and the locus 624 of spores. As shown in FIG. 9, the detection device 604 includes a corresponding detection window 651 sized to substantially match the detection window 650 of the biological sterilization indicator 602.

The biological sterilization indicator 602 further includes a channel 692 positioned to fluidly couple the first reservoir 622 and the spore reservoir 626, and a sterilant path 632 positioned to fluidly couple the spore reservoir 626 to ambience (e.g., during sterilization). The first reservoir 622 includes a fracturing member 664, which in the embodiment illustrated in FIGS. 9-11 includes a hollow tube positioned concentrically within the first reservoir 622, such that a lower end of the tube is positioned to fracture the frangible cover 649 of the container 648, changing the container 648 and the second reservoir 628 from a first closed state in which the second reservoir 628 and the liquid 630 are not in fluid communication with the first reservoir 622 or the spore reservoir 626 to a second open state in which the second reservoir 628 is in fluid communication with the first reservoir 622 and the spore reservoir 626.

Figure 11:
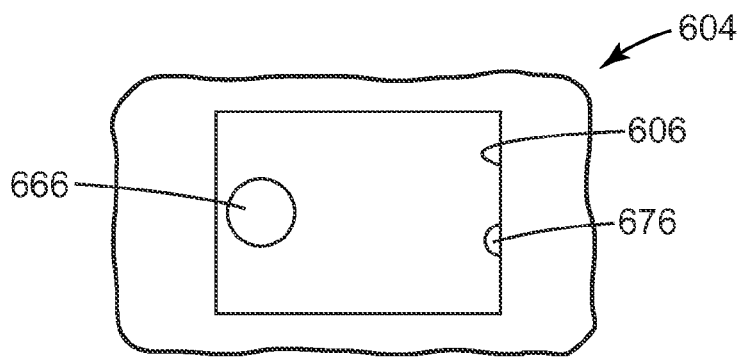
FIG. 11 is a top plan view of the detection device of FIG. 9.

As shown in FIGS. 9 and 11, the detection device 604 includes an actuator 666 positioned and dimensioned to be received in the recess 647 of the biological sterilization indicator 602 to force the container 648 from a first position 672 in the housing 610 (see FIG. 10A) in which the container 648 resides in the recess 647 to a second position 674 in the housing 610 (see FIG. 10A, shown in phantom lines) in which the container 648 has been pushed upwardly, the frangible cover 649 has been fractured by the fracturing member 664, and the liquid 630 has been positioned in fluid communication with the first reservoir 622. The actuator 666 includes a protrusion that extends upwardly from a bottom wall of the recess 606 in the detection device 604.

After sterilization, as the biological sterilization indicator 602 is moved into the recess 606 of the detection device 604, the biological sterilization indicator 602 moves to a first position in which the actuator 666 actuates the container 648 to move from its first position 672 to its second position 674 in the housing 610. As the liquid 630 is released from the container 648, the liquid 630 fills the channel 692 and is moved in the spore reservoir 626. The sterilant path 632 can function as a vent during the fluid transfer from the first reservoir 622 to the spore reservoir 626 to facilitate the movement of the liquid 630 into the spore reservoir 626 and into contact with the spores. After at least a portion of the liquid 630 has moved into the spore reservoir 626, the sterilant path 632 can be sealed to inhibit evaporation of the liquid 630 and to minimize the introduction of any contaminating or foreign organisms, objects or materials.

As shown in FIGS. 9 and 11, the detection device 604 includes a second actuator 676 that can include a plug 694 that is configured to move from a first position 677 in which the plug 694 is not obstructing the sterilant path 632 to a second position 679 in which the plug 694 is obstructing the sterilant path 632. The actuator 676 of the detection device 604 can be actuated as the biological sterilization indicator 602 is moved further into the recess 606 of the detection device 604 to a second position. The actuator 676 can include the plug 694, or the actuator 676 can include a mechanism positioned to move the plug 694 from its first position 677 to its second position 679 as the biological sterilization indicator 602 is moved to its second position in the detection device 604. Such a mechanism can include a cam, a spring-loaded protrusion, other suitable means for actuating the plug 694, and combinations thereof.

The plug 694 can be formed of a variety of materials, including, but not limited to, one or more of a polymer, an elastomer, and combinations thereof. In some embodiments, the plug 694 can be formed of a first material, such as a metal, polymer, glass, or a combination thereof, and can include or be coupled to an elastomer that forms at least a portion of an outer surface of the plug 694 to facilitate forming a fluid-tight seal. In addition, in some embodiments, the plug 694 can be formed of a material (e.g. a wax, such as Paraffin wax) that has a melting temperature above the incubation temperature. In such embodiments, the biological sterilization indicator 602 or the detection device 604 can be configured to hold the material out of contact with the spores during sterilization (i.e., when the material is above its melting temperature), and the material can be positioned to seal the sterilant path 432 when the biological sterilization indicator 402 has been activated, i.e., when the liquid 630 has been allowed to combine with the spores (e.g., when the material is below its melting temperature).

As described above with reference to the biological sterilization indicators 302 and 502 of FIGS. 6 and 8, respectively, the aspect ratios of one or both of the cross-sectional area of the sterilant path 632 and the channel 692 relative to the volume of the spore reservoir 626 can be controlled to minimize the diffusion of any signal generated by the spores out of the spore reservoir 626 to maximize the concentration of the signal and to maximize the signal detected by the detection device 604.

FIGS. 12A-12C schematically illustrate a biological sterilization indicator 702 according to another embodiment of the present disclosure. The biological sterilization indicator 702 includes many of the same elements and features described above with reference to the biological sterilization indicator 102 of FIGS. 1-4. Accordingly, elements and features corresponding to elements and features in the illustrated embodiment of FIGS. 1-4 are provided with the same reference numerals in the 700 series. Reference is made to the description above accompanying FIGS. 1-4 for a more complete description of the features and elements (and alternatives to such features and elements) of the embodiment illustrated in FIGS. 12A-12C.

The biological sterilization indicator 702 includes a housing 710, a first reservoir 722, a locus 724 of spores located on a fracturing member 764, a frangible container 748 that defines a second reservoir 728 containing a liquid 730, and a third reservoir 729 positioned to receive the liquid 730 and the spores after the frangible container 748 has been fractured by the fracturing member 764. The frangible container 748 is positioned in the housing 710 along a path of the fracturing member 764. The biological sterilization indicator 702 further includes a sterilant path 732 positioned to fluidly couple the first reservoir 722 to ambience during sterilization.

The fracturing member 764 is movable within the first reservoir 722 along a longitudinal axis of the biological sterilization indicator 702 by a plunger 794. The plunger 794, or at least an upper portion of the plunger 794 can be dimensioned to fit within the first reservoir 722 and can include a seal to seal the first reservoir 722. The plunger 794 can be moved manually, for example, by a handle (not shown), or the plunger 794 can be moved by an actuator, either directly or indirectly, of a detection device, such that the plunger 794 moves between a first position 787, shown in FIG. 12A, a second position 789, shown in FIG. 12B, and a third position 793 shown in FIG. 12C.

FIGS. 12A-12C schematically illustrate the biological sterilization indicator 702 at three points in time, respectively. FIG. 12A shows the biological sterilization indicator 702 at a point in time before or during sterilization. FIGS. 12B and 12C show the biological sterilization indicator 702 after sterilization.

In FIG. 12A, the plunger 794, the fracturing member 764 and the locus 724 of spores are in a first position 787 within the first reservoir 722. The first reservoir 722 is in fluid communication with ambience via the sterilant path 732, and the second reservoir 728 defined by the frangible container 748 (and the liquid 730) are not in fluid communication with the first reservoir 722, ambience, sterilant, or the third reservoir 729. That is, the second reservoir 728 is in a closed state.

FIG. 12B shows schematically what occurs as the plunger 794, the fracturing member 764 and the locus 724 of spores are moved in the first reservoir 722. At the point in time shown in FIG. 12B, plunger 794, the fracturing member 764 and the locus 724 of spores have moved into the second position 789. The frangible container 748 has been fractured by the fracturing member 764, the frangible container 748 and the second reservoir 728 have changed from their closed state to their open state, the liquid 730 has begun to fill the third reservoir 729, the locus 724 of spores has begun moving into the third reservoir 729, and the first reservoir 722 is still in fluid communication with ambience via the sterilant path 732, such that any air in the third reservoir 729 can be vented back out through the first reservoir 722 and out the sterilant path 732.

FIG. 12C shows the plunger 794, the fracturing member 764 and the locus 724 of spores in the third position 793, such that the liquid 730 has filled the third reservoir 729, the locus 724 of spores has been positioned in the third reservoir 729 so that the liquid 730 is in contact with the spores, and the plunger 794 has sealed off the sterilant path 732, such that the first reservoir 722, the locus 124 of spores, the liquid 730, and the third reservoir 729 are not in fluid communication with ambience. Such sealing of the sterilant path 732 inhibits evaporation of the liquid 730 and minimizes the introduction of any contaminating or foreign organisms, objects or materials into the biological sterilization indicator 702.

By way of example only, the biological sterilization indicator 702 is shown in FIGS. 12A-12C as being oriented such that the plunger 794 moves from a first lower position 787 relative to the biological sterilization indicator 702 to a second higher position 789 relative to the biological sterilization indicator 702, and finally, to a third higher position 793 relative to the biological sterilization indicator 702. Such an orientation would allow an actuator within the detection device to actuate, either directly or indirectly, the plunger 794 to move between its first, second and third positions 787, 789 and 793 as the biological sterilization indicator 702 is moved relative to the detection device (e.g., moved into a recess of the detection device).

The plunger 794 (and the fracturing member 764 and the locus 724 of spores) are shown in FIGS. 12A-12C as being movable between three positions, namely, the first position 787 in FIG. 12A, the second position 789 in FIG. 12B, and the third position 793 in FIG. 12C. However, it should be understood that a number of other positions of the plunger 794 are possible and that the three positions shown in FIGS. 12A-12C are shown for illustration purposes only. For example, positions in which the plunger 794 is lower than is depicted in the first position 787 are possible, positions in which the plunger 794 is higher than is depicted in the third position 793 are possible, and a number of positions between the first position 787 and the third position 793 besides the illustrated second position 789 are possible.

In some embodiments, at least a portion of the sterilant path 732 can be routed through the plunger 794 and/or the fracturing member 764, in addition to or in lieu of routing the sterilant path 732 to the first reservoir 722. In such embodiments, a similar movement of the plunger 794 and fracturing member 764 as that described above can be used to move the portion of the sterilant path 732 that extends through the plunger 794 and/or the fracturing member 764 out of fluid communication with ambience or with another portion of the sterilant path 732, such that the locus 124 of spores are no longer in fluid communication with ambience.

FIGS. 13A-13C schematically illustrate a biological sterilization indicator 802 according to another embodiment of the present disclosure. The biological sterilization indicator 802 includes many of the same elements and features described above with reference to the biological sterilization indicator 102 of FIGS. 1-4 and the biological sterilization indicator 702 of FIGS. 12A-12C. Accordingly, elements and features corresponding to elements and features in the illustrated embodiment of FIGS. 1-4 and 12A-12C are provided with the same reference numerals in the 800 series. Reference is made to the description above accompanying FIGS. 1-4 and 12A-12C for a more complete description of the features and elements (and alternatives to such features and elements) of the embodiment illustrated in FIGS. 13A-13C.

The biological sterilization indicator 802 includes a housing 810, a first reservoir 822, a locus 824 of spores located on a fracturing member 864, a frangible container 848 that defines a second reservoir 828 containing a liquid 830, and a third reservoir 829 positioned to receive the liquid 830 and the spores after the frangible container 848 has been fractured by the fracturing member 864. The frangible container 848 is positioned in the housing 810 along a path of the fracturing member 864. The biological sterilization indicator 802 further includes a sterilant path 832 positioned to fluidly couple the first reservoir 822 to ambience during sterilization.

The fracturing member 864 is movable within the first reservoir 822 along a longitudinal axis of the biological sterilization indicator 802 by a plunger 894. The plunger 894, or at least an upper portion of the plunger 894 can be dimensioned to fit within the first reservoir 822 and can include a seal to seal the first reservoir 822. The plunger 894 can be moved manually, for example, by a handle (not shown), or the plunger 894 can be moved by an actuator, either directly or indirectly, of a detection device, such that the plunger 894 moves between a first position 887, shown in FIG. 13A, a second position 889, shown in FIG. 13B, and a third position 893 shown in FIG. 13C.

FIGS. 13A-13C schematically illustrate the biological sterilization indicator 802 at three points in time, respectively. FIG. 13A shows the biological sterilization indicator 802 at a point in time before or during sterilization. FIGS. 13B and 13C show the biological sterilization indicator 802 after sterilization.

In FIG. 13A, the plunger 894, the fracturing member 864 and the locus 824 of spores are in a first position 887 within the first reservoir 822. The first reservoir 822 is in fluid communication with ambience via the sterilant path 832, and the second reservoir 828 defined by the frangible container 848 (and the liquid 830) is not in fluid communication with the first reservoir 822, ambience, sterilant, or the third reservoir 829. That is, the second reservoir 828 is in a closed state.

FIG. 13B shows schematically what occurs as the plunger 894, the fracturing member 864 and the locus 824 of spores are moved in the first reservoir 822. At the point in time shown in FIG. 13B, plunger 894, the fracturing member 864 and the locus 824 of spores have moved into the second position 889. The frangible container 848 has been fractured by the fracturing member 864, the frangible container 848 and the second reservoir 828 have changed from their closed state to their open state, the liquid 830 has begun to fill the third reservoir 829, the locus 824 of spores has begun moving into the third reservoir 829, and the first reservoir 822 is still in fluid communication with ambience via the sterilant path 832, such that any air in the third reservoir 829 can be vented back out through the first reservoir 822 and out the sterilant path 832.

FIG. 13C shows the plunger 894, the fracturing member 864 and the locus 824 of spores in the third position 893, such that the liquid 830 has filled the third reservoir 829, the locus 824 of spores has been positioned in the third reservoir 829 so that the liquid 830 is in contact with the spores, and the plunger 894 has sealed off the sterilant path 832, such that the first reservoir 822 is no longer in fluid communication with ambience. Such sealing of the sterilant path 832 inhibits evaporation of the liquid 830 and minimizes the introduction of any contaminating or foreign organisms, objects or materials into the biological sterilization indicator 802.

The biological sterilization indicator 802 functions similarly to the biological sterilization indicator 802 illustrated in FIGS. 12A-12C and described above, except that the biological sterilization indicator 802 is oriented differently, such that the plunger 894 moves between a first higher position 887, a second lower position 889, and a third lower position 893 within the housing 810 of the biological sterilization indicator 802. As a result, in some embodiments, when the frangible container 848 has been broken and the liquid 830 has been released from the second reservoir 828 defined by the frangible container 848, gravity can assist the movement of the liquid 830 into the third reservoir 829, without the liquid 830 backing into the first reservoir 822.

FIGS. 14A-14C schematically illustrate a biological sterilization indicator 902 according to another embodiment of the present disclosure. The biological sterilization indicator 902 includes many of the same elements and features described above with reference to the biological sterilization indicator 102 of FIGS. 1-4 and the biological sterilization indicator 702 of FIGS. 12A-12C. Accordingly, elements and features corresponding to elements and features in the illustrated embodiment of FIGS. 1-4 and 12A-12C are provided with the same reference numerals in the 900 series. Reference is made to the description above accompanying FIGS. 1-4 and 12A-12C for a more complete description of the features and elements (and alternatives to such features and elements) of the embodiment illustrated in FIGS. 14A-14C.

The biological sterilization indicator 902 includes a housing 910, a first reservoir 922, a locus 924 of spores located on a fracturing member 964, a second reservoir 928 that contains a liquid 930, and a frangible barrier or cover 749 positioned to separate the first reservoir 922 and the second reservoir 928. The frangible barrier 949 is positioned in the housing 910 along a path of the fracturing member 964. The biological sterilization indicator 902 further includes a sterilant path 932 positioned to fluidly couple the first reservoir 922 to ambience during sterilization.

The fracturing member 964 is movable within the first reservoir 922 along a longitudinal axis of the biological sterilization indicator 902 by a plunger 994. The plunger 994, or at least an upper portion of the plunger 994 can be dimensioned to fit within the first reservoir 922 and can include a seal to seal the first reservoir 922. The plunger 994 can be moved manually, for example, by a handle (not shown), or the plunger 994 can be moved by an actuator, either directly or indirectly, of a detection device, such that the plunger 994 moves between a first position 987, shown in FIG. 14A, a second position 989, shown in FIG. 14B, and a third position 993 shown in FIG. 14C.

FIGS. 14A-14C schematically illustrate the biological sterilization indicator 902 at three points in time, respectively. FIG. 14A shows the biological sterilization indicator 902 at a point in time before or during sterilization. FIGS. 14B and 14C show the biological sterilization indicator 902 after sterilization.

In FIG. 14A, the plunger 994, the fracturing member 964 and the locus 924 of spores are in a first position 987 within the first reservoir 922. The first reservoir 922 is in fluid communication with ambience via the sterilant path 932, and the second reservoir 928 (and the liquid 930) is not in fluid communication with the first reservoir 922, ambience, or sterilant. That is, the frangible barrier 949 is intact, and the second reservoir 928 is in a closed state.

FIG. 14B shows schematically what occurs as the plunger 994, the fracturing member 964 and the locus 924 of spores are moved in the first reservoir 922. At the point in time shown in FIG. 14B, plunger 994, the fracturing member 964 and the locus 924 of spores have moved into the second position 989. The frangible barrier 949 has been fractured by the fracturing member 964, second reservoir 928 has changed from its closed state to its open state, the locus 924 of spores has begun moving into the second reservoir 928, and the first reservoir 922 is still in fluid communication with ambience via the sterilant path 932. The fracturing member 964 and the locus 924 of spores are essentially being dipped into the liquid 930 in the second reservoir 928.

FIG. 14C shows the plunger 994, the fracturing member 964 and the locus 924 of spores in the third position 993, such that the locus 924 of spores has been positioned in the second reservoir 928 so that the liquid 930 is in contact with the spores, and the plunger 994 has sealed off the sterilant path 932, such that the first reservoir 922 is no longer in fluid communication with ambience. Such sealing of the sterilant path 932 inhibits evaporation of the liquid 930 and minimizes the introduction of any contaminating or foreign organisms, objects or materials into the biological sterilization indicator 902.

Even though the biological sterilization indicator 902 is shown oriented such that the plunger 994 moves downwardly in the biological sterilization indicator 902, the biological sterilization indicator 902 can be used in any orientation. For example, the biological sterilization indicator 902 can be oriented such that as the biological sterilization indicator 902 is moved into a recess of the detection device, the plunger 994 can be actuated by an actuator of the detection device.

FIGS. 15A-15D schematically illustrate a biological sterilization indicator 1002 according to another embodiment of the present disclosure. The biological sterilization indicator 1002 includes many of the same elements and features described above with reference to the biological sterilization indicator 102 of FIGS. 1-4 and the biological sterilization indicator 702 of FIGS. 12A-12C. Accordingly, elements and features corresponding to elements and features in the illustrated embodiment of FIGS. 1-4 and 12A-12C are provided with the same reference numerals in the 1000 series. Reference is made to the description above accompanying FIGS. 1-4 and 12A-12C for a more complete description of the features and elements (and alternatives to such features and elements) of the embodiment illustrated in FIGS. 15A-15D.

The biological sterilization indicator 1002 includes a housing 1010, a first reservoir 1022, a frangible container 1048 that defines a second reservoir 1028 that contains a liquid 1030, a locus 1024 of spores positioned in a spore reservoir 1026, a recess 1007 defined in the housing 1010 that is fluid communication with the spore reservoir 1026 and also with ambience via a sterilant path 1032. The sterilant path 1032 is positioned to fluidly couple at least one of the recess 1007, the spore reservoir 1026, and the first reservoir 1022 to ambience during sterilization.

The biological sterilization indicator 1002 further includes a plunger 1094 that is movable along a longitudinal axis of the biological sterilization indicator 1002. The plunger 1094 includes an upper portion 1094a dimensioned to be received in and to form a seal in the recess 1007 and a lower portion 1094b dimensioned to be received in the first reservoir 1022. The lower portion 1094b is also dimensioned to abut the frangible container 1048 as the plunger 1094 is moved in the biological sterilization indicator 1002. The plunger 1094 can also include a seal 1096 (e.g., an elastomeric seal, such as an o-ring) dimensioned to be received in and to seal the first reservoir 1022 as the lower portion 1094b of the plunger 1094 is moved into a position to break the frangible container 1048. The plunger 1094 can be moved manually, for example, by a handle (not shown), or the plunger 1094 can be moved by an actuator, either directly or indirectly, of a detection device, such that the plunger 1094 moves between a first position 1087 shown in FIG. 15A, a second position 1089a shown in FIG. 15B, a third position 1089b shown in FIG. 15C, and a fourth position 1093 shown in FIG. 15D.

FIGS. 15A-15D schematically illustrate the biological sterilization indicator 1002 at four points in time, respectively. FIG. 15A shows the biological sterilization indicator 1002 at a point in time before or during sterilization. FIGS. 15B-15D show the biological sterilization indicator 1002 after sterilization.

In FIG. 15A, the plunger 1094 is in the first position 1087. The spore reservoir 1026 and the locus 1024 of spores are in fluid communication with ambience via the sterilant path 1032, and the frangible container 1048 and the second reservoir 1028 defined by the frangible container 1048 (and the liquid 1030) is not in fluid communication with the first reservoir 1022, the spore reservoir 1026, ambience, or sterilant. That is, the second reservoir 1028 is in a closed state.

FIGS. 15B and 15C show schematically what occurs as the plunger 1094 is moved in the biological sterilization indicator 1002. At the point in time shown in FIG. 15B, plunger 1094 has moved into the second position 1089a, such that the lower portion 1094b of the plunger 1094 has moved into contact with the frangible container 1048, the bottom of the frangible container 1048 has moved into contact with a portion of the housing 1010 that defines the first reservoir 1022, and the seal 1096 has sealed the first reservoir 1022. In FIG. 15C, the plunger 1094 has moved into the third position 1089b, such that the lower portion 1094b of the plunger 1094 has broken the frangible container 1048, changing the second reservoir 1028 changed from its closed state to its open state, causing the liquid 1030 to move into the spore reservoir 1026. In FIGS. 15B and 15C, the first reservoir 1022 is still in fluid communication with ambience via the sterilant path 1032.

The liquid 1030 can move into the spore reservoir 1026 by one or more of gravity and a pressure differential that is created by sealing the first reservoir 1022 and breaking the frangible container 1048. Alternatively, in some embodiments, the first reservoir 1022 can be fluidly coupled to the spore reservoir 1026 by a channel, similar to embodiments described above. In some embodiments, the portion of the recess 1007 downstream of the spore reservoir 1026 between the spore reservoir 1026 and the sterilant path 1032 can be considered a portion of the sterilant path 1032 and can be dimensioned accordingly. In some embodiments, the portion of the recess 1007 downstream of the spore reservoir 1026 can be considered a portion of the spore reservoir 1026. Different configurations and relative dimensions are possible to achieve a suitable biological sterilization indicator 1002 according to the present disclosure. The aspect ratios of one or more of the spore reservoir 1026 to the recess 1007 or the sterilant path 1032 or a channel between the first reservoir 1022 and the spore reservoir 1026 (if employed) can be of the ratios described above to minimize diffusion of any signal out of the spore reservoir 1026 and to maximize the detected signal.

FIG. 15D shows the plunger 1094 in the fourth position 1093, such that the liquid 1030 has filled the spore reservoir 1026 and is in contact with the spores, and the plunger 1094 has sealed off the sterilant path 1032, such that the first reservoir 1022, the spore reservoir 1026, and the recess 1007 are no longer in fluid communication with ambience. Such sealing of the sterilant path 1032 inhibits evaporation of the liquid 1030 and minimizes the introduction of any contaminating or foreign organisms, objects or materials into the biological sterilization indicator 1002.

Even though the biological sterilization indicator 1002 is shown oriented such that the plunger 1094 moves downwardly in the biological sterilization indicator 1002, the biological sterilization indicator 1002 can be used in any orientation. For example, the biological sterilization indicator 1002 can be oriented such that as the biological sterilization indicator 1002 is moved into a recess of a detection device, the plunger 1094 can be actuated by an actuator of the detection device.

FIGS. 16A-16D schematically illustrate a biological sterilization indicator 1102 according to another embodiment of the present disclosure. The biological sterilization indicator 1102 includes many of the same elements and features described above with reference to the biological sterilization indicator 102 of FIGS. 1-4 and the biological sterilization indicator 902 of FIGS. 14A-14C. Accordingly, elements and features corresponding to elements and features in the illustrated embodiment of FIGS. 1-4 and 14A-14C are provided with the same reference numerals in the 1100 series. Reference is made to the description above accompanying FIGS. 1-4 and 14A-14C for a more complete description of the features and elements (and alternatives to such features and elements) of the embodiment illustrated in FIGS. 16A-16D.

The biological sterilization indicator 1102 includes a housing 1110, a first reservoir 1122, a locus 1124 of spores located in a spore reservoir 1126 defined by a hollow lower portion 1194b of a plunger 1194, a fracturing member 1164 coupled to the lower portion 1194b of the plunger 1194, a second reservoir 1128 that contains a liquid 1130, and a frangible barrier or cover 1149 positioned to separate the first reservoir 1122 and the second reservoir 1128. The frangible barrier 1149 is positioned in the housing 1110 along a path of the plunger 1194 and fracturing member 1164. The biological sterilization indicator 1102 further includes a sterilant path 1132 positioned to fluidly couple the first reservoir 1122 to ambience during sterilization.

The fracturing member 1164 is movable within the first reservoir 1122 along a longitudinal axis of the biological sterilization indicator 1102 by the plunger 1194. The plunger 1194, or at least an upper portion of the plunger 1194 can be dimensioned to fit within the first reservoir 1122 and can include a seal to seal the first reservoir 1122. The plunger 1194 can be moved manually, for example, by a handle (not shown), or the plunger 1194 can be moved by an actuator, either directly or indirectly, of a detection device, such that the plunger 1194 moves between a first position 1187 shown in FIG. 16A, a second position 1189a shown in FIG. 16B, a third position 1189b shown in FIG. 16C, and a fourth position 1193 shown in FIG. 16D.

The locus 1124 of spores can be positioned atop a pedestal within the spore reservoir 1126 defined by the plunger 1194; the locus 1124 of spores can be coupled to an inner surface of the hollow lower portion 1194b of the plunger 1194, or the locus 1124 of spores can be positioned within the spore reservoir 1126 defined by the plunger 1194 by other suitable means. The hollow lower portion 1194b of the plunger 1194 further includes one or more apertures 1198 (two are shown in FIGS. 16A-16D), such that the spore reservoir 1126 is in fluid communication with the exterior of the plunger 1194 (e.g., with the first reservoir 1122 or the second reservoir 1128, depending on the position of the plunger 1194) via the apertures 1198.

Figure 16A:
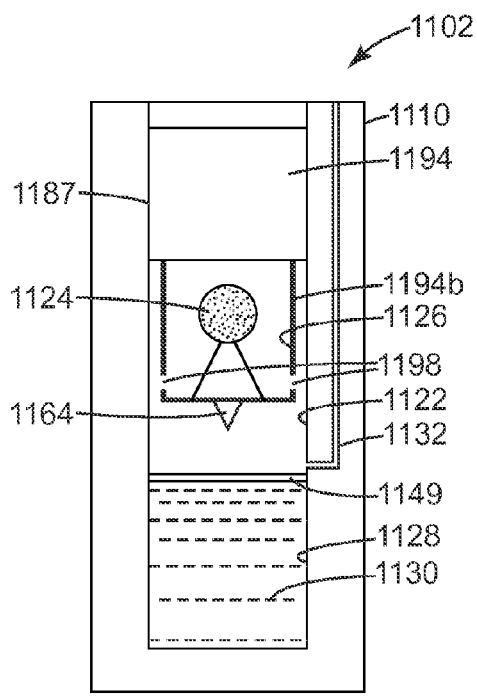
FIGS. 16A-16D are schematic views of a biological sterilization indicator according to another embodiment of the present disclosure.
Figure 16B:
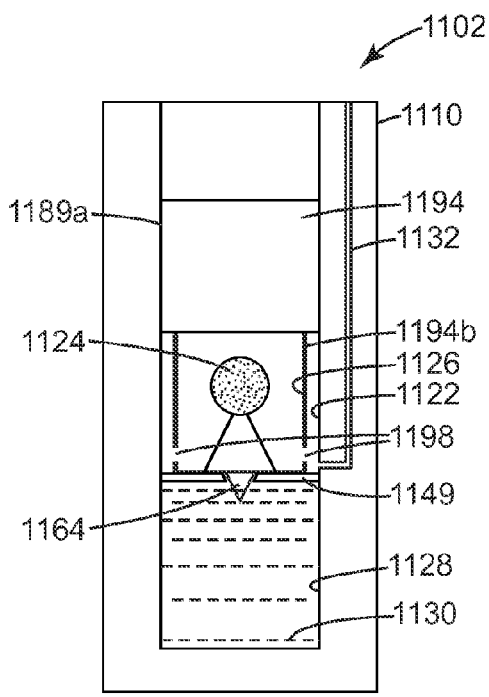
Figure 16C:
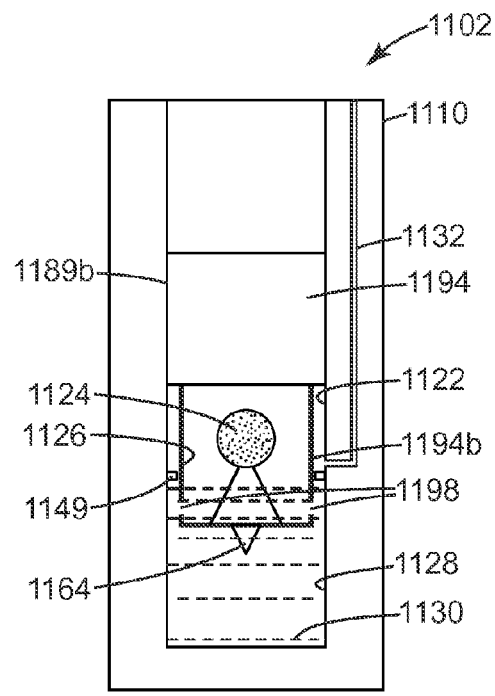
Figure 16D:
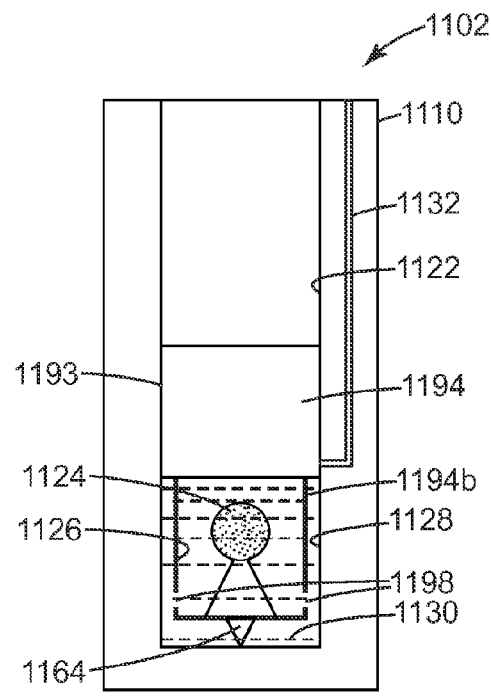

FIGS. 16A-16D schematically illustrate the biological sterilization indicator 1102 at four points in time, respectively. FIG. 16A shows the biological sterilization indicator 1102 at a point in time before or during sterilization. FIGS. 16B-16D show the biological sterilization indicator 1102 after sterilization.

In FIG. 16A, the plunger 1194, the fracturing member 1164 and the locus 1124 of spores are in a first position 1187 within the first reservoir 1122. The first reservoir 1122 is in fluid communication with ambience via the sterilant path 1132, and the second reservoir 1128 (and the liquid 1130) is not in fluid communication with the first reservoir 1122, ambience, or sterilant. That is, the frangible barrier 1149 is intact and the second reservoir 1128 is in a closed state.

FIGS. 16B and 16C show schematically what occurs as the plunger 1194 is moved in the biological sterilization indicator 1102. At the point in time shown in FIG. 16B, plunger 1194 has moved into the second position 1189a, such that the fracturing member 1164 has begun to fracture the frangible barrier 1149 and the lower portion 1194b of the plunger 1194 has moved into contact with the frangible barrier 1149, which begins to change the second reservoir 1128 from a closed state to an open state. In FIG. 16C, the plunger 1194 has moved into the third position 1189b, such that the lower portion 1194b of the plunger 1194 has pushed through the frangible barrier 1149, allowing the liquid 1130 up around the lower portion 1194b of the plunger 1194 and into the spore reservoir 1126. The lower portion 1194b of the plunger 1194 displaces the liquid 1130 in the second reservoir 1128. The spore reservoir 1126 is positioned in the interior of the hollow lower portion 1194b of the plunger 1194, such that as the lower portion 1194b of the plunger 1194 is pushed through the frangible barrier 1149, the spores are not disrupted by the frangible barrier 1149, but rather are protected by the lower portion 1194b of the plunger 1194. In FIGS. 16B and 16C, the first reservoir 1122 is still in fluid communication with ambience via the sterilant path 1132.

FIG. 16D shows the plunger 1194 in the fourth position 1193, such that the liquid 1130 has filled the spore reservoir 1126 and is in contact with the spores, and the plunger 1194 has sealed off the sterilant path 1132, such that the first reservoir 1122 and the spore reservoir 1126 are no longer in fluid communication with ambience. Such sealing of the sterilant path 1132 inhibits evaporation of the liquid 1130 and minimizes the introduction of any contaminating or foreign organisms, objects or materials into the biological sterilization indicator 1102.

Even though the biological sterilization indicator 1102 is shown oriented such that the plunger 1194 moves downwardly in the biological sterilization indicator 1102, the biological sterilization indicator 1102 can be used in any orientation. For example, the biological sterilization indicator 1102 can be oriented such that as the biological sterilization indicator 1102 is moved into a recess of the detection device, the plunger 1194 can be actuated by an actuator of the detection device.

FIGS. 17A-17D schematically illustrate a biological sterilization indicator 1202 according to another embodiment of the present disclosure. The biological sterilization indicator 1202 includes many of the same elements and features described above with reference to the biological sterilization indicator 102 of FIGS. 1-4 and the biological sterilization indicator 1102 of FIGS. 16A-16D. Accordingly, elements and features corresponding to elements and features in the illustrated embodiment of FIGS. 1-4 and 16A-16D are provided with the same reference numerals in the 1200 series. Reference is made to the description above accompanying FIGS. 1-4 and 16A-16D for a more complete description of the features and elements (and alternatives to such features and elements) of the embodiment illustrated in FIGS. 17A-17D.

The biological sterilization indicator 1202 includes a housing 1210, a first reservoir 1222, a locus 1224 of spores located in a spore reservoir 1226 defined a middle flat portion 1294b of a plunger 1294, a fracturing member 1264 coupled to a lower cylindrical portion 1294c of the plunger 1294, a second reservoir 1228 that contains a liquid 1230, and a frangible barrier or cover 1249 positioned to separate the first reservoir 1222 and the second reservoir 1228. The frangible barrier 1249 is positioned in the housing 1210 along a path of the plunger 1294 and fracturing member 1264. The biological sterilization indicator 1202 further includes a sterilant path 1232 positioned to fluidly couple the first reservoir 1222 to ambience during sterilization.

The fracturing member 1264 is movable within the first reservoir 1222 along a longitudinal axis of the biological sterilization indicator 1202 by the plunger 1294. The plunger 1294, or at least an upper portion of the plunger 1294 can be dimensioned to fit within the first reservoir 1222 and can include a seal to seal the first reservoir 1222. The plunger 1294 can be moved manually, for example, by a handle (not shown), or the plunger 1294 can be moved by an actuator, either directly or indirectly, of a detection device, such that the plunger 1294 moves between a first position 1287 shown in FIG. 17A, a second position 1289*a* shown in FIG. 17B, a third position 1289*b* shown in FIG. 17C, and a fourth position 1293 shown in FIG. 17D.

The locus 1124 of spores can be coupled to an outer surface of the middle flat (i.e., substantially planar) middle portion 1294*b* of the plunger 1294, and the fracturing member 1264 can be coupled to the lower cylindrical portion 1294*c* of the plunger 1294. The middle and lower portions 1294*b* and 1294*c* of the plunger 1294 are shown as being symmetrical, and the spores are shown as being coupled to one side of the middle flat portion 1294*b*. However, it should be understood that an additional locus (or loci) of spores can be positioned on the other side of the middle flat portion 1294*b* as well. In addition, it should be understood that the plunger 1294 can instead be asymmetrically shaped, such that the middle flat portion 1294*b* is positioned toward one side of the lower cylindrical portion 1294*c*, and the locus 1224 of spores faces toward the opposite side of the lower cylindrical portion 1294*c*.

The lower cylindrical portion 1294*c* of the plunger 1294 is shaped such that as the plunger 1294 is moved downwardly in the first reservoir 1222, and the fracturing member 1264 fractures the frangible barrier 1249, the lower cylindrical portion 1294*c* can fill the second reservoir 1228 to displace the liquid 1230. As a result, the liquid 1230 can be caused to move around the outside of the lower cylindrical portion 1294*c* of the plunger 1294 to the spore reservoir 1226, which is defined at least partially by the space between the middle flat portion 1294*b* of the plunger 1294 and the walls defining the first reservoir 1222. The liquid 1230 contacts the locus 1224 of spores and surrounds the middle flat portion 1294*b* of the plunger 1294.

FIGS. 17A-17D schematically illustrate the biological sterilization indicator 1202 at four points in time, respectively. FIG. 17A shows the biological sterilization indicator 1202 at a point in time before or during sterilization. FIGS. 17B-17D show the biological sterilization indicator 1202 after sterilization.

In FIG. 17A, the plunger 1294, the fracturing member 1264 and the locus 1224 of spores are in a first position 1287 within the first reservoir 1222. The first reservoir 1222 is in fluid communication with ambience via the sterilant path 1232, and the second reservoir 1228 (and the liquid 1230) is not in fluid communication with the first reservoir 1222, ambience, or sterilant. That is, the frangible barrier 1249 is intact and the second reservoir 1228 is in a closed state.

FIGS. 17B and 17C show schematically what occurs as the plunger 1294 is moved in the biological sterilization indicator 1202. At the point in time shown in FIG. 17B, plunger 1294 has moved into the second position 1289*a*, such that the fracturing member 1264 has begun to fracture the frangible barrier 1249, which begins to change the second reservoir 1228 from a closed state to an open state. In FIG. 17C, the plunger 1294 has moved into the third position 1289*b*, such that the lower cylindrical portion 1294*c* of the plunger 1294 has pushed through the frangible barrier 1249, allowing the liquid 1230 up around the lower cylindrical portion 1294*c* of the plunger 1294 and into the spore reservoir 1226. The lower cylindrical portion 1294*c* of the plunger 1294 displaces the liquid 1230 in the second reservoir 1228. The spore reservoir 1226 is positioned adjacent the middle flat portion 1294*b* of the plunger 1294, such that as the lower cylindrical portion 1294*c* of the plunger 1294 is pushed through the frangible barrier 1249, the spores are not disrupted by the frangible barrier 1249, but rather are protected by the lower cylindrical portion 1294*c* of the plunger 1294. In FIGS. 17B and 17C, the first reservoir 1222 is still in fluid communication with ambience via the sterilant path 1232.

FIG. 17D shows the plunger 1294 in the fourth position 1293, such that the liquid 1230 has filled the spore reservoir 1226 and is in contact with the spores, and the plunger 1294 has sealed off the sterilant path 1232, such that the first reservoir 1122 and the spore reservoir 1226 are no longer in fluid communication with ambience. Such sealing of the sterilant path 1232 inhibits evaporation of the liquid 1230 and minimizes the introduction of any contaminating or foreign organisms, objects or materials into the biological sterilization indicator 1202.

The shape of the middle and lower portions 1294*b* and 1294*c* of the plunger 1294 are shown by way of example only; however, it should be understood that other shapes and configurations are possible to allow a portion of the plunger 1294 to displace the liquid 1230, such that the liquid 1230 is moved into contact with the locus 1224 of spores, while protecting the locus 1224 of spores from passing through the frangible barrier 1249.

Even though the biological sterilization indicator 1202 is shown oriented such that the plunger 1294 moves downwardly in the biological sterilization indicator 1202, the biological sterilization indicator 1202 can be used in any orientation. For example, the biological sterilization indicator 1202 can be oriented such that as the biological sterilization indicator 1202 is moved into a recess of the detection device, the plunger 1294 can be actuated by an actuator of the detection device.

FIGS. 18-21 illustrate a biological sterilization indicator 1302 according to another embodiment of the present disclosure. The biological sterilization indicator 1302 includes many of the same elements and features described above with reference to the biological sterilization indicator 102 of FIGS. 1-4 and the biological sterilization indicator 202 of FIG. 5. Accordingly, elements and features corresponding to elements and features in the illustrated embodiment of FIGS. 1-4 and 5 are provided with the same reference numerals in the 1300 series. Reference is made to the description above accompanying FIGS. 1-4 and 5 for a more complete description of the features and elements (and alternatives to such features and elements) of the embodiment illustrated in FIGS. 18-21.

The biological sterilization indicator 1302 includes a housing 1310 defined by a top wall 1312 formed by a cap 1309, a cylindrical wall 1316, and a bottom wall 1321, all of which are liquid impermeable. In some embodiments, the cap 1309 is integrally formed with the cylindrical wall 1316 and in some embodiments, the cap 1309 is coupled to the wall 1316. In embodiments in which the cap 1309 is coupled to the wall 1316, the cap 1309 can be permanently or removably coupled to the wall 1316.

The biological sterilization indicator 1302 further includes a plurality of loci 1324 of spores positioned in a spore reservoir 1326 that is defined by the housing 1310. The biological sterilization indicator 1302 further includes a frangible container 1348 that defines a second reservoir 1328 that contains a liquid 1330, and a sterilant path 1332 positioned to provide fluid communication between the spore reservoir 1326 and ambience. The sterilant path 1332 includes and an inlet 1334 in the cylindrical wall 1316 of the housing 1310, and an outlet 1338 that opens into the spore reservoir 1326.

The biological sterilization indicator 1302 further includes a cap 1360 that is dimensioned to fit around the frangible container 1348 and to engage at least a portion of the cylindrical wall 1316 of the housing 1310. The cap 1360 has a partially cylindrical wall 1361 and two protrusions 1363 that extend the height of the cap 1360 and are directed radially inwardly, such that as the cap 1360 is positioned over the cylindrical wall 1316 of the housing 1310, the protrusions 1363 can engage the housing 1310 (or a mating feature on the housing 1310), for example, in a snap-fit engagement.

Figure 18:
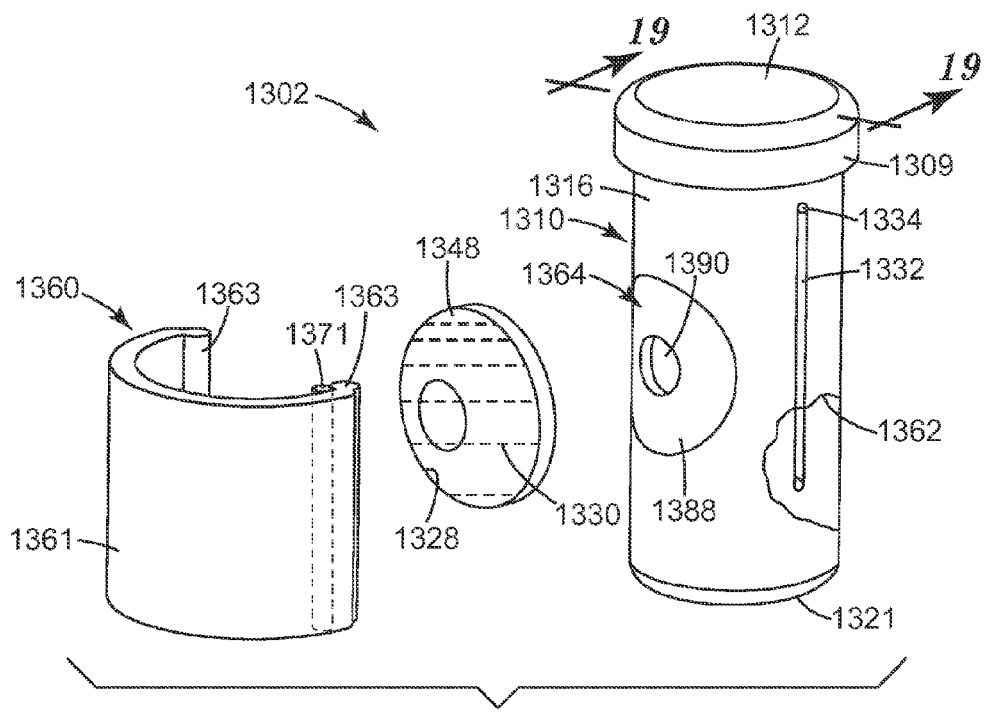
FIG. 18 is a rear exploded perspective view of a biological sterilization indicator according to another embodiment of the present disclosure, the biological sterilization indicator including a housing.
Figure 19:
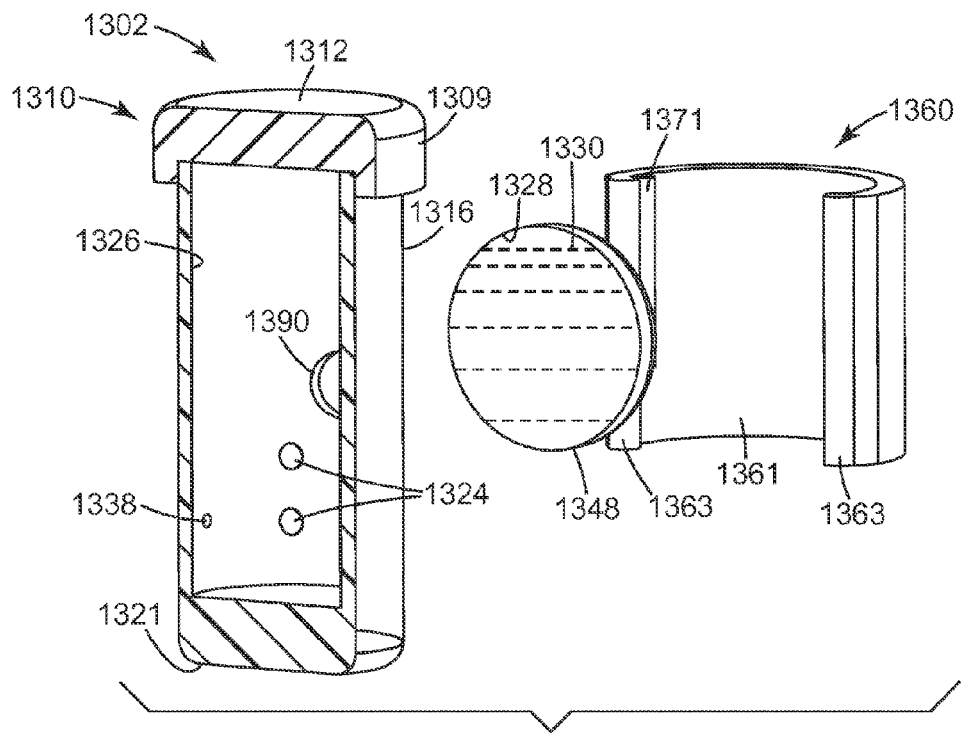
FIG. 19 is a front exploded view of the biological sterilization indicator of FIG. 18, the housing shown in cross-section, taken along line 19-19 in FIG. 18.

The biological sterilization indicator 1302 further includes a fracturing member 1364. As shown in FIG. 18, the fracturing member 1364 includes at least a portion of an outer surface 1388 of the housing 1310 and an aperture 1390 formed in the outer surface 1388 of the housing 1310, and which is positioned to provide fluid communication between ambience and the spore reservoir 1326 in the biological sterilization indicator 1302. Because the aperture 1390 extends through the thickness of the cover 1388, the aperture 1390 can be considered a channel that fluidly couples ambience and the spore reservoir 1326, and particularly, when the frangible container 1348 is in an open state, the channel fluidly couples the second reservoir 1328 defined by the frangible container 1348 with the spore reservoir 1326, such that the liquid 1330 is in fluid communication with the spore reservoir 1326.

The biological sterilization indicator 1302 can further include a cover 1362 positioned over the housing 1310 to seal the interior of the housing 1310 from ambience. Such a cover 1362 can be formed of a variety of materials, including, but not limited to, a metal, a polymer, a coating, a tape (e.g., a polymer backing and an adhesive applied to one or more sides of the polymer backing), or a combination thereof. For example, in some embodiments, the cover 1362 can be a thin film. In some embodiments, the cover 1362 can be formed of the same material as the cylindrical wall 1316 of the housing 1310. The cover 1362 can be positioned internally or externally (i.e., forwardly or rearwardly) with respect to the frangible container 1348, and can also be liquid impermeable. In some embodiments, the aperture 1390 (and optionally, the portion of the outer surface 1388 of the housing 1310 that forms the fracturing member 1364) is free of the cover 1362, and in some embodiments, the cover 1362 is formed over the aperture 1390 but is adapted to fracture when the frangible container 1348 fractures.

Figure 20:
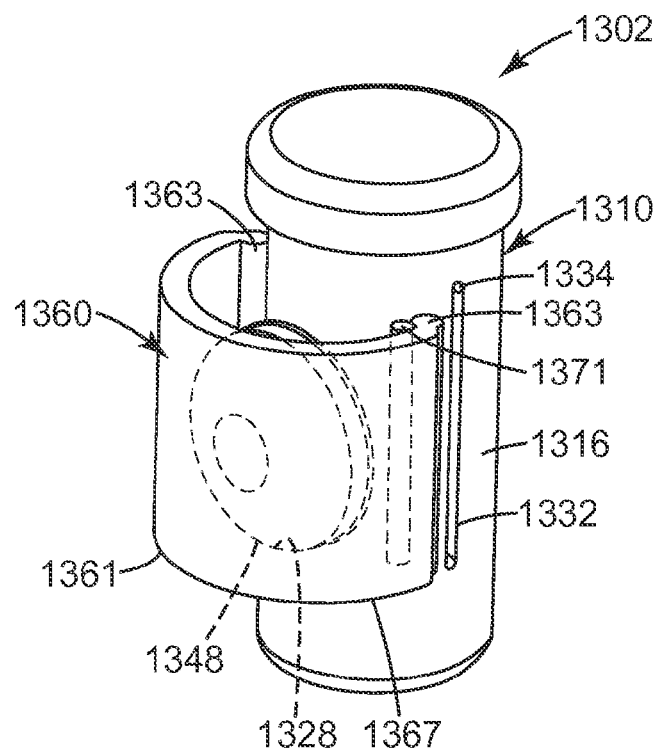
FIG. 20 is a rear assembled perspective view of the biological sterilization indicator of FIGS. 18 and 19, shown in a first position.
Figure 21:
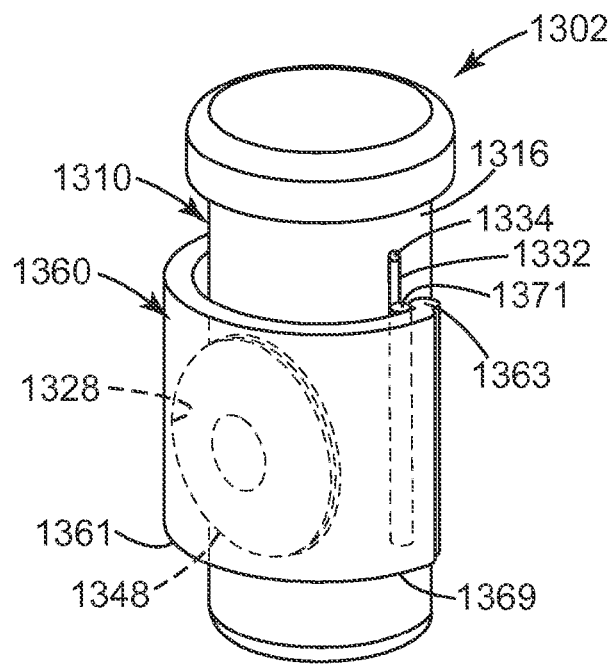
FIG. 21 is a rear assembled perspective view of the biological sterilization indicator of FIGS. 18-20, shown in a second position.

As shown in FIGS. 20 and 21, the cap 1360 is movable between a first position 1367 relative to the housing 1310 in which the protrusions 1363 are not engaged with the housing 1310, and a second position 1369 relative to the housing 1310 in which the protrusions 1363 are engaged with at least a portion of the housing 1310. The cap 1360 further includes a seal 1371 configured to seal at least a portion of the sterilant path 1332 when the cap 1360 is in the second position 1369.

As shown in FIG. 20, before and/or during sterilization, the cap 1360 can be positioned in the first position 1367 near or in abutting relationship with the frangible container 1348, which is also near or in abutting relationship with the housing 1310. The frangible container 1348 is intact, the second reservoir 1328 is in a closed state, and the liquid 1330 is contained in the frangible container 1348. In addition, the spore reservoir 1326 is in fluid communication with ambience via the sterilant path 1332.

As shown in FIG. 21, after sterilization, the cap 1360 can be moved into the second position 1369 in which the cylindrical wall 1361 of the cap 1360 presses the frangible container 1348 against fracturing member 1364, and particularly, against the outer surface 1388 of the housing 1310. The only portion of the frangible container 1348 that is not supported by the outer surface 1388 of the housing 1310 is the portion of the frangible container 1348 adjacent the aperture 1390. As a result, the frangible container 1348 can fracture, and expel the liquid 1330 into the spore reservoir 1326 via the aperture 1390. In some embodiments, the front portion of the frangible container 1348 (i.e., the portion facing the housing 1310 and the spore reservoir 1326) can be formed of a weaker, more frangible, material than the rear portion (i.e., the portion facing away from the housing 1310), such that the front portion of the frangible container breaks against the outer surface 1388 of the housing 1310 more easily than against the wall 1361 of the cap 1360.

In addition, as shown in FIG. 21, when the cap 1360 is moved into the second position 1369, the seal 1371 is moved into a position to block at least a portion of the sterilant path 1332. Particularly, in the embodiment illustrated in FIGS. 18-21, the seal 1371 presses the cover 1362 into the sterilant path 1332, thereby obstructing the respective portion of the sterilant path 1362, such that the spore reservoir 1326 is no longer in fluid communication with ambience, the liquid 1330 in the spore reservoir 1326 is protected from evaporation and the introduction of contaminating or foreign organisms, objects or materials into the biological sterilization indicator 1302 is minimized.

The seal 1371 is shown by way of example only; however, it should be understood that a variety of configurations of the seal 1371 are possible. For example, in some embodiments, the seal 1371 includes a pad (e.g., an elastomeric pad) that is movable into a position to cover the inlet 1334 of the sterilant path 1332 (e.g., an opening in the cover 1362) when the cap 1360 is moved into the second position 1369.

By way of example only, the cap 1360 is illustrated in FIGS. 18-21 as being a portion of the biological sterilization indicator 1302. In such embodiments, the cap 1360 can be actuated to move between the first and second positions 1367 and 1369 by an actuator of a detection device. For example, in some embodiments, such an actuator can actuate the cap 1360 as the biological sterilization indicator 1302 is positioned within a recess of the detection device. In some embodiments, however, the cap 1360 can be provided by the detection device itself and coupled to or actuated, either directly or indirectly, by an actuator of the detection device. Similarly, in some embodiments, the frangible container 1348 can be provided by the detection device.

In the embodiment illustrated in FIGS. 18-21, the biological sterilization indicator 1302 does not include a first reservoir like the embodiments illustrated in FIGS. 1-17D and described above. In the biological sterilization indicator 1302, the frangible container 1348 is positioned adjacent the outer surface 1388 of the housing 1310, and is pressed against the outer surface 1388 when the cap 1360 is in the second position 1369, such that the liquid 1330 can move into the spore reservoir 1326 in the housing 1310 without being expelled exterior to the housing 1310. Additional sealing mechanisms or features can be employed to ensure a fluid tight fluid transfer from the second reservoir 1328 in the frangible container 1348 to the spore reservoir 1326. However, it should be understood that, in some embodiments, the biological sterilization indicator 1302 can include an additional layer or wall (e.g., at least a portion of the cap 1360) surrounding the frangible container 1348 that forms a first reservoir. For example, the additional layer or wall can be deformable or can include a deformable portion that can cooperate with the cap 1360. In some embodiments, the cover 1362 can function as this layer and form a first reservoir. In such embodiments, other features described above with respect to the other embodiments can also be employed, such as a longer channel fluidly coupling the first reservoir to the spore reservoir 1326, an additional sterilant path or vent positioned to fluidly couple the first reservoir to ambience, etc.

In the embodiment illustrated in FIGS. 18-21, the frangible container 1348 is positioned externally to the housing 1310, and the spore reservoir 1326 is positioned in the housing 1310. However, in some embodiments, the reverse configuration can be employed, such that the spore reservoir 1326 is positioned externally to the housing 1310, and the frangible container 1348 is positioned in the housing 1310. Alternatively, in some embodiments, the housing 1310 itself can define the second reservoir 1328 that contains the liquid 1330, and one or both ends of the aperture/channel 1390 can be covered with a frangible barrier or cover. In embodiments in which the spores are positioned externally to the housing 1310, the spore reservoir 1326 can be defined at least partially by the outer surface 1388 of the housing 1310 and an additional layer, such as the cover 1362. In such embodiments, any additional layer or wall forming or defining at least a portion of the spore reservoir 1326 can be coupled to or integrally formed with the housing 1310 depicted in FIGS. 18-21, such that the locus of spores is still considered to be positioned within the "housing" of the biological sterilization indicator 1302. In addition, the spore reservoir 1326 can include a spore carrier, such as those described above. By way of example only, in some embodiments, the spore carrier can include a wicking material (e.g., a microstructured carrier, a microporous paper, polymer, cloth, etc., or combinations thereof) to facilitate the flow of liquid 1330 from the interior of the housing 1310 into the spore reservoir 1326 (e.g., when the second reservoir 1328 is in its open state). Furthermore, in such embodiments, a different type of fracturing member can be employed. For example, a fracturing member that includes a blunt end or a hammer adapted to break the frangible container 1348 can be employed in the wall of the housing 1310, the fracturing member positioned to be actuated by an actuator (e.g., an actuator of a detection device).

Figures 22, 23:
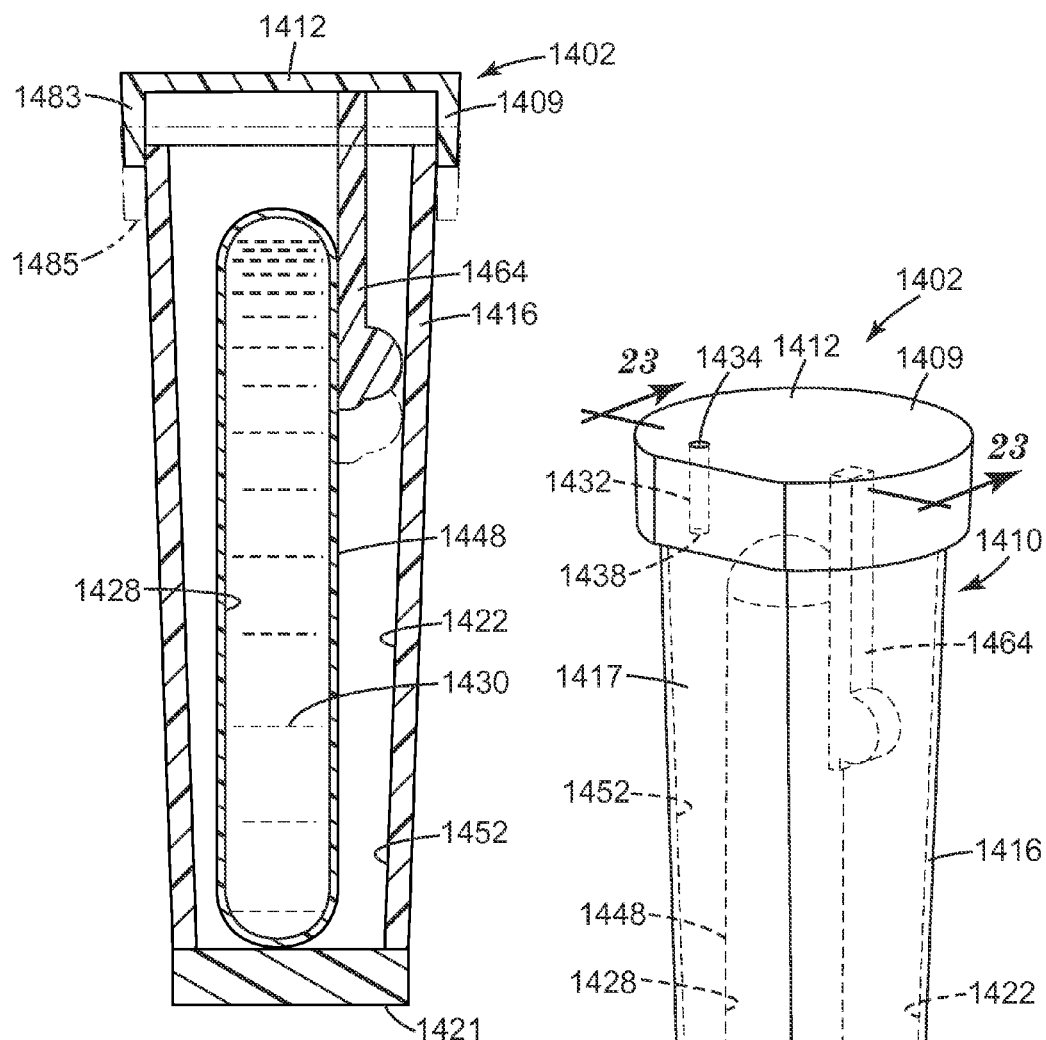
FIG. 22 is a rear exploded perspective view of a biological sterilization indicator according to another embodiment of the present disclosure.
FIG. 23 is a side cross-sectional view of the biological sterilization indicator of FIG. 22, taken along line 23-23.

FIGS. 22-23 illustrate a biological sterilization indicator 1402 according to another embodiment of the present disclosure. The biological sterilization indicator 1402 includes many of the same elements and features described above with reference to the biological sterilization indicator 102 of FIGS. 1-4 and the biological sterilization indicator 502 of FIG. 8. Accordingly, elements and features corresponding to elements and features in the illustrated embodiment of FIGS. 1-4 and 8 are provided with the same reference numerals in the 1400 series. Reference is made to the description above accompanying FIGS. 1-4 and 8 for a more complete description of the features and elements (and alternatives to such features and elements) of the embodiment illustrated in FIGS. 22-23.

The biological sterilization indicator 1402 includes a housing 1410 defined by a top wall 1412 formed by a cap 1409, a sidewall 1416 having a substantially cylindrical shape with one flat wall 1417, and a bottom wall 1421, all of which are liquid impermeable. In some embodiments, the cap 1409 is integrally formed with the sidewall 1416 and in some embodiments, the cap 1409 is coupled to the wall 1416. In embodiments in which the cap 1409 is coupled to the wall 1416, the cap 1409 can be permanently or removably coupled to the wall 1416.

The biological sterilization indicator 1402 further includes a plurality of loci 1424 of spores positioned on a carrier 1425 in a spore reservoir 1426 that is defined by the housing 1410. The biological sterilization indicator 1402 further includes a frangible container 1448 positioned in a first reservoir 1422 defined in the housing 1410. The frangible container 1448 defines a second reservoir 1428 that contains a liquid 1430, and a sterilant path 1432 positioned to provide fluid communication between the first reservoir 1422 and ambience. The sterilant path 1432 includes and an inlet 1434 in the cap 1409, and an outlet 1438 that opens into the first reservoir 1422.

The biological sterilization indicator 1402 further includes a fracturing member 1464. The fracturing member 1464 is shaped and positioned to sit between an upper portion of the frangible container 1448 and an inner surface 1452 of the first reservoir 1422. The first reservoir 1422 tapers from top to bottom, such that as the fracturing member 1464 is moved downwardly in the first reservoir 1422, the fracturing member 1464 will compress against the frangible container 1458, causing it to break, and causing the liquid 1430 to be released into the first reservoir 1422. The fracturing member 1464 can be loose inside the housing 1410, or the fracturing member 1464 can be coupled to the cap 1409. Whether the fracturing member 1464 is loose or coupled to the cap 1409, downward movement of the cap 1409 can cause downward movement of the fracturing member 1464.

As shown in FIG. 23, the cap 1409 (and accordingly, the fracturing member 1464) can be movable between a first position 1483 with respect to the sidewall 1416 in which the fracturing member 1464 is not sufficiently pressed against the frangible container 1458 to cause it to break and a second position 1485 with respect to the sidewall 1416 in which the fracturing member 1464 is sufficiently pressed against the frangible container 1458 to cause it to break. In addition, the cap 1409 can be adapted to seal the sterilant path 1432 when in the second position 1485. Alternatively, the cap 1409 can be movable to a third position in which the sterilant path 1432 is sealed. The movement of the cap 1409 and/or the fracturing member 1464 can be actuated, directly or indirectly, by an actuator of a detection device. In addition, the detection device can include at least a portion of the cap 1409. The shapes and configurations of elements are shown in FIGS. 22-23 by way of example only; however, it should be understood that other relative shapes and configurations between the housing 1410, the fracturing member 1464, the frangible container 1458 and the cap 1409 can be employed to achieve the above-described function.

The biological sterilization indicator 1402 can further include a channel 1492 positioned to fluidly couple the first reservoir 1422 to the spore reservoir 1426. In some embodiments, as shown in FIG. 22, the biological sterilization indicator 1402 can include a wicking material 1441 positioned adjacent the channel 1492. The wicking material 1441 is shown as being positioned externally with respect to the channel 1492; however, it should be understood that, in some embodiments, the wicking material 1441 can be positioned internally with respect to the channel 1492, externally with respect to the channel 1492, at least partially in the channel 1492, or a combination thereof.

As shown in FIG. 22, the biological sterilization indicator 1402 further includes a cover 1454 positioned to cover the loci 1424 of spores and a detection window 1450. As mentioned above, some embodiments do not employ a cover 1454 over the spores, and the spores are positioned directly adjacent the back side of the detection window 1450.

As shown in FIG. 23, before and/or during sterilization, the cap 1409 and the fracturing member 1464 can be positioned in the first position 1483, such that the fracturing member 1464 is near or in abutting relationship with the frangible container 1448 and in near or in abutting relationship with the housing 1410. The frangible container 1448 is intact, the second reservoir 1428 is in a closed state, and the liquid 1430 is contained in the frangible container 1448. In addition, the spore reservoir 1426 is in fluid communication with ambience via the sterilant path 1432 and the first reservoir 1422.

After sterilization, the cap 1409 and the fracturing member 1464 can be moved into the second position 1485 in which the fracturing member 1464 is sandwiched between the housing 1410 and the frangible container 1448, causing the frangible container 1448 to break and the liquid 1430 to be expelled into the first reservoir 1422 and the spore reservoir 1426 via the channel 1492 (and the wicking material 1441).

In some embodiments, one or both of the biological sterilization indicator 1402 and the detection device 1404 can be configured to inhibit premature or accidental movement of the cap 1409 into the second position 1485. For example, in some embodiments, the biological sterilization indicator 102 can include a flange, tab, ring, or the like, that functions as a lock and which is positioned (e.g., adjacent the sidewall 1416 and below the cap 1409) to inhibit movement of the cap 1409 into the second position 1485. In such embodiments, a detection device that is adapted to be coupled to the biological sterilization indicator 1402 can include an actuator that is positioned to move, break or release the lock, such that the cap 1409 can be moved into the second position 1485, for example, when the biological sterilization indicator 1402 is coupled to the detection device 1404.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible. In addition, it should be understood that various elements from one embodiment described above can be used interchangeably with another embodiment without departing from the spirit and scope of the present disclosure. Various features and aspects of the present disclosure are set forth in the following claims.

What is claimed is:

1. A biological sterilization indicator system comprising:
   a housing;
   a locus of spores positioned in the housing;
   a reservoir containing a liquid, the reservoir having a closed state in which the reservoir is not in fluid communication with the locus of spores and an open state in which the reservoir is in fluid communication with the locus of spores;
   a sterilant path positioned to provide fluid communication between ambience and the locus of spores when the reservoir is in a closed state, wherein the sterilant path is further positioned to provide a vent when the reservoir is in the open state;
   a seal positioned to move between a first position relative to the sterilant path in which the locus of spores is in fluid communication with ambience and a second position relative to the sterilant path in which the locus of spores is not in fluid communication with ambience, the seal adapted to be in the second position when the reservoir is in the open state; and
   an actuator adapted to actuate the seal to move between the first position and the second position, wherein the actuator is provided by a cap adapted to be coupled to the housing or a device adapted to be coupled to the housing.

2. The biological sterilization indicator system of claim 1, further comprising a biological sterilization indicator comprising the housing, the locus of spores, the reservoir, and the sterilant path wherein the actuator is provided by a device adapted to be coupled to the housing.

3. The biological sterilization indicator system of claim 2, wherein the biological sterilization indicator further comprises an orientation feature, and wherein the device includes a corresponding orientation feature.

4. The biological sterilization indicator system of claim 2, wherein at least one of the biological sterilization indicator and the device is configured to inhibit the reservoir from changing to its open state prematurely.

5. The biological sterilization indicator system of claim 2, wherein at least one of the biological sterilization indicator and the device includes a lock positioned to inhibit the reservoir from prematurely changing from the closed state to the open state, and wherein at least one of the biological sterilization indicator and the device further includes a key positioned to unlock the lock to allow the reservoir to change from the closed state to the open state.

6. The biological sterilization indicator system of claim 1, wherein the locus of spores is positioned in a spore reservoir, and wherein the spore reservoir includes means for facilitating contact between the liquid and the locus of spores.

7. The biological sterilization indicator system of claim 1, wherein:
   the reservoir includes a first volume of liquid,
   the housing further comprises a spore reservoir in which the locus of spores is positioned, the spore reservoir having a second volume, and
   second volume is less than the first volume.

8. The biological sterilization indicator system of claim 1, wherein the locus of spores is positioned in a spore reservoir and further comprising a channel positioned to fluidly couple the spore reservoir and the reservoir when the reservoir is in the open state.

9. The biological sterilization indicator system of claim 1, further comprising a first reservoir positioned in fluid communication with the locus of spores, wherein the reservoir containing the liquid is a second reservoir and is defined by a frangible container, and wherein the frangible container is positioned within the first reservoir.

10. The biological sterilization indicator system of claim 9, wherein the seal is movable between a first position in which the sterilant path is in fluid communication with the first reservoir and a second position in which the sterilant path is not in fluid communication with the first reservoir.

11. The biological sterilization indicator system of claim 1, wherein the actuator is adapted to change the seal from the first position to the second position when the housing is moved from a first position to a second position relative to the cap or the device.

12. The biological sterilization indicator system of claim 1, wherein the actuator is a first actuator, and further comprising a second actuator adapted to change the reservoir from the closed state to the open state.

13. The biological sterilization indicator system of claim 12, wherein the second actuator is provided by a cap adapted to be coupled to the housing or a device adapted to be coupled to the housing.

14. The biological sterilization indicator system of claim 1, wherein the seal is provided by a biological sterilization indicator of the biological sterilization indicator system.

15. The biological sterilization indicator system of claim 1, wherein the seal is provided by a plunger.

16. The biological sterilization indicator system claim 1, wherein the actuator includes a protrusion positioned to actuate the seal to move between the first position and the second position.

17. The biological sterilization indicator system of claim 1, wherein the actuator is adapted to actuate the seal to move between the first position and the second position in response to the cap or the device being coupled to the housing.

18. The biological sterilization indicator system of claim 1, wherein the locus of spores is positioned in a spore reservoir, and wherein the aspect ratio of the cross-sectional area of the sterilant path adjacent the spore reservoir to the volume of the spore reservoir ranges from about 1:25 to about 1:500.

19. A method for determining the effectiveness of a sterilization process, the method comprising:
- providing a housing;
- providing a locus of spores positioned in the housing;
- providing a reservoir containing a liquid, the reservoir having a closed state in which the reservoir is not in fluid communication with the locus of spores and an open state in which the reservoir is in fluid communication with the locus of spores;
- moving a sterilant into fluid communication with the locus of spores via a sterilant path while the reservoir is in the closed state to form sterilized spores;
- changing the reservoir from the closed state to the open state to combine the liquid and the sterilized spores to form a mixture;
- venting via the sterilant path while the reservoir is changing from the closed state to the open state;
- coupling at least a portion of the housing to a device or a cap; and
- sealing at least a portion of the sterilant path in response to coupling at least a portion of the housing to the device or the cap.

20. The method of claim 19, wherein changing the reservoir from the closed state to the open state occurs as a result of coupling at least a portion of the housing to a device or a cap.

* * * * *

UNITED STATES PATENT AND TRADEMARK OFFICE
CERTIFICATE OF CORRECTION

PATENT NO. : 8,969,029 B2  
APPLICATION NO. : 13/063945  
DATED : March 3, 2015  
INVENTOR(S) : Sailaja Chandrapati It is certified that error appears in the above-identified patent and that said Letters Patent is hereby corrected as shown below:

IN THE SPECIFICATION:

Column 6, Line 47 - delete "polythyene," and insert -- polythene, --, therefor.

Column 10, Line 4 - delete "cellibiose," and insert -- cellobiose, --, therefor.

IN THE CLAIMS:

Column 48, Line 60 - In Claim 16, delete "system claim" and insert -- system of claim --, therefor.

Signed and Sealed this  
Fourth Day of August, 2015

Michelle K. Lee  
*Director of the United States Patent and Trademark Office*